United States Patent
Wang et al.

(10) Patent No.: US 9,096,625 B2
(45) Date of Patent: Aug. 4, 2015

(54) BCL-2/BCL-XL INHIBITORS AND THERAPEUTIC METHODS USING THE SAME

(71) Applicant: THE REGENTS OF THE UNIVERSITY OF MICHIGAN, Ann Arbor, MI (US)

(72) Inventors: Shaomeng Wang, Saline, MI (US); Jianfang Chen, Ann Arbor, MI (US); Donna McEachern, Ann Arbor, MI (US); Longchuan Bai, Ann Arbor, MI (US); Liu Liu, Ann Arbor, MI (US); Duxin Sun, Ann Arbor, MI (US); Xiaoqin Li, Ann Arbor, MI (US); Angelo Aguilar, Ann Arbor, MI (US)

(73) Assignee: THE REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 0 days.

(21) Appl. No.: 14/155,809

(22) Filed: Jan. 15, 2014

(65) Prior Publication Data
US 2014/0199234 A1 Jul. 17, 2014

Related U.S. Application Data

(60) Provisional application No. 61/753,066, filed on Jan. 16, 2013.

(51) Int. Cl.
*A61K 31/675* (2006.01)
*C07F 9/6558* (2006.01)
*A61K 45/06* (2006.01)
*A61K 33/30* (2006.01)

(52) U.S. Cl.
CPC ............ *C07F 9/65583* (2013.01); *A61K 31/675* (2013.01); *A61K 33/30* (2013.01); *A61K 45/06* (2013.01)

(58) Field of Classification Search
None
See application file for complete search history.

(56) References Cited

U.S. PATENT DOCUMENTS

| 2006/0084647 A1 | 4/2006 | Wang et al. |
| 2007/0197532 A1 | 8/2007 | Cao et al. |

FOREIGN PATENT DOCUMENTS

| WO | WO-2010/010154 A1 | 1/2010 |
| WO | WO-2012/017251 A1 | 2/2012 |
| WO | WO-2012/103059 A2 | 8/2012 |

OTHER PUBLICATIONS

Cancer Drug Design and Discovery, Neidle, Stephen,ed. (Elsevier/Academic Press), pp. 427-431 (2008).*
Liu et al. Communicative & Integrative Biology 5:6, pp. 557-565 (2012).*
Chen, J., et al., Structure-Based Discovery of BM-957 as a Potent Small-Molecule Inhibitor of Bcl-2 and Bcl-xL Capable of Achieving Complete Tumor Regression. *Journal of Medicinal Chemistry*, 2012, vol. 55, No. 19, pp. 8502-8514.
Zhou, H., et al., "Structure-Based Design of Potent Bcl-2/Bcl-xL Inhibitors With Strong in Vivo Antitumor Activity." *Journal of Medicinal Chemistry*, 2012, vol. 55, No. 13, pp. 6149-6161.
International Search Report in International Patent Application No. PCT/US2014/011571, dated May 30, 2014.

* cited by examiner

*Primary Examiner* — Emily Bernhardt
(74) *Attorney, Agent, or Firm* — Marshall, Gerstein & Borun LLP

(57) ABSTRACT

Inhibitors of Bcl-2/Bcl-xL and compositions containing the same are disclosed. Methods of using the Bcl-2/Bcl-xL inhibitors in the treatment of diseases and conditions wherein inhibition of Bcl-2/Bcl-xL provides a benefit, like cancers, also are disclosed.

18 Claims, No Drawings

US 9,096,625 B2

BCL-2/BCL-XL INHIBITORS AND THERAPEUTIC METHODS USING THE SAME

CROSS-REFERENCE TO RELATED APPLICATIONS

This application claims the benefit of U.S. Provisional Patent Application No. 61/753,066, filed Jan. 16, 2013, which is incorporated by reference herein in its entirety.

FIELD OF THE INVENTION

The present invention relates to Bcl-2/Bcl-xL inhibitors and to therapeutic methods of treating conditions and diseases wherein inhibition of Bcl-2/Bcl-xL provides a benefit.

BACKGROUND OF THE INVENTION

Apoptosis resistance is a hallmark of human cancer (1-3). Cancer cells must overcome a continual bombardment by cellular stresses, such as DNA damage, oncogene activation, aberrant cell cycle progression, and harsh microenvironments, that would cause normal cells to undergo apoptosis. One of the primary means by which cancer cells evade apoptosis is by up-regulation of anti-apoptotic proteins of the Bcl-2 family. Targeting key apoptosis regulators to overcome apoptosis-resistance and promote apoptosis of tumor cells is a new cancer therapeutic strategy (4,5).

Bcl-2 proteins function as critical regulators of apoptosis in both cancer and normal cells (6-10). Bcl-2 proteins serve as a check on apoptosis allowing healthy and useful cells to survive. This protein family includes anti-apoptotic proteins, such as Bcl-2, Bcl-xL, and Mcl-1, and pro-apoptotic molecules, including Bid, Bim, Bad, Bak and Bax (6-10). While normal cells have low expression levels of the anti-apoptotic Bcl-2 and Bcl-xL proteins, these proteins are found to be highly overexpressed in many different types of human tumors (6-10). This overexpression has been linked to poor prognosis in several types of cancer, and to clinical resistance to chemotherapeutic agents and radiation (6-10). Consistent with clinical observations, laboratory studies have established that overexpression of Bcl-2 or Bcl-xL causes cancer cells to become more resistant to chemotherapeutic agents in vitro and in vivo (6-10). Inhibition of apoptosis by Bcl-2 contributes to cancer by inhibiting cell death. Therefore, targeting Bcl-2 and/or Bcl-xL has been pursued as a cancer therapeutic strategy (11-34). Inhibiting Bcl-2 activity in cancer cells can reduce chemotherapeutic resistance and increase the killing of cancer cells.

Bcl-2 and Bcl-xL proteins inhibit apoptosis by heterodimerization with pro-apoptotic Bcl-2 family proteins, such as Bak, Bax, Bim, Bid, Puma, and Bad (6-10). Experimentally determined three-dimensional structures of Bcl-xL and Bcl-2 have shown that these proteins possess a well-defined groove, which interacts with the BH3 (Bcl-2 Homology 3) domain of the pro-apoptotic Bcl-2 proteins (38-42). It has been proposed that non-peptide small molecules designed to block the heterodimerization of Bcl-2/Bcl-xL proteins with their pro-death binding partners may be effective as antagonists of Bcl-2/Bcl-xL, and that such small molecule inhibitors may have a great therapeutic potential for the treatment of human cancers in which Bcl-2 and/or Bcl-xL are highly expressed (18-37).

Although non-peptide, small molecule inhibitors of Bcl-2/Bcl-xL have been reported, most of the inhibitors have weak to modest affinities for these proteins and lack a well-defined mode of action for their cellular activity (18-37). The exceptions are ABT-737, ABT-263, and their analogues (26-34). ABT-737 and ABT-263 bind to Bcl-2, Bcl-xL, and Bcl-w with very high affinities ($K_i$<1 nM) and have high specificity over Mcl-1 and A1, two other anti-apoptotic Bcl-2 proteins (26, 32, 34). ABT-263 has advanced into Phase I/II clinical trials and shows promising antitumor activity in the clinic (45).

Despite the discovery of ABT-737 and ABT-263, the design of potent, non-peptide inhibitors of Bcl-2/Bcl-xL remains a significant challenge in modern drug discovery. Accordingly, a need still exists in the art for Bcl-2/Bcl-xL inhibitors having physical and pharmacological properties that permit use of the inhibitors in therapeutic applications. The present invention provides compounds designed to bind to Bcl-2/Bcl-xL and inhibit Bcl-2/Bcl-xL activity.

SUMMARY OF THE INVENTION

The present invention is directed to inhibitors of Bcl-2/Bcl-xL, to compositions comprising the inhibitors, and to methods of using the inhibitors in a therapeutic treatment of conditions and diseases wherein inhibition of Bcl-2/Bcl-xL activity provides a benefit. The present compounds are potent inhibitors of Bcl-2/Bcl-xL activation, and induce apoptosis of cancer cells that express Bcl-2 and/or Bcl-xL.

More particularly, the present invention is directed to compounds having a structural formula (I), (II), or (III):

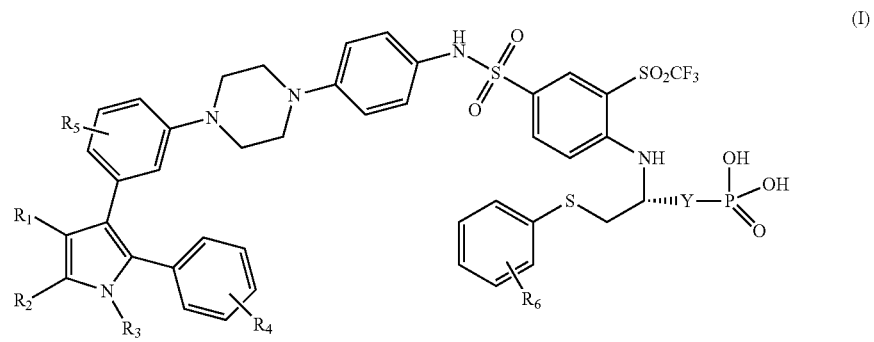

(I)

-continued

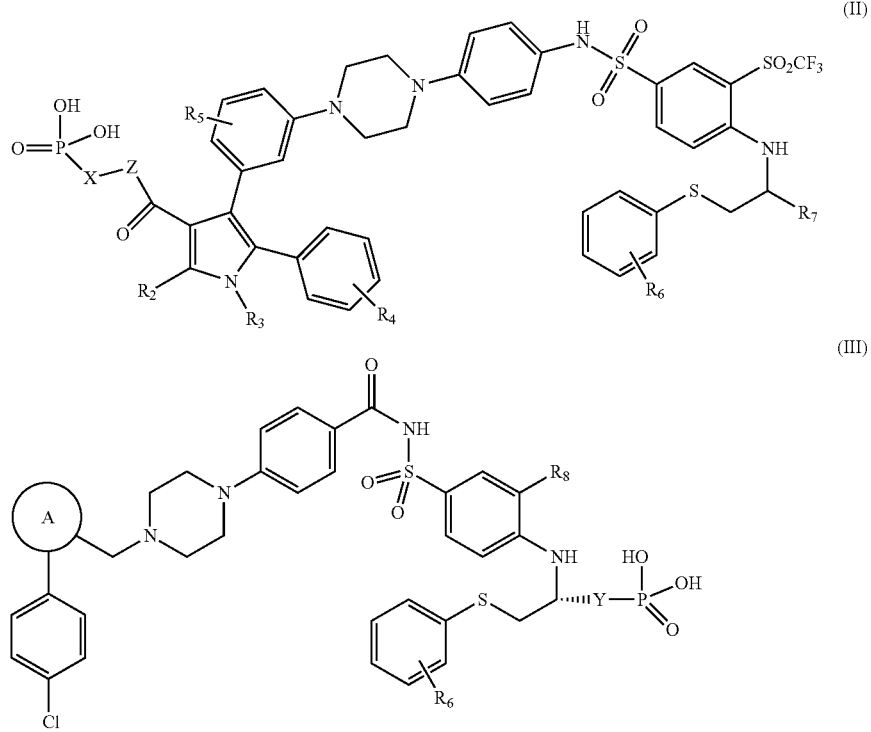

(II)

(III)

wherein the A ring is

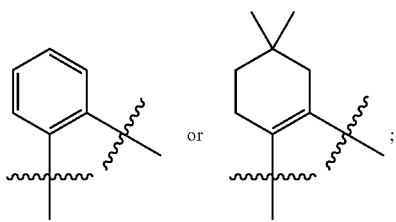

X, substituted or unsubstituted, is selected from the group consisting of alkylene, alkenylene, cycloalkylene, cycloalkenylene, and heterocycloalkylene;

Y is selected from the group consisting of $(CH_2)_n—N(R^a)_2$ and

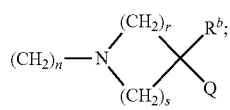

Q is selected from the group consisting of O, $O(CH_2)_{1-3}$, $NR^c$, $NR^c(C_{1-3}alkylene)$, $OC(=O)(C_{1-3}alkylene)$, $C(=O)O$, $C(=O)O(C_{1-3}alkylene)$, $NHC(=O)(C_{1-3}alkylene)$, $C(=O)NH$, and $C(=O)NH(C_{1-3}alkylene)$;

Z is O or $NR^c$;

$R_1$ and $R_2$, independently, are selected from the group consisting of H, CN, $NO_2$, halo, alkyl, cycloalkyl, alkenyl, cycloalkenyl, alkynyl, aryl, heteroaryl, heterocycloalkyl, OR', SW, NR'R", COW, $CO_2R'$, OCOR', CONR'R", CONR'SO$_2$R", NR'COR", NR'CONR"R'", NR'C=SNR"R'", NR'SO$_2$R", SO$_2$R', and SO$_2$NR'R";

$R_3$ is selected from a group consisting of H, alkyl, cycloalkyl, alkenyl, cycloalkenyl, alkynyl, aryl, heteroaryl, heterocycloalkyl, OR', NR'R", OCOR', $CO_2R'$, COW, CONR'R", CONR'SO$_2$R", $C_{1-3}$alkyleneCH(OH)CH$_2$OH, SO$_2$R', and SO$_2$NR'R";

R', R", and R'", independently, are H, alkyl, cycloalkyl, alkenyl, cycloalkenyl, alkynyl, aryl, heteroaryl, $C_{1-3}$alkyleneheterocycloalkyl, or heterocycloalkyl;

R' and R", or R" and R'", can be taken together with the atom to which they are bound to form a 3 to 7 membered ring;

$R_4$ is hydrogen, halo, $C_{1-3}$alkyl, $CF_3$, or CN;

$R_5$ is hydrogen, halo, $C_{1-3}$alkyl, substituted $C_{1-3}$alkyl, hydroxyalkyl, alkoxy, or substituted alkoxy;

$R_6$ is selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", $CO_2R'$, OCOR', CONR'R", CONR'SO$_2$R", NR'COR", NR'CONR"R'", NR'C=SNR"R'", NR'SO$_2$R", SO$_2$R', and SO$_2$NR'R";

$R_7$, substituted or unsubstituted, is selected form the group consisting of hydrogen, alkyl, alkenyl, $(CH_2)_{0-3}$cycloalkyl, $(CH_2)_{0-3}$cycloalkenyl, $(CH_2)_{0-3}$heterocycloalkyl, $(CH_2)_{0-3}$aryl, and $(CH_2)_{0-3}$heteroaryl;

$R_8$ is selected form the group consisting of hydrogen, halo, $NO_2$, CN, $CF_3SO_2$, and $CF_3$;

$R_a$ is selected from the group consisting of hydrogen, alkyl, heteroalkyl, alkenyl, hydroxyalkyl, alkoxy, substituted alkoxy, cycloalkyl, cycloalkenyl, and heterocycloalkyl;

$R_b$ is hydrogen or alkyl;

$R_c$ is selected from the group consisting of hydrogen, alkyl, substituted alkyl, hydroxyalkyl, alkoxy, and substituted alkoxy; and n, r, and s, independently, are 1, 2, 3, 4, 5, or 6;

or a pharmaceutically acceptable salt of (I), (II), or (III).

In some embodiments, $R_1$ and $R_2$ or $R_2$ and $R_3$ can be taken together to form a ring. In other embodiments, R' and R", or R'' and R''', can be taken together with the atoms to which they are bound to form a 3 to 7 membered ring.

In one embodiment, the present invention provides a method of treating a condition or disease by administering a therapeutically effective amount of a compound of structural formula (I), (II), or (III) to an individual in need thereof. The disease or condition of interest is treatable by inhibition of Bcl-2 and/or Bcl-xL, for example, a cancer.

Another embodiment of the present invention is to provide a composition comprising (a) a Bcl-2/Bcl-xL inhibitor of structural formula (I), (II), or (III) and (b) an excipient and/or pharmaceutically acceptable carrier useful in treating diseases or conditions wherein inhibition of Bcl-2/Bcl-xL provides a benefit.

Another embodiment of the present invention is to utilize a composition comprising a compound of structural formula (I), (II), or (III) and a second therapeutically active agent in a method of treating an individual for a disease or condition wherein inhibition of Bcl-2/Bcl-xL provides a benefit.

In a further embodiment, the invention provides for use of a composition comprising a Bcl-2/Bcl-xL inhibitor of structural formula (I), (II), or (III) and an optional second therapeutic agent for the manufacture of a medicament for treating a disease or condition of interest, e.g., a cancer.

Still another embodiment of the present invention is to provide a kit for human pharmaceutical use comprising (a) a container, (b1) a packaged composition comprising a Bcl-2/Bcl-xL inhibitor of structural formula (I), (II), or (III), and, optionally, (b2) a packaged composition comprising a second therapeutic agent useful in the treatment of a disease or condition of interest, and (c) a package insert containing directions for use of the composition or compositions, administered simultaneously or sequentially, in the treatment of the disease or condition.

The Bcl-2/Bcl-xL inhibitor of structural formula (I), (II), or (III) and the second therapeutic agent can be administered together as a single-unit dose or separately as multi-unit doses, wherein the Bcl-2/Bcl-xL inhibitor of structural formula (I), (II), or (III) is administered before the second therapeutic agent or vice versa. It is envisioned that one or more dose of a Bcl-2/Bcl-xL inhibitor of structural formula (I), (II), or (III) and/or one or more dose of a second therapeutic agent can be administered.

In one embodiment, a Bcl-2/Bcl-xL inhibitor of structural formula (I), (II), or (III) and a second therapeutic agent are administered simultaneously. In related embodiments, a Bcl-2/Bcl-xL inhibitor of structural formula (I), (II), or (III) and second therapeutic agent are administered from a single composition or from separate compositions. In a further embodiment, the Bcl-2/Bcl-xL inhibitor of structural formula (I), (II), or (III) and second therapeutic agent are administered sequentially. A Bcl-2/Bcl-xL inhibitor of structural formula (I), (II), or (III), as used in the present invention, can be administered in an amount of about 0.005 to about 500 milligrams per dose, about 0.05 to about 250 milligrams per dose, or about 0.5 to about 100 milligrams per dose.

These and other embodiments and features of the present invention will become apparent from the following detailed description of the preferred embodiments.

DETAILED DESCRIPTION OF THE PREFERRED EMBODIMENTS

The present invention is described in connection with preferred embodiments. However, it should be appreciated that the invention is not limited to the disclosed embodiments. It is understood that, given the description of the embodiments of the invention herein, various modifications can be made by a person skilled in the art. Such modifications are encompassed by the claims below.

The term "Bcl-2/Bcl-xL" as used herein means Bcl-2, Bcl-xL, or Bcl-2 and Bcl-xL, i.e., Bcl-2 and/or Bcl-xL.

The term "a disease or condition wherein inhibition of Bcl-2 and/or Bcl-xL provides a benefit" pertains to a condition in which Bcl-2 and/or Bcl-xL, and/or an action of Bcl-2 and/or Bcl-xL, is important or necessary, e.g., for the onset, progress, expression of that disease or condition, or a disease or a condition which is known to be treated by a Bcl-2/Bcl-xL inhibitor, such as ABT-737 or ABT-263. An example of such a condition includes, but is not limited to, a cancer. One of ordinary skill in the art is readily able to determine whether a compound treats a disease or condition mediated by Bcl-2/Bcl-xL for any particular cell type, for example, by assays which conveniently can be used to assess the activity of particular compounds.

The term "second therapeutic agent" refers to a therapeutic agent different from a Bcl-2 and/or Bcl-xL inhibitor of structural formula (I), (II), and (III) and that is known to treat the disease or condition of interest. For example when a cancer is the disease or condition of interest, the second therapeutic agent can be a known chemotherapeutic drug, like taxol, or radiation, for example.

The term "disease" or "condition" denotes disturbances and/or anomalies that as a rule are regarded as being pathological conditions or functions, and that can manifest themselves in the form of particular signs, symptoms, and/or malfunctions. As demonstrated below, compounds of structural formula (I), (II), and (III) are potent inhibitors of Bcl-2/Bcl-xL and can be used in treating diseases and conditions wherein inhibition of Bcl-2/Bcl-xL provides a benefit.

As used herein, the terms "treat," "treating," "treatment," and the like refer to eliminating, reducing, or ameliorating a disease or condition, and/or symptoms associated therewith. Although not precluded, treating a disease or condition does not require that the disease, condition, or symptoms associated therewith be completely eliminated. As used herein, the terms "treat," "treating," "treatment," and the like may include "prophylactic treatment," which refers to reducing the probability of redeveloping a disease or condition, or of a recurrence of a previously-controlled disease or condition, in a subject who does not have, but is at risk of or is susceptible to, redeveloping a disease or condition or a recurrence of the disease or condition. The term "treat" and synonyms contemplate administering a therapeutically effective amount of a compound of the invention to an individual in need of such treatment.

Within the meaning of the invention, "treatment" also includes relapse prophylaxis or phase prophylaxis, as well as the treatment of acute or chronic signs, symptoms and/or malfunctions. The treatment can be orientated symptomatically, for example, to suppress symptoms. It can be effected over a short period, be oriented over a medium term, or can be a long-term treatment, for example within the context of a maintenance therapy.

The term "therapeutically effective amount" or "effective dose" as used herein refers to an amount of the active ingredient(s) that is(are) sufficient, when administered by a method of the invention, to efficaciously deliver the active ingredient(s) for the treatment of condition or disease of interest to an individual in need thereof. In the case of a cancer or other proliferation disorder, the therapeutically effective amount of the agent may reduce (i.e., retard to some extent and preferably stop) unwanted cellular proliferation; reduce the number of cancer cells; reduce the tumor size; inhibit (i.e., retard to some extent and preferably stop) cancer cell infiltration into peripheral organs; inhibit (i.e., retard to some extent and preferably stop) tumor metastasis; inhibit, to some extent, tumor growth; reduce Bcl-2/Bcl-xL signaling in the target cells; and/or relieve, to some extent, one or more of the symptoms associated with the cancer. To the extent the administered compound or composition prevents growth and/or kills existing cancer cells, it may be cytostatic and/or cytotoxic.

The term "container" means any receptacle and closure therefor suitable for storing, shipping, dispensing, and/or handling a pharmaceutical product.

The term "insert" means information accompanying a pharmaceutical product that provides a description of how to administer the product, along with the safety and efficacy data required to allow the physician, pharmacist, and patient to make an informed decision regarding use of the product. The package insert generally is regarded as the "label" for a pharmaceutical product.

"Concurrent administration," "administered in combination," "simultaneous administration," and similar phrases mean that two or more agents are administered concurrently to the subject being treated. By "concurrently," it is meant that each agent is administered either simultaneously or sequentially in any order at different points in time. However, if not administered simultaneously, it is meant that they are administered to an individual in a sequence and sufficiently close in time so as to provide the desired therapeutic effect and can act in concert. For example, a Bcl-2/Bcl-xL inhibitor of structural formula (I), (II), or (III) can be administered at the same time or sequentially in any order at different points in time as a second therapeutic agent. A present Bcl-2/Bcl-xL inhibitor and the second therapeutic agent can be administered separately, in any appropriate form and by any suitable route. When a present Bcl-2/Bcl-xL inhibitor and the second therapeutic agent are not administered concurrently, it is understood that they can be administered in any order to a subject in need thereof. For example, a present Bcl-2/Bcl-xL inhibitor can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent treatment modality (e.g., radiotherapy), to an individual in need thereof. In various embodiments, a Bcl-2/Bcl-xL inhibitor of structural formula (I) and the second therapeutic agent are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the components of the combination therapies are administered at 1 minute to 24 hours apart.

The use of the terms "a", "an", "the", and similar referents in the context of describing the invention (especially in the context of the claims) are to be construed to cover both the singular and the plural, unless otherwise indicated. Recitation of ranges of values herein are intended to merely serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended to better illustrate the invention and is not a limitation on the scope of the invention unless otherwise claimed. No language in the specification should be construed as indicating any non-claimed element as essential to the practice of the invention.

Over the past decade, research into apoptosis has established that targeting Bcl-2 and/or Bcl-xL using small molecule inhibitors is a viable cancer therapeutic strategy (35-37). The discovery of ABT-737 and ABT-263, and the early clinical data on ABT-263, have demonstrated that non-peptide, small molecule inhibitors of Bcl-2 and/or Bcl-xL have great therapeutic potential for the treatment of many types of human cancer in which Bcl-2 and/or Bcl-xL are overexpressed and for which current anticancer agents are largely ineffective (26-36).

Despite the discovery of ABT-737 and ABT-263, few new classes of highly potent, small molecule inhibitors of Bcl-2/Bcl-xL with affinities to Bcl-2/Bcl-xL and cellular potencies approaching that achieved by ABT-737/ABT-263 have been reported. This is because the design of small molecule inhibitors of Bcl-2/Bcl-xL involves targeting and blocking the interactions of the Bcl-2/Bcl-xL proteins with their pro-apoptotic binding partners, a task which has been proven to be very challenging for at least three main reasons. First, compared to typical binding sites in enzymes and receptors, the interfaces between Bcl-2 or Bcl-xL and their binding partners are very large (38-42). The interaction of Bcl-2/Bcl-xL with its binding partners, such as BAD and Bim proteins, is mediated by a 20-25 residue BH3 domain in BAD and Bim and a large binding groove in Bcl-2/Bcl-xL. Second, the binding grooves in Bcl-2/Bcl-xL are very hydrophobic in nature, making it difficult to design druglike small molecules (26, 38-42). Third, Bcl-2 and Bcl-xL are extremely conformationally flexible and can adopt quite distinct conformations in the ligand-free structure and when bound to different ligands (26, 38-42). Some of the binding pockets observed for Bcl-xL in the crystal structures of its complexes with BAD (41), Bim (43), and ABT-737(44) are induced by ligand binding and are not presented in a ligand-free crystal structure (38). These three factors make the design of potent and druglike small molecule inhibitors of Bcl-2/Bcl-xL a paramount challenge in modern drug discovery.

The present invention is directed to new class of potent and specific inhibitors of Bcl-2/Bcl-xL. The present compounds can bind to Bcl-2 and/or Bcl-xL with $K_i$ values <10 nM and function as potent antagonists of Bcl-2 and Bcl-xL in cell-free functional assays. The compounds potently induce apoptosis in cancer cells and have a mechanism of action that is highly consistent with targeting Bcl-2 and Bcl-xL. A tested compound demonstrates robust apoptosis induction in vivo in tumor tissues and shows strong antitumor activity against the H146 xenograft tumors.

The Bcl-2/Bcl-xL inhibitors of the present invention therefore are useful in the treatment of unwanted proliferating cells, including cancers and precancers, in subjects in need of such treatment. Also provided are methods of treating a subject having unwanted proliferating cells comprising administering a therapeutically effective amount of a present compound to a subject in need of such treatment. Also provided are methods of preventing the proliferation of unwanted proliferating cells, such as cancers and precancers, in a subject comprising the step of administering a therapeutically effective amount of a compound of structural formula (I) to a subject at risk of developing a condition characterized by unwanted proliferating cells. In some embodiments, the compounds of structural formula (I), (II), and (III) reduced the proliferation of unwanted cells by inducing apoptosis in those cells.

The present invention is directed to Bcl-2/Bcl-xL inhibitors having a structural formula (I), (II), or (III):

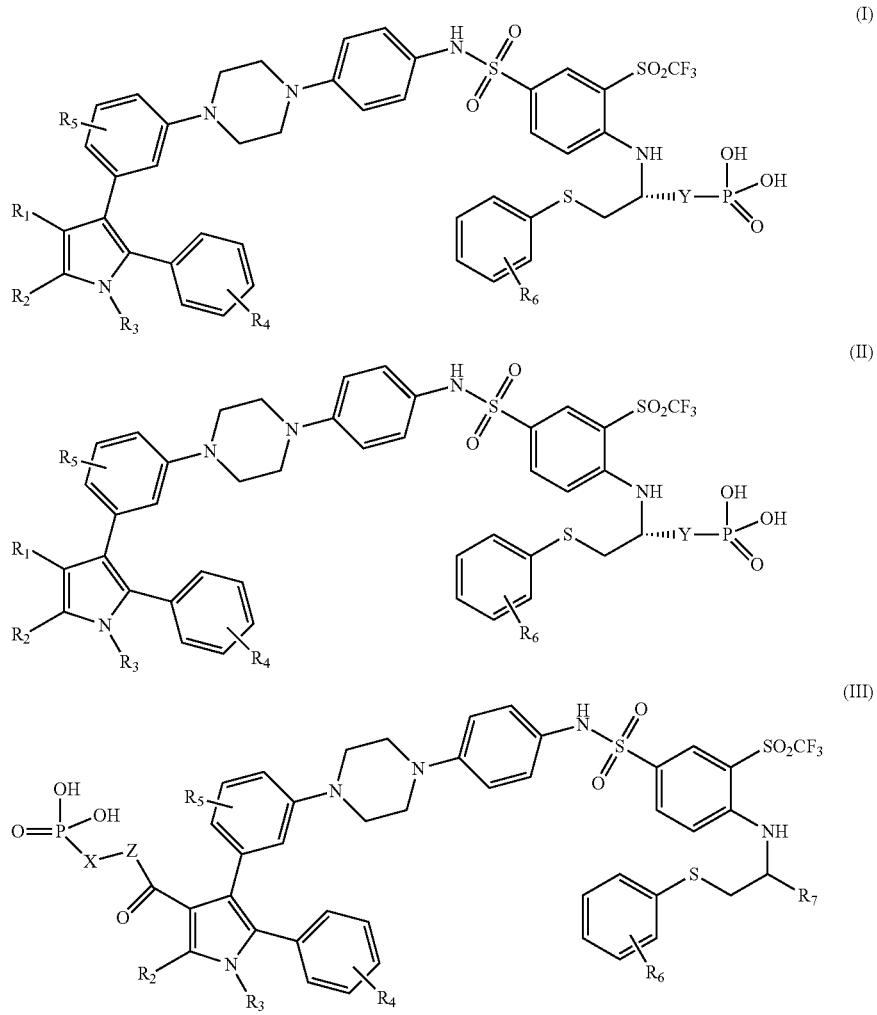

wherein the A ring is

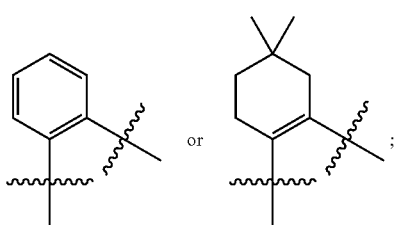

X, substituted or unsubstituted, is selected from the group consisting of alkylene, alkenylene, cycloalkylene, cycloalkenylene, and heterocycloalkylene;

Y is selected from the group consisting of $(CH_2)_n$—$N(R^a)_2$ and

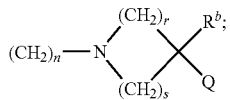

Q is selected from the group consisting of O, $O(CH_2)_{1-3}$, $NR^c$, $NR^c(C_{1-3}alkylene)$, $OC(=O)(C_{1-3}alkylene)$, $C(=O)O$, $C(=O)O(C_{1-3}alkylene)$, $NHC(=O)(C_{1-3}alkylene)$, $C(=O)NH$, and $C(=O)NH(C_{1-3}alkylene)$;

Z is O or $NR^c$;

$R_1$ and $R_2$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", COR', $CO_2R'$, OCOR', CONR'R", CONR'$SO_2R''$, NR'COR", NR'CONR"R''', NR'C=SNR"R''', NR'$SO_2R''$, $SO_2R'$, and $SO_2NR'R''$;

$R_3$ is selected from a group consisting of H, alkyl, cycloalkyl, alkenyl, cycloalkenyl, alkynyl, aryl, heteroaryl, heterocycloalkyl, OR', NR'R", OCOR', CO$_2$R', COR', CONR'R", CONR'SO$_2$R", C$_{1-3}$ alkyleneCH(OH)CH$_2$OH, SO$_2$R', and SO$_2$NR'R";

R', R", and R''', independently, are H, alkyl, cycloalkyl, alkenyl, cycloalkenyl, alkynyl, aryl, heteroaryl, C$_{1-3}$alkyleneheterocycloalkyl, or heterocycloalkyl;

R' and R", or R" and R''', can be taken together with the atom to which they are bound to form a 3 to 7 membered ring;

R$_4$ is hydrogen, halo, C$_{1-3}$alkyl, CF$_3$, or CN;

R$_5$ is hydrogen, halo, C$_{1-3}$alkyl, substituted C$_{1-3}$alkyl, hydroxyalkyl, alkoxy, or substituted alkoxy;

R$_6$ is selected from the group consisting of H, CN, NO$_2$, halo, alkyl, cycloalkyl, alkenyl, cycloalkenyl, alkynyl, aryl, heteroaryl, heterocycloalkyl, OR', SR', NR'R", CO$_2$R', OCOR', CONR'R", CONR'SO$_2$R", NR'COR", NR'CONR"R''', NR'C=SNR"R''', NR'SO$_2$R", SO$_2$R', and SO$_2$NR'R";

R$_7$, substituted or unsubstituted, is selected form the group consisting of hydrogen, alkyl, alkenyl, (CH$_2$)$_{0-3}$cycloalkyl, (CH$_2$)$_{0-3}$cycloalkenyl, (CH$_2$)$_{0-3}$heterocycloalkyl, (CH$_2$)$_{0-3}$aryl, and (CH$_2$)$_{0-3}$heteroaryl;

R$_8$ is selected form the group consisting of hydrogen, halo, NO$_2$, CN, CF$_3$SO$_2$, and CF$_3$;

R$_a$ is selected from the group consisting of hydrogen, alkyl, heteroalkyl, alkenyl, hydroxyalkyl, alkoxy, substituted alkoxy, cycloalkyl, cycloalkenyl, and heterocycloalkyl;

R$_b$ is hydrogen or alkyl;

R$^c$ is selected from the group consisting of hydrogen, alkyl, substituted alkyl, hydroxyalkyl, alkoxy, and substituted alkoxy; and n, r, and s, independently, are 1, 2, 3, 4, 5, or 6;

or a pharmaceutically acceptable salt of (I), (II), or (III).

The compounds of structural formula (I), (II), and (III) inhibit Bcl-2/Bcl-xL and are useful in the treatment of a variety of diseases and conditions. In particular, the compounds of structural formula (I), (II), and (III) are used in methods of treating a disease or condition wherein inhibition of Bcl-2/Bcl-xL provides a benefit, for example, cancers. The method comprises administering a therapeutically effective amount of a compound of structural formula (I), (II), or (III) to an individual in need thereof. The present methods also encompass administering a second therapeutic agent to the individual in addition to the compound of structural formula (I), (II), or (III). The second therapeutic agent is selected from drugs known as useful in treating the disease or condition afflicting the individual in need thereof, e.g., a chemotherapeutic agent and/or radiation known as useful in treating a particular cancer.

As used herein, the term "alkyl" refers to straight chained and branched saturated C$_{1-10}$ hydrocarbon groups, nonlimiting examples of which include methyl, ethyl, and straight chain and branched propyl, butyl, pentyl, hexyl, heptyl, octyl, nonyl, and decyl groups. The term C$_n$ means the alkyl group has "n" carbon atoms. The term C$_{n-p}$ means that the alkyl group contains "n" to "p" carbon atoms. The term "alkylene" refers to an alkyl group having a substituent. An alkyl, e.g., methyl, or alkylene, e.g., —CH$_2$—, group can be unsubstituted or substituted with halo, trifluoromethyl, trifluoromethoxy, hydroxy, alkoxy, nitro, cyano, alkylamino, or amino groups, for example.

The term "alkenyl" is defined identically as "alkyl," except for containing a carbon-carbon double bond, e.g., ethenyl, propenyl, and butenyl. The term "alkenylene" is defined identically to "alkylene" except for containing a carbon-carbon double bond. The term "alkynyl" and "alkynylene" are defined identically as "alkyl" and "alkylene" except the group contains a carbon-carbon triple bond.

As used herein, the term "halo" is defined as fluoro, chloro, bromo, and iodo.

The term "hydroxy" is defined as —OH.

The term "alkoxy" is defined as —OR, wherein R is alkyl.

The term "amino" is defined as —NH$_2$, and the term "alkylamino" is defined as —NR$_2$, wherein at least one R is alkyl and the second R is alkyl or hydrogen.

The term "nitro" is defined as —NO$_2$.

The term "cyano" is defined as —CN.

The term "trifluoromethyl" is defined as —CF$_3$.

The term "trifluoromethoxy" is defined as —OCF$_3$.

As used herein, groups such as

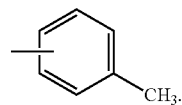

is an abbreviation for

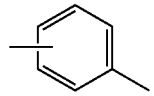

As used herein, the term "aryl" refers to a monocyclic or polycyclic aromatic group, preferably a monocyclic or bicyclic aromatic group, e.g., phenyl or naphthyl. Unless otherwise indicated, an aryl group can be unsubstituted or substituted with one or more, and in particular one to four, groups independently selected from, for example, halo, alkyl, alkenyl, —OCF$_3$, —CF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "heteroaryl" refers to a monocyclic or bicyclic ring system containing one or two aromatic rings and containing at least one nitrogen, oxygen, or sulfur atom in an aromatic ring. Unless otherwise indicated, a heteroaryl group can be unsubstituted or substituted with one or more, and in particular one to four, substituents selected from, for example, halo, alkyl, alkenyl, —OCF$_3$, —CF$_3$, —NO$_2$, —CN, —NC, —OH, alkoxy, amino, alkylamino, —CO$_2$H, —CO$_2$alkyl, —OCOalkyl, aryl, and heteroaryl.

As used herein, the term "cycloalkyl" means a monocyclic aliphatic ring containing three to eight carbon atoms. The term "heterocycloalkyl" means a monocyclic or bicyclic ring system containing at least one nitrogen, oxygen, or sulfur atom in the ring system. The terms "heteroaryl" and "heterocycloalkyl" encompass ring systems containing at least one oxygen atom, nitrogen atom, or sulfur atom, and includes ring systems containing oxygen and nitrogen atoms, oxygen and sulfur atoms, nitrogen and sulfur atoms, and nitrogen, oxygen, and sulfur atoms.

In some preferred embodiments, X is alkylene, and in preferred embodiments, is $C_{1-3}$alkylene.

In some embodiments, Y is

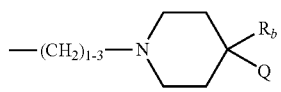

In preferred embodiments, n is 2. In other preferred embodiments, $R_b$ is hydrogen or $C_{1-3}$alkyl.

In still other preferred embodiments, Q is O, $O(CH_2)_{1-3}$, $C(=O)O(CH_2)_{1-3}$, $OC(=O)(CH_2)_{1-3}$, or $C(=O)O(C_3H_7)_{1-3}$. In some embodiments, Q is O, $OCH_2$, $C(=O)OCH_2$, $C(=O)O(CH_2)_2$, $C(=O)O(CH_2)_3$, $OC(=O)CH_2$, or $C(=O)O(CH(CH_3)CH_2)$.

In some embodiments, Z is O, NH, or $N(C_{1-3}alkyl)$. In preferred embodiments, Z is O, NH, or $NCH_3$.

In some embodiments, $R_1$ is $SO_2R'$, $SO_2NR'R''$, $NR'SOR''$, H, or alkyl. In some preferred embodiments, $R_1$ is $SO_2(C_{1-3}alkyl)$, $SO_2N(C_{1-3}alkyl)_2$, $NHSO_2(C_{1-3}alkyl)$, H, or $C_{1-3}alkyl$. One preferred embodiment of $R_1$ is $SO_2CH_3$.

In some embodiments, $R_2$ and $R_3$, independently, are H, $C_{1-3}alkyl$, or cycloalkyl. $R_2$ also can be halo. In some preferred embodiments, $R_2$ and $R_3$, independently, are methyl, ethyl, n-propyl, isopropyl, cyclopentyl, or cyclohexyl. $R_2$ also can be Cl or F.

In some embodiments, $R_4$ is H, Cl, or F. In other embodiments, $R_5$ is H, methyl, ethyl, n-propyl, isopropyl, F, or Cl. In other embodiments, $R_6$ is H, halo, alkyl, or cycloalkyl. In some preferred embodiments, $R_6$ is H, F, Cl, $C_{1-3}alkyl$, cyclopentyl, or cyclohexyl.

In some embodiments, $R_7$ is $(CH_2)_{0-3}$cycloalkyl or $(CH_2)_{0-3}$heterocycloalkyl. In a preferred embodiment, $R_7$ is $(CH_2)_{0-3}$cycloalkyl, optionally substituted with —OH. In one embodiment, $R_7$ is

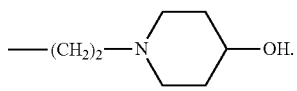

In some embodiments, $R_8$ is $CFSO_2$ or $CF_3$. In various embodiments, $R_a$, $R_b$, and $R_c$, independently, are H or $C_{1-3}alkyl$.

Additionally, salts, hydrates, and solvates of the present compounds also are included in the present invention and can be used in the methods disclosed herein. The present invention further includes all possible stereoisomers and geometric isomers of the compounds of structural formula (I), (II), and (III). The present invention includes both racemic compounds and optically active isomers. When a compound of structural formula (I), (II), or (III) is desired as a single enantiomer, it can be obtained either by resolution of the final product or by stereospecific synthesis from either isomerically pure starting material or use of a chiral auxiliary reagent, for example, see Z. Ma et al., *Tetrahedron: Asymmetry*, 8(6), pages 883-888 (1997). Resolution of the final product, an intermediate, or a starting material can be achieved by any suitable method known in the art. Additionally, in situations where tautomers of the compounds of structural formula (I), (II), or (III) are possible, the present invention is intended to include all tautomeric forms of the compounds.

Compounds of the invention can exist as salts. Pharmaceutically acceptable salts of the compounds of the invention often are preferred in the methods of the invention. As used herein, the term "pharmaceutically acceptable salts" refers to salts or zwitterionic forms of the compounds of structural formula (I), (II), and (III). Salts of compounds of formula (I), (II), and (III) can be prepared during the final isolation and purification of the compounds or separately by reacting the compound with an acid having a suitable cation. The pharmaceutically acceptable salts of compounds of structural formula (I), (II), and (III) can be acid addition salts formed with pharmaceutically acceptable acids. Examples of acids which can be employed to form pharmaceutically acceptable salts include inorganic acids such as nitric, boric, hydrochloric, hydrobromic, sulfuric, and phosphoric, and organic acids such as oxalic, maleic, succinic, and citric. Nonlimiting examples of salts of compounds of the invention include, but are not limited to, the hydrochloride, hydrobromide, hydroiodide, sulfate, bisulfate, 2-hydroxyethansulfonate, phosphate, hydrogen phosphate, acetate, adipate, alginate, aspartate, benzoate, bisulfate, butyrate, camphorate, camphorsulfonate, digluconate, glycerolphsphate, hemisulfate, heptanoate, hexanoate, formate, succinate, fumarate, maleate, ascorbate, isethionate, salicylate, methanesulfonate, mesitylenesulfonate, naphthylenesulfonate, nicotinate, 2-naphthalenesulfonate, oxalate, pamoate, pectinate, persulfate, 3-phenylproprionate, picrate, pivalate, propionate, trichloroacetate, trifluoroacetate, phosphate, glutamate, bicarbonate, paratoluenesulfonate, undecanoate, lactate, citrate, tartrate, gluconate, methanesulfonate, ethanedisulfonate, benzene sulphonate, and p-toluenesulfonate salts. In addition, available amino groups present in the compounds of the invention can be quaternized with methyl, ethyl, propyl, and butyl chlorides, bromides, and iodides; dimethyl, diethyl, dibutyl, and diamyl sulfates; decyl, lauryl, myristyl, and steryl chlorides, bromides, and iodides; and benzyl and phenethyl bromides. In light of the foregoing, any reference to compounds of the present invention appearing herein is intended to include compounds of structural formula (I), (II), and (III), as well as pharmaceutically acceptable salts, hydrates, or solvates thereof.

Specific compounds of the present invention include, but are not limited to, compounds having the structure set forth below.

| Compound No. | Structure |
|---|---|
| 1 | *(chemical structure)* |
| 2 | *(chemical structure)* |

-continued
| Compound No. | Structure |
|---|---|
| 3 | 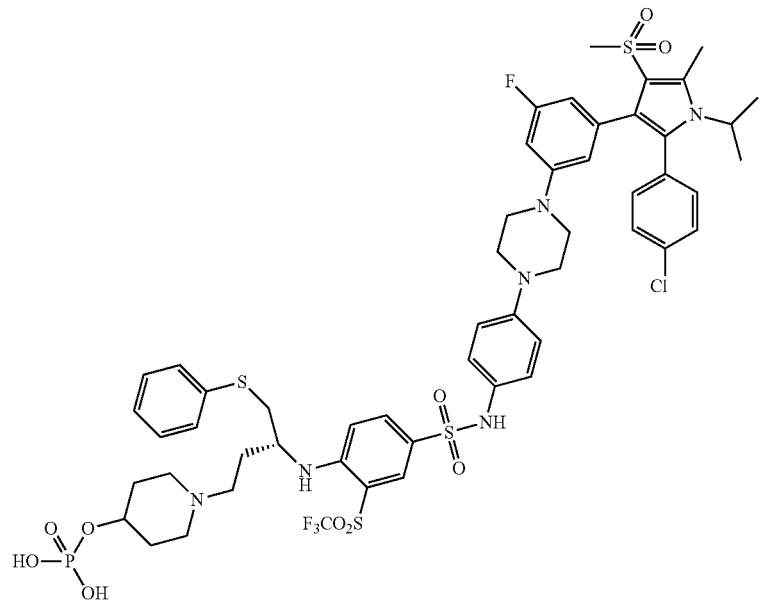 |
| 4 | 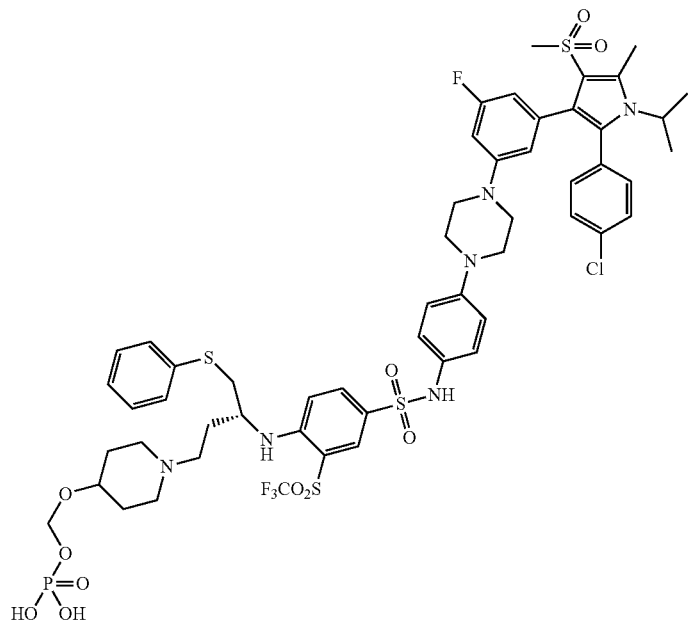 |

-continued
| Compound No. | Structure |
|---|---|
| 5 | 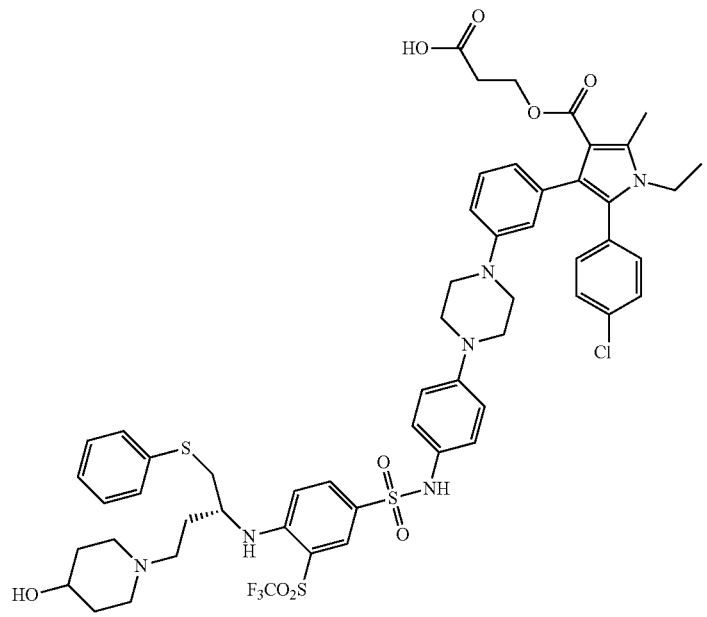 |
| 6 | 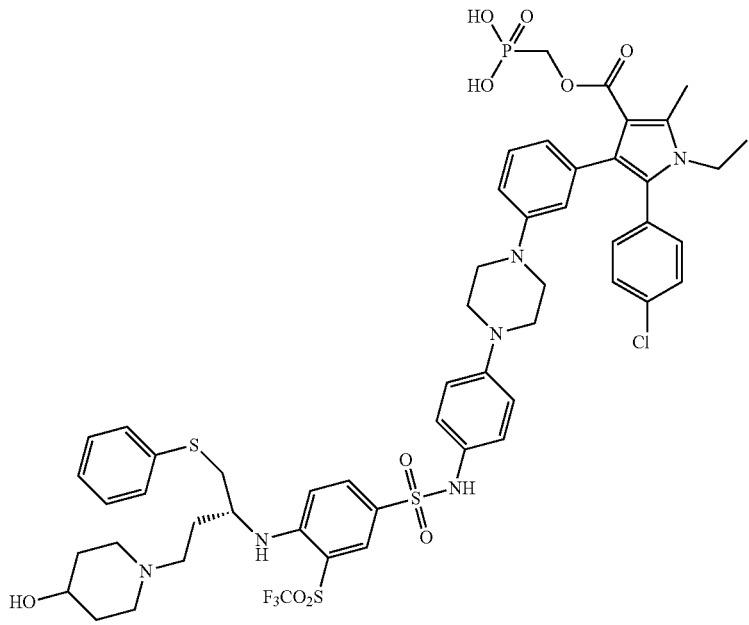 |

-continued
| Compound No. | Structure |
|---|---|
| 7 | 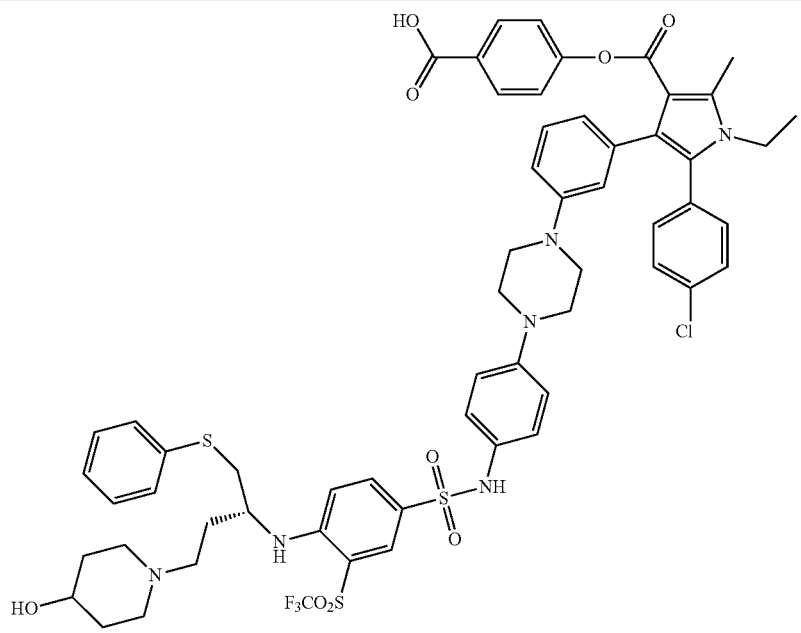 |
| 8 | 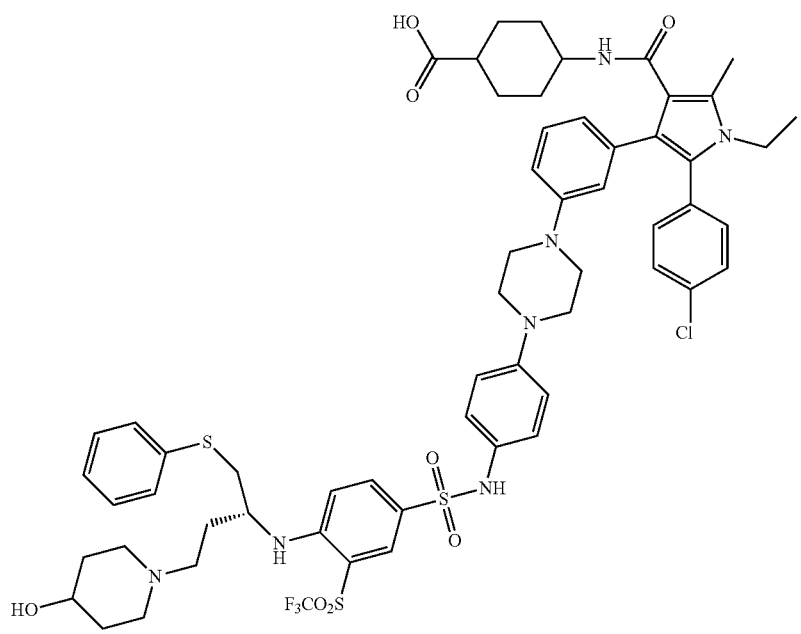 |

| Compound No. | Structure |
|---|---|
| 9 | 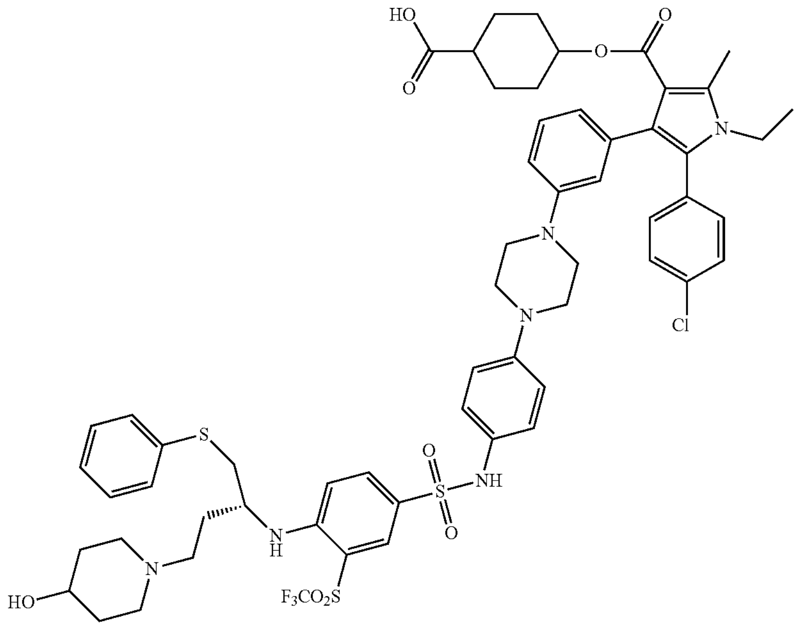 |
| 10 | 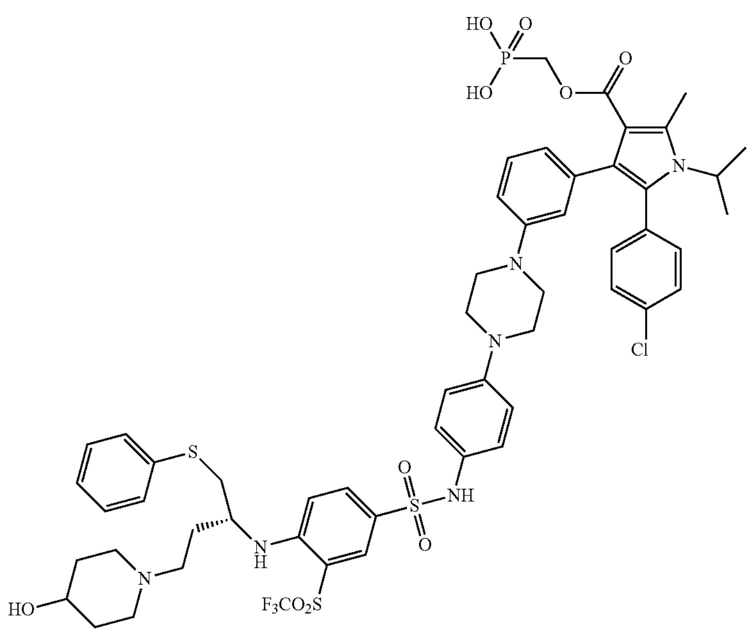 |

| Compound No. | Structure |
|---|---|
| 11 | 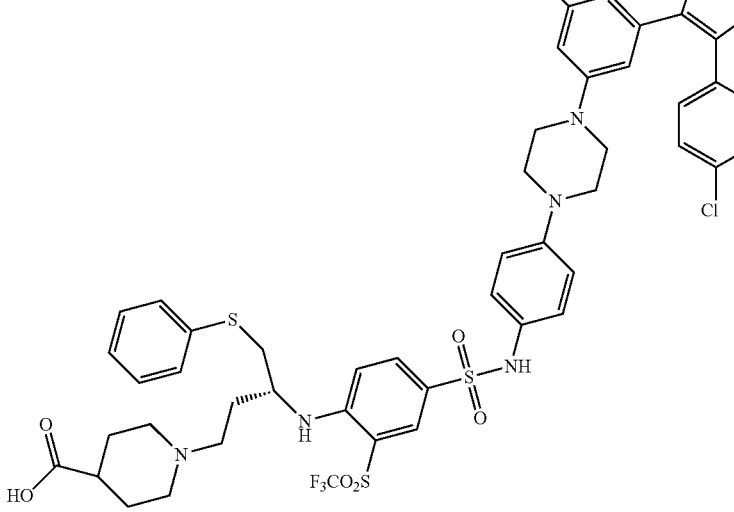 |
| 12 | 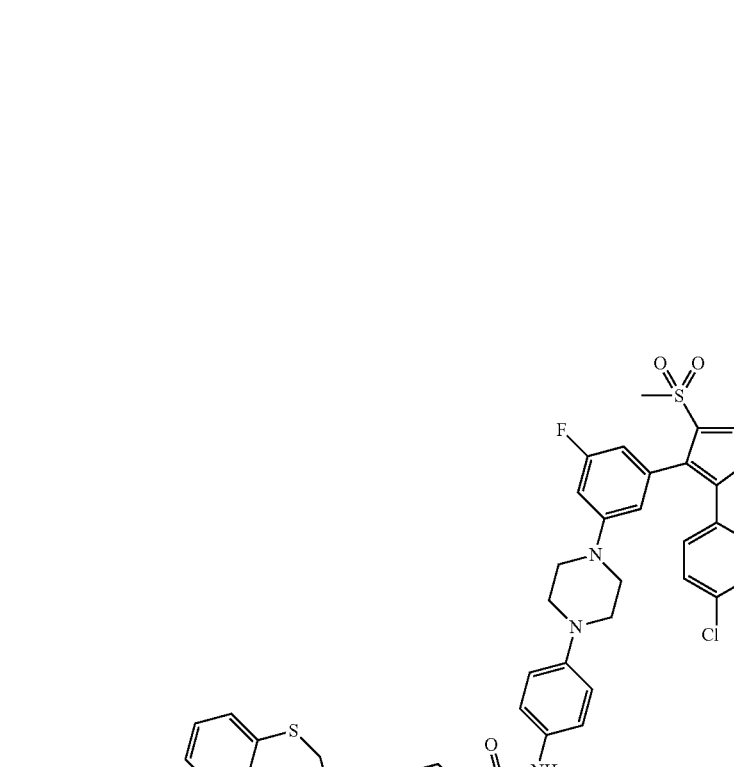 |

| Compound No. | Structure |
|---|---|
| 13 | 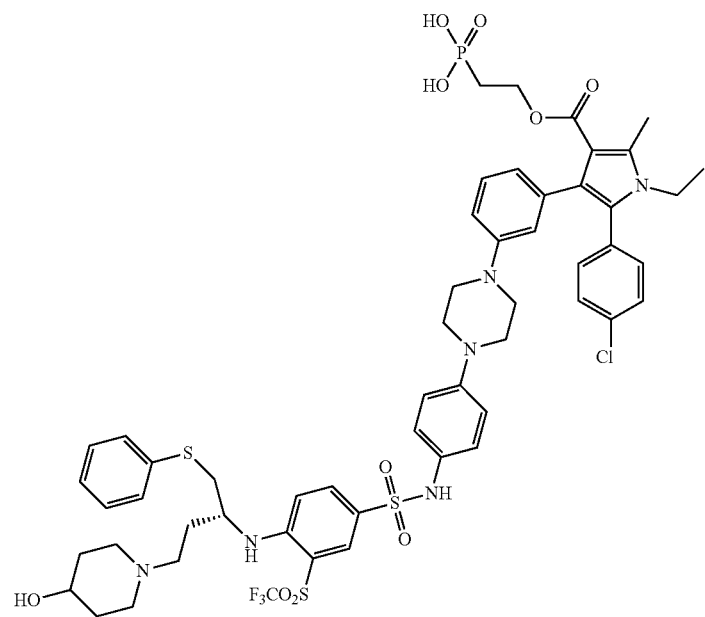 |
| 14 | 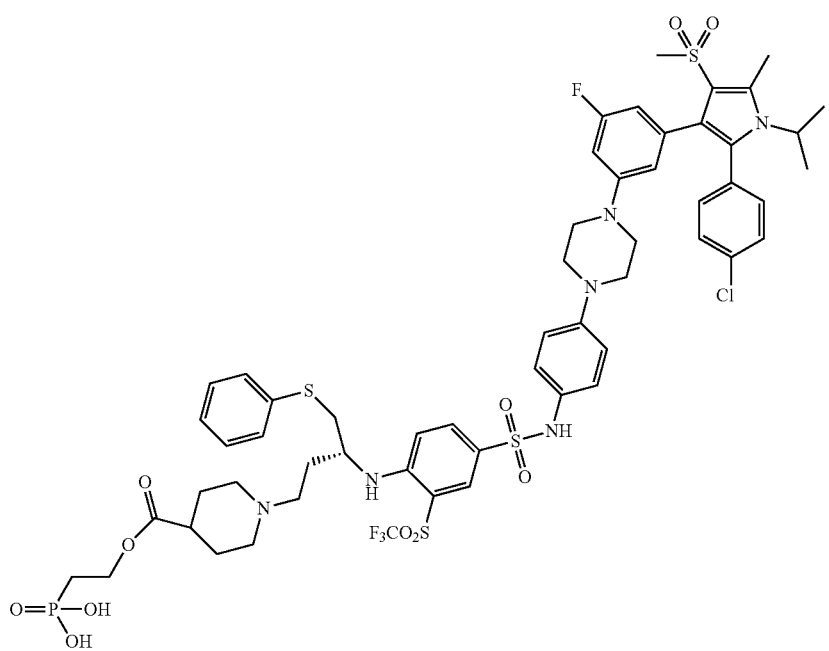 |

-continued
| Compound No. | Structure |
|---|---|
| 15 | 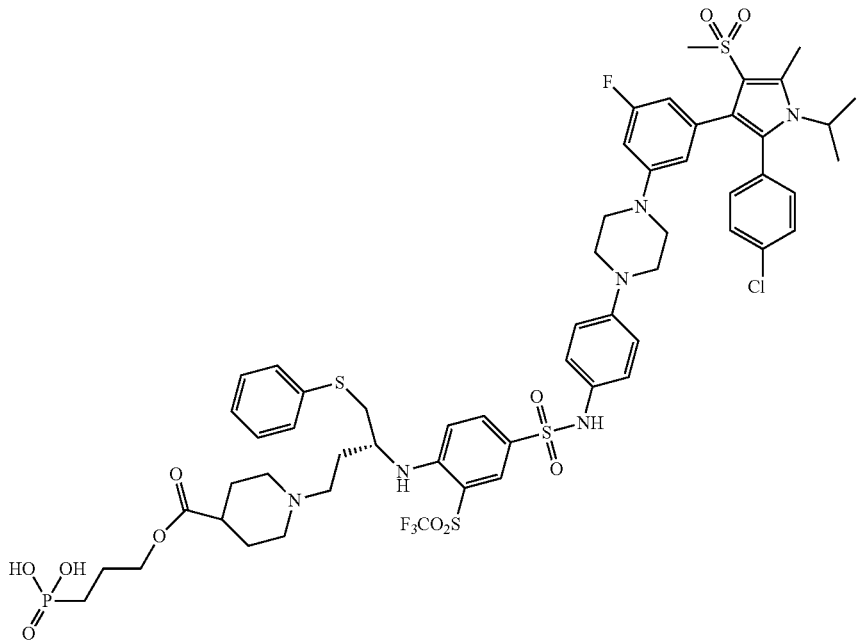 |
| 16 | 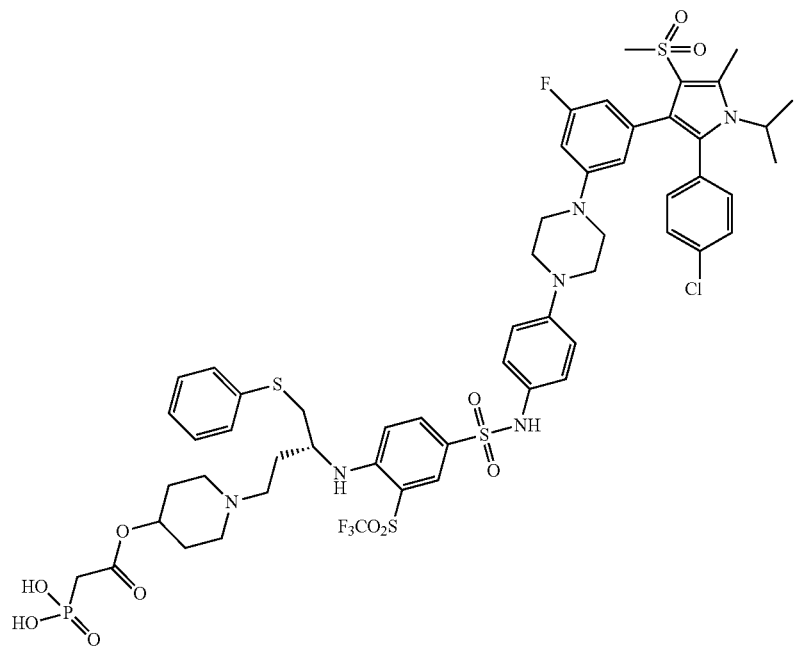 |

| Compound No. | Structure |
|---|---|
| 17 | 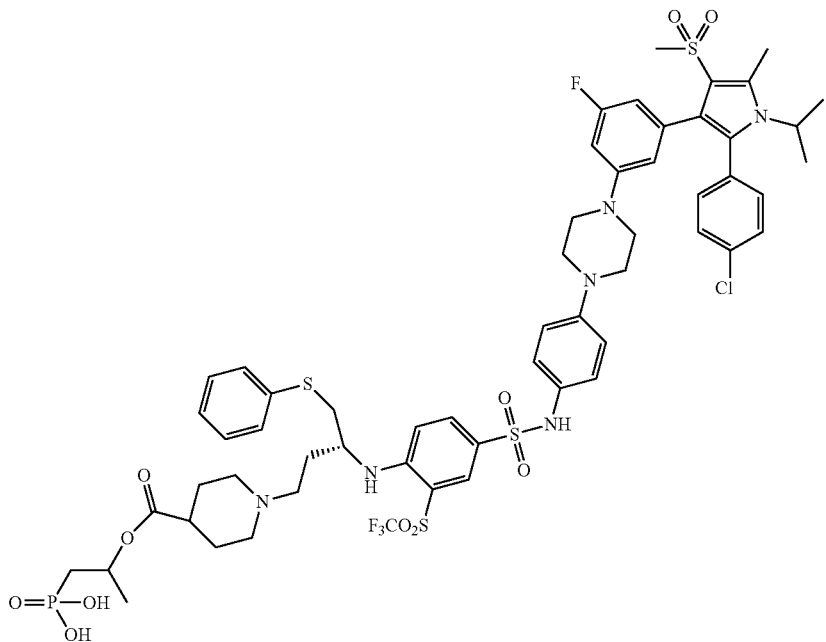 |
| 18 | 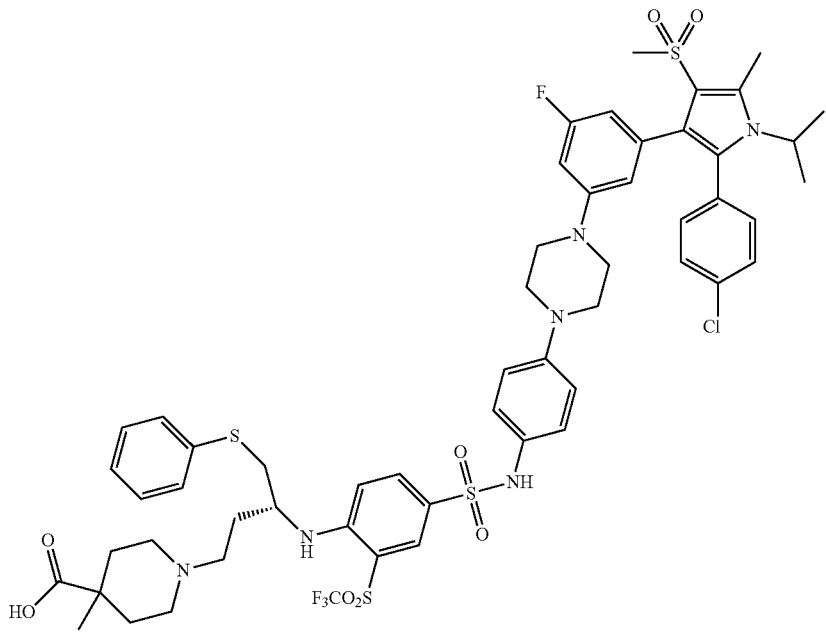 |

| Compound No. | Structure |
|---|---|
| 19 | 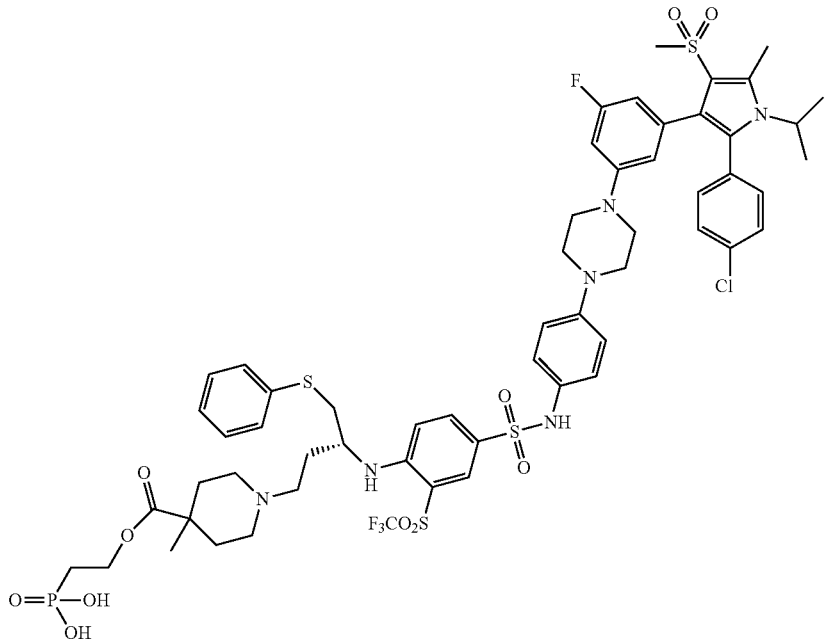 |
| 20 | 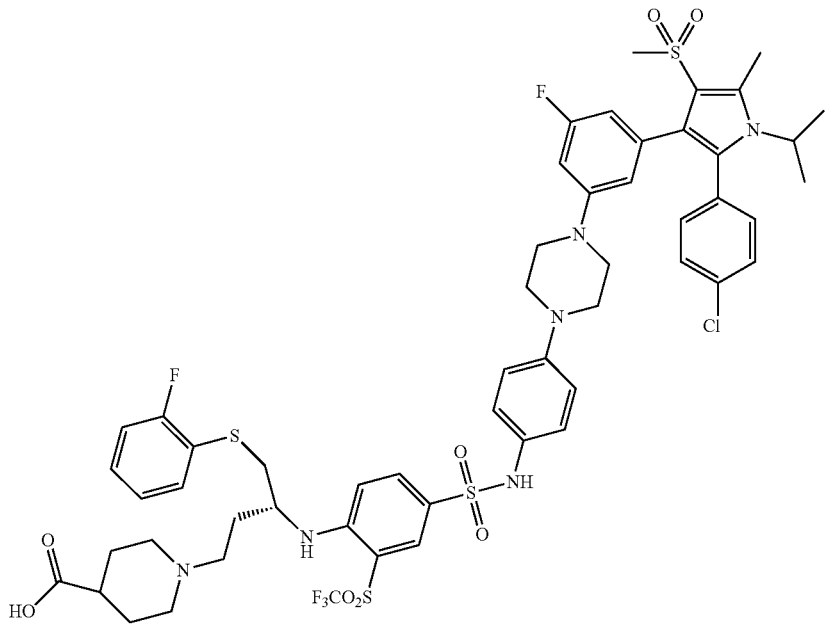 |

-continued
| Compound No. | Structure |
|---|---|
| 21 | 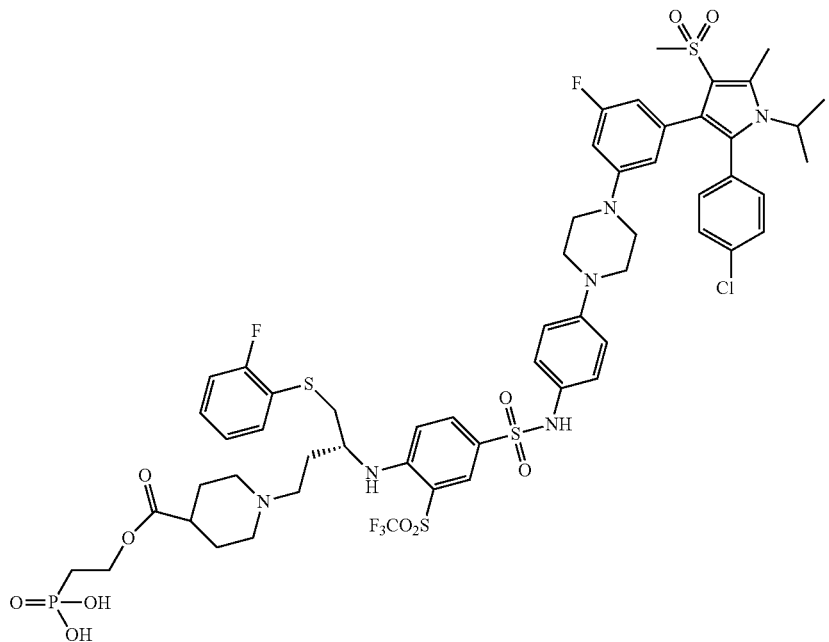 |
| 22 | 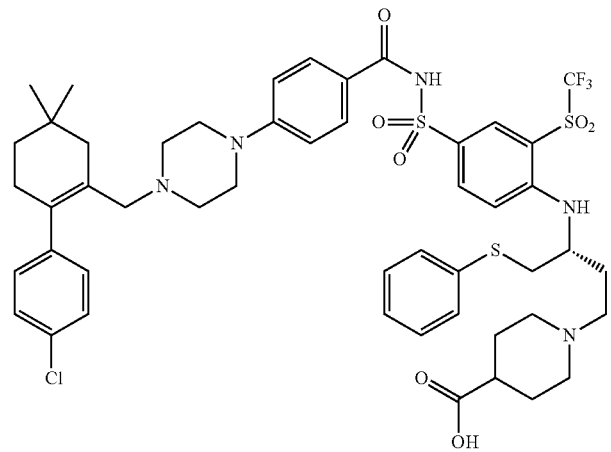 [SMILES: CC1(C)CCC(c2ccc(Cl)cc2)=C(CN2CCN(c3ccc(C(=O)NS(=O)(=O)c4ccc(N[C@H](CCN5CCC(C(=O)O)CC5)CSc5ccccc5)c(S(=O)(=O)C(F)(F)F)c4)cc3)CC2)C1] |

| Compound No. | Structure |
|---|---|
| 23 | 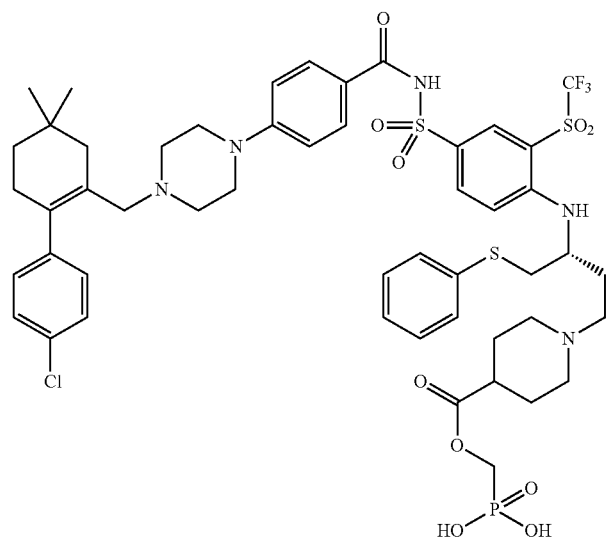 [SMILES: CC1(C)CCC(c2ccc(Cl)cc2)=C(CN2CCN(c3ccc(C(=O)NS(=O)(=O)c4ccc(N[C@H](CCN5CCC(C(=O)OCP(=O)(O)O)CC5)CSc5ccccc5)c(S(=O)(=O)C(F)(F)F)c4)cc3)CC2)C1] |
| 24 | 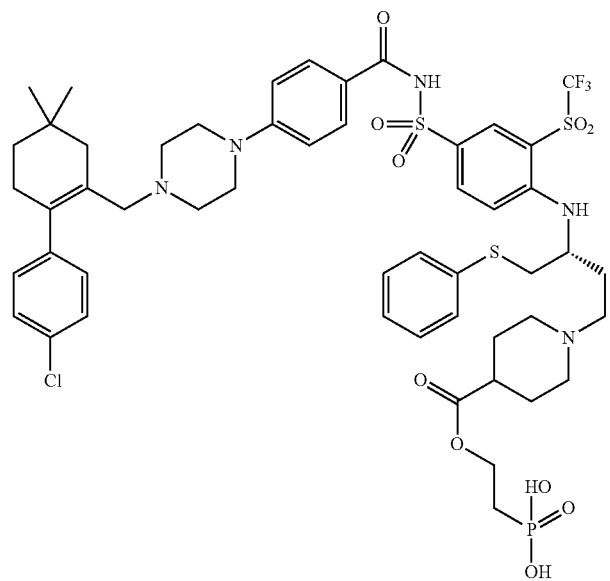 [SMILES: CC1(C)CCC(c2ccc(Cl)cc2)=C(CN2CCN(c3ccc(C(=O)NS(=O)(=O)c4ccc(N[C@H](CCN5CCC(C(=O)OCCP(=O)(O)O)CC5)CSc5ccccc5)c(S(=O)(=O)C(F)(F)F)c4)cc3)CC2)C1] |

-continued

| Compound No. | Structure |
|---|---|
| 25 | 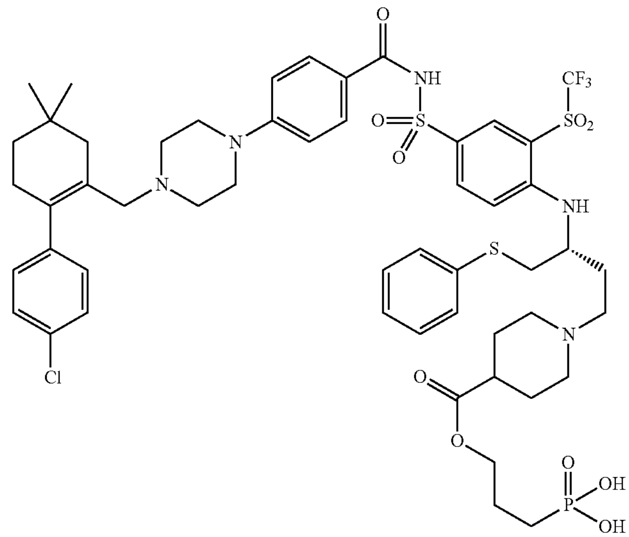 [SMILES: CC1(C)CCC(c2ccc(Cl)cc2)=C(CN2CCN(c3ccc(C(=O)NS(=O)(=O)c4ccc(N[C@H](CCN5CCC(C(=O)OCCCP(=O)(O)O)CC5)CSc5ccccc5)c(S(=O)(=O)C(F)(F)F)c4)cc3)CC2)C1] |
| 26 | 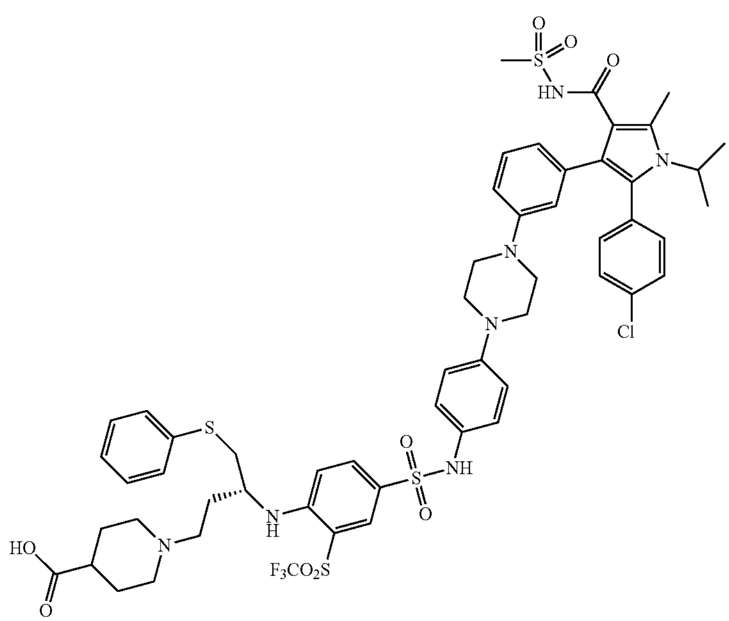 |

| Compound No. | Structure |
|---|---|
| 27 | 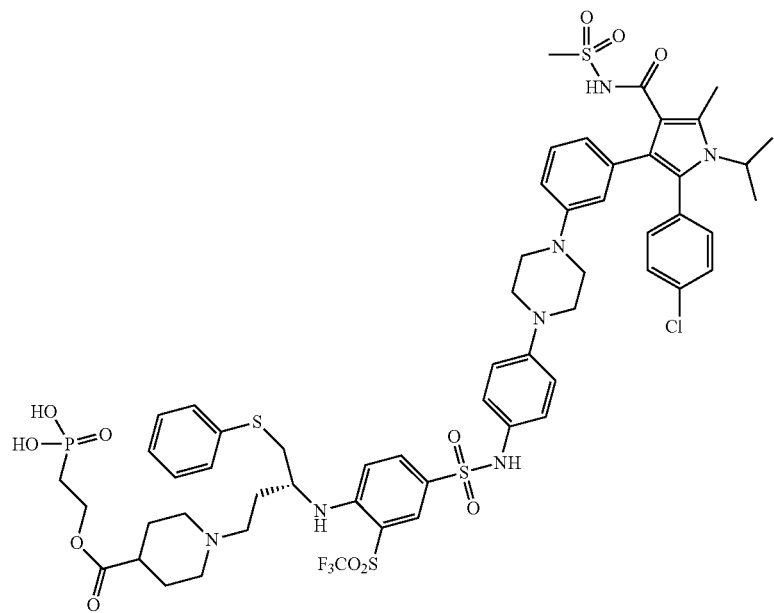 |
| 28 | 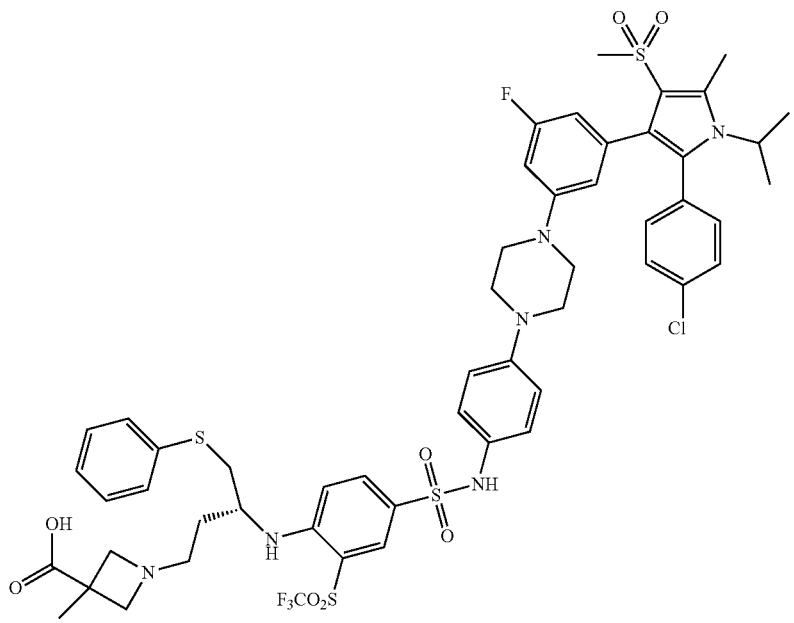 |

| Compound No. | Structure |
|---|---|
| 29 | 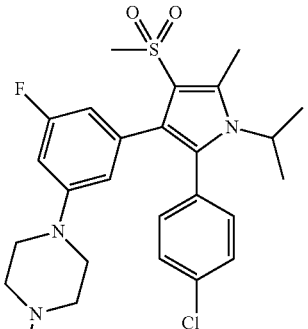 |
| 30 | 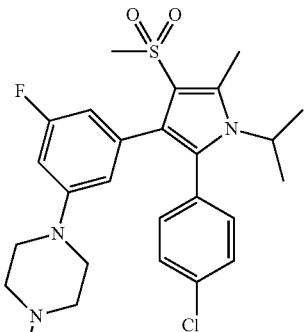 |

The present invention provides Bcl-2/Bcl-xL inhibitors, as exemplified by compounds of structural formula (I), (II), and (III), for the treatment of a variety of diseases and conditions wherein inhibition of Bcl-2 and/or Bcl-xL has a beneficial effect. In one embodiment, the present invention relates to a method of treating an individual suffering from a disease or condition wherein inhibition of the Bcl-2/Bcl-xL provides a benefit comprising administering a therapeutically effective amount of a compound of structural formula (I), (II), or (III) to an individual in need thereof.

The method of the present invention can be accomplished by administering a compound of structural formula (I), (II), or (III) as the neat compound or as a pharmaceutical composition. Administration of a pharmaceutical composition, or neat compound of structural formula (I), (II), or (III), can be performed during or after the onset of the disease or condition of interest. Typically, the pharmaceutical compositions are sterile, and contain no toxic, carcinogenic, or mutagenic compounds that would cause an adverse reaction when administered. Further provided are kits comprising a compound of structural formula (I), (II), or (III) and, optionally, a second therapeutic agent useful in the treatment of diseases and conditions wherein inhibition of Bcl-2/Bcl-xL provides a benefit, packaged separately or together, and an insert having instructions for using these active agents.

In many embodiments, a compound of structural formula (I), (II), or (III) is administered in conjunction with a second therapeutic agent useful in the treatment of a disease or condition wherein inhibition of Bcl-2/Bcl-xL provides a benefit. The second therapeutic agent is different from the compound of structural formula (I), (II), and (III). A compound of structural formula (I), (II), or (III) and the second therapeutic agent can be administered simultaneously or sequentially to achieve the desired effect. In addition, the compound of structural formula (I), (II), or (III) and second therapeutic agent can be administered from a single composition or two separate compositions.

The second therapeutic agent is administered in an amount to provide its desired therapeutic effect. The effective dosage range for each second therapeutic agent is known in the art, and the second therapeutic agent is administered to an individual in need thereof within such established ranges.

A compound of structural formula (I), (II), or (III) and the second therapeutic agent can be administered together as a single-unit dose or separately as multi-unit doses, wherein the compound of structural formula (I), (II), or (III) is administered before the second therapeutic agent or vice versa. One or more dose of the compound of structural formula (I), (II), or (III) and/or one or more dose of the second therapeutic agent can be administered. The compounds of structural formula (I), (II), and (III) therefore can be used in conjunction with one or more second therapeutic agents, for example, but not limited to, anticancer agents.

The diseases and conditions that can be treated in accordance to the invention include, for example, cancers. A variety of cancers can be treated including, but not limited to: carcinomas, including bladder (including accelerated and metastatic bladder cancer), breast, colon (including colorectal cancer), kidney, liver, lung (including small and non-small cell lung cancer and lung adenocarcinoma), ovary, prostate, testes, genitourinary tract, lymphatic system, rectum, larynx, pancreas (including exocrine pancreatic carcinoma), esophagus, stomach, gall bladder, cervix, thyroid, renal, and skin (including squamous cell carcinoma); hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma, histiocytic lymphoma, and Burketts lymphoma, hematopoietic tumors of myeloid lineage, including acute and chronic myelogenous leukemias, myelodysplastic syndrome, myeloid leukemia, and promyelocytic leukemia; tumors of the central and peripheral nervous system, including astrocytoma, neuroblastoma, glioma, and schwannomas; tumors of mesenchymal origin, including fibrosarcoma, rhabdomyoscarcoma, and osteosarcoma; and other tumors, including melanoma, xenoderma pigmentosum, keratoactanthoma, seminoma, thyroid follicular cancer, teratocarcinoma, renal cell carcinoma (RCC), pancreatic cancer, myeloma, myeloid and lymphoblastic leukemia, neuroblastoma, and glioblastoma.

Additional forms of cancer treatable by the Bcl-2/Bcl-xL inhibitors of the present invention include, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer (including small cell carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma), gastrointestinal cancers (including stomach cancer, colon cancer, colorectal cancer, and polyps associated with colorectal neoplasia), pancreatic cancer, liver cancer, urological cancers (including bladder cancer, such as primary superficial bladder tumors, invasive transitional cell carcinoma of the bladder, and muscle-invasive bladder cancer), prostate cancer, malignancies of the female genital tract (including ovarian carcinoma, primary peritoneal epithelial neoplasms, cervical carcinoma, uterine endometrial cancers, vaginal cancer, cancer of the vulva, uterine cancer and solid tumors in the ovarian follicle), malignancies of the male genital tract (including testicular cancer and penile cancer), kidney cancer (including renal cell carcinoma, brain cancer (including intrinsic brain tumors, neuroblastoma, astrocytic brain tumors, gliomas, and metastatic tumor cell invasion in the central nervous system), bone cancers (including osteomas and osteosarcomas), skin cancers (including malignant melanoma, tumor progression of human skin keratinocytes, and squamous cell cancer), thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma.

Additional diseases and conditions, including cancers, that can be treated by administration of a present Bcl-2/Bcl-xL inhibitor are disclosed in U.S. Patent Publication No. 2007/0027135; U.S. Pat. No. 7,432,304; U.S. Patent Publication No. 2010/0278921; and WO 2012/017251, designating the U.S., each incorporated herein in its entirety.

In the present method, a therapeutically effective amount of one or more compound (I), (II), or (III), typically formulated in accordance with pharmaceutical practice, is administered to a human being in need thereof. Whether such a treatment is indicated depends on the individual case and is subject to medical assessment (diagnosis) that takes into consideration signs, symptoms, and/or malfunctions that are present, the risks of developing particular signs, symptoms and/or malfunctions, and other factors.

A compound of structural formula (I), (II), or (III) can be administered by any suitable route, for example by oral, buccal, inhalation, sublingual, rectal, vaginal, intracisternal or intrathecal through lumbar puncture, transurethral, nasal, percutaneous, i.e., transdermal, or parenteral (including intravenous, intramuscular, subcutaneous, intracoronary, intradermal, intramammary, intraperitoneal, intraarticular, intrathecal, retrobulbar, intrapulmonary injection and/or surgical implantation at a particular site) administration. Parenteral administration can be accomplished using a needle and syringe or using a high pressure technique.

Pharmaceutical compositions include those wherein a compound of structural formula (I), (II), or (III) is administered in an effective amount to achieve its intended purpose. The exact formulation, route of administration, and dosage is determined by an individual physician in view of the diagnosed condition or disease. Dosage amount and interval can be adjusted individually to provide levels of a compound of structural formula (I), (II), or (III) that is sufficient to maintain therapeutic effects.

Toxicity and therapeutic efficacy of the compounds of structural formula (I), (II), and (III) can be determined by standard pharmaceutical procedures in cell cultures or experimental animals, e.g., for determining the maximum tolerated dose (MTD) of a compound, which defines as the highest dose that causes no toxicity in animals. The dose ratio between the maximum tolerated dose and therapeutic effects (e.g. inhibiting of tumor growth) is the therapeutic index. The dosage can vary within this range depending upon the dosage form employed, and the route of administration utilized. Determination of a therapeutically effective amount is well within the capability of those skilled in the art, especially in light of the detailed disclosure provided herein.

A therapeutically effective amount of a compound of structural formula (I), (II), or (III) required for use in therapy varies with the nature of the condition being treated, the length of time that activity is desired, and the age and the condition of the patient, and ultimately is determined by the attendant physician. Dosage amounts and intervals can be adjusted individually to provide plasma levels of the Bcl-2/Bcl-xL inhibitor that are sufficient to maintain the desired therapeutic effects. The desired dose conveniently can be administered in a single dose, or as multiple doses administered at appropriate intervals, for example as one, two, three, four or more sub-doses per day. Multiple doses often are desired, or required. For example, a present Bcl-2/Bcl-xL inhibitor can be administered at a frequency of: one dose per day for 2 days with rest for 5 days for 2 weeks; one dose per day for 3 days with rest for 4 days for 3 weeks; weekly dosing for 2 weeks; weekly dosing for 4 weeks; or, any dose regimen determined to be appropriate for the circumstance.

A compound of structural formula (I), (II), or (III) used in a method of the present invention can be administered in an amount of about 0.005 to about 500 milligrams per dose, about 0.05 to about 250 milligrams per dose, or about 0.5 to about 100 milligrams per dose. For example, a compound of structural formula (I), (II), or (III) can be administered, per dose, in an amount of about 0.005, 0.05, 0.5, 5, 10, 20, 30, 40, 50, 100, 150, 200, 250, 300, 350, 400, 450, or 500 milligrams, including all doses between 0.005 and 500 milligrams.

The dosage of a composition containing a Bcl-2/Bcl-xL inhibitor of structural formula (I), (II), or (III) or a composition containing the same, can be from about 1 ng/kg to about 200 mg/kg, about 1 µg/kg to about 100 mg/kg, or about 1 mg/kg to about 50 mg/kg. The dosage of a composition can be at any dosage including, but not limited to, about 1 µg/kg. The dosage of a composition may be at any dosage including, but not limited to, about 1 µg/kg, 10 µg/kg, 25 µg/kg, 50 µg/kg, 75 µg/kg, 100 µg/kg, 125 µg/kg, 150 µg/kg, 175 µg/kg, 200 µg/kg, 225 µg/kg, 250 µg/kg, 275 µg/kg, 300 µg/kg, 325 µg/kg, 350 µg/kg, 375 µg/kg, 400 µg/kg, 425 µg/kg, 450 µg/kg, 475 µg/kg, 500 µg/kg, 525 µg/kg, 550 µg/kg, 575 µg/kg, 600 µg/kg, 625 µg/kg, 650 µg/kg, 675 µg/kg, 700 µg/kg, 725 µg/kg, 750 µg/kg, 775 µg/kg, 800 µg/kg, 825 µg/kg, 850 µg/kg, 875 µg/kg, 900 µg/kg, 925 µg/kg, 950 µg/kg, 975 µg/kg, 1 mg/kg, 5 mg/kg, 10 mg/kg, 15 mg/kg, 20 mg/kg, 25 mg/kg, 30 mg/kg, 35 mg/kg, 40 mg/kg, 45 mg/kg, 50 mg/kg, 60 mg/kg, 70 mg/kg, 80 mg/kg, 90 mg/kg, 100 mg/kg, 125 mg/kg, 150 mg/kg, 175 mg/kg, or 200 mg/kg. The above dosages are exemplary of the average case, but there can be individual instances in which higher or lower dosages are merited, and such are within the scope of this invention. In practice, the physician determines the actual dosing regimen that is most suitable for an individual patient, which can vary with the age, weight, and response of the particular patient.

In the treatment of a cancer, a compound of structural formula (I), (II), or (III) can be administered with a chemotherapeutic agent and/or radiation.

Embodiments of the present invention employ electromagnetic radiation of: gamma-radiation ($10^{-20}$ to $10^{-13}$ m), X-ray radiation ($10^{-12}$ to $10^{-9}$ m), ultraviolet light (10 nm to 400 nm), visible light (400 nm to 700 nm), infrared radiation (700 nm to 1 mm), and microwave radiation (1 mm to 30 cm).

Many cancer treatment protocols currently employ radiosensitizers activated by electromagnetic radiation, e.g., X-rays. Examples of X-ray-activated radiosensitizers include, but are not limited to, metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FUdR), hydroxyurea, cis-platin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, PHOTOFRIN®, benzoporphyrin derivatives, NPe6, tin etioporphyrin (SnET2), pheoborbide-a, bacteriochlorophyll-a, naphthalocyanines, phthalocyanines, zinc phthalocyanine, and therapeutically effective analogs and derivatives of the same.

Radiosensitizers can be administered in conjunction with a therapeutically effective amount of one or more compounds in addition to a present Bcl-2/Bcl-xL inhibitor, such compounds including, but not limited to, compounds that promote the incorporation of radiosensitizers to the target cells, compounds that control the flow of therapeutics, nutrients, and/or oxygen to the target cells, chemotherapeutic agents that act on the tumor with or without additional radiation, or other therapeutically effective compounds for treating cancer or other disease. Examples of additional therapeutic agents that can be used in conjunction with radiosensitizers include, but are not limited to, 5-fluorouracil (5-FU), leucovorin, oxygen, carbogen, red cell transfusions, perfluorocarbons (e.g., FLUOSOLW®-DA), 2,3-DPG, BW12C, calcium channel blockers, pentoxifylline, antiangiogenesis compounds, hydralazine, and L-BSO.

The chemotherapeutic agent can be any pharmacological agent or compound that induces apoptosis. The pharmacological agent or compound can be, for example, a small organic molecule, peptide, polypeptide, nucleic acid, or antibody. Chemotherapeutic agents that can be used include, but are not limited to, alkylating agents, antimetabolites, hormones and antagonists thereof, natural products and their derivatives, radioisotopes, antibodies, as well as natural products, and combinations thereof. For example, a Bcl-2/Bcl-xL inhibitor of the present invention can be administered with antibiotics, such as doxorubicin and other anthracycline analogs, nitrogen mustards, such as cyclophosphamide, pyrimidine analogs such as 5-fluorouracil, cis-platin, hydroxyurea, taxol and its natural and synthetic derivatives, and the like. As another example, in the case of mixed tumors, such as adenocarcinoma of the breast, where the tumors include gonadotropin-dependent and gonadotropin-independent cells, the compound can be administered in conjunction with leuprolide or goserelin (synthetic peptide analogs of LH-RH). Other antineoplastic protocols include the use of an inhibitor compound with another treatment modality, e.g., surgery or radiation, also referred to herein as "adjunct anti-neoplastic modalities." Additional chemotherapeutic agents useful in the invention include hormones and antagonists thereof, radioisotopes, antibodies, natural products, and combinations thereof.

Examples of chemotherapeutic agents useful in a method of the present invention are listed in the following table.

TABLE 1

Alkylating agents
Nitrogen mustards mechlorethamine
cyclophosphamide
ifosfamide
melphalan
chlorambucil
uracil mustard
temozolomide
Nitrosoureas carmustine (BCNU)
lomustine (CCNU)
semustine (methyl-CCNU)
chlormethine
streptozocin
Ethylenimine/Methyl-melamine triethylenemelamine (TEM)
triethylene thiophosphoramide
(thiotepa)
hexamethylmelamine
(HMM, altretamine)
Alkyl sulfonates busulfan
pipobroman
Triazines dacarbazine (DTIC)
Antimetabolites
Folic Acid analogs methotrexate
trimetrexate
pemetrexed
(Multi-targeted antifolate)
Pyrimidine analogs 5-fluorouracil
fluorodeoxyuridine
gemcitabine
cytosine arabinoside
(AraC, cytarabine)
5-azacytidine
2,2'-difluorodeoxy-cytidine
floxuridine
pentostatine
Purine analogs 6-mercaptopurine
6-thioguanine
azathioprine
2'-deoxycoformycin
(pentostatin)
erythrohydroxynonyl-adenine (EHNA)
fludarabine phosphate
2-chlorodeoxyadenosine
(cladribine, 2-CdA)
Type I Topoisomerase Inhibitors camptothecin
topotecan
irinotecan
Biological response modifiers G-CSF
GM-CSF
Differentiation Agents retinoic acid derivatives
Hormones and antagonists
Adrenocorticosteroids/antagonists prednisone and equivalents
dexamethasone
ainoglutethimide

TABLE 1-continued

Progestins hydroxyprogesterone caproate
medroxyprogesterone acetate
megestrol acetate
Estrogens diethylstilbestrol
ethynyl estradiol/equivalents
Antiestrogen tamoxifen
Androgens testosterone propionate
fluoxymesterone/equivalents
Antiandrogens flutamide
gonadotropin-releasing
hormone analogs
leuprolide
Natural products
Antimitotic drugs
Taxanes paclitaxel
Vinca alkaloids
vinblastine (VLB)
vincristine
vinorelbine
vindesine
Taxotere ® (docetaxel)
estramustine
estramustine phosphate
Epipodophylotoxins etoposide
teniposide
Antibiotics actimomycin D
daunomycin (rubidomycin)
doxorubicin (adriamycin)
mitoxantroneidarubicin
bleomycin
splicamycin (mithramycin)
mitromycin-C
dactinomycin
aphidicolin
epirubicin
idarubicin
daunorubicin
mithramycin
deoxy co-formycin
Enzymes L-asparaginase
L-arginase
Radiosensitizers metronidazole
misonidazole
desmethylmisonidazole
pimonidazole
etanidazole
nimorazole
RSU 1069
EO9
RB 6145
Nonsteroidal antiandrogens SR4233
flutamide
nicotinamide
5-bromodeozyuridine
5-iododeoxyuridine
bromodeoxycytidine
Miscellaneous agents

TABLE 1-continued

Platinium coordination complexes cisplatin
carboplatin
oxaliplatin
anthracenedione
mitoxantrone
Substituted urea hydroxyurea
Methylhydrazine derivatives N-methylhydrazine (MIH)
procarbazine
Adrenocortical suppressant mitotane (o,p'-DDD)
ainoglutethimide
Cytokines interferon ($\alpha$, $\beta$, $\gamma$)
interleukin-2
Photosensitizers hematoporphyrin derivatives
PHOTOFRIN ®
benzoporphyrin derivatives
Npe6
tin etioporphyrin (SnET2)
pheoboride-a
bacteriochlorophyll-a
naphthalocyanines
phthalocyanines
zinc phthalocyanines
Radiation X-ray
ultraviolet light
gamma radiation
visible light
infrared radiation
microwave radiation Microtubule affecting agents interfere with cellular mitosis and are well known in the art for their cytotoxic activity. Microtubule affecting agents useful in the invention include, but are not limited to, allocolchicine (NSC 406042), halichondrin B (NSC 609395), colchicines (NSC 757), colchicines derivatives (e.g., NSC 33410), dolastatin 10 (NSC 376128), maytansine (NSC 153858), rhizoxin (NSC 332598), paclitaxel (NSC 125973), TAXOL® derivatives (e.g., NSC 608832), thiocolchicine NSC 361792), trityl cysteine (NSC 83265), vinblastine sulfate (NSC 49842), vincristine sulfate (NSC 67574), natural and synthetic epothilones including but not limited to epothilone A, eopthilone B, and discodermolide (see Service, (1996) Science, 274:2009) estramustine, nocodazole, MAP4, and the like. Examples of such agents are also described in Bulinski (1997) *J. Cell Sci.* 110:3055 3064; Panda (1997) *Proc. Natl. Acad. Sci. USA* 94:10560-10564; Muhlradt (1997) *Cancer Res.* 57:3344-3346; Nicolaou (1997) *Nature* 397:268-272; Vasquez (1997) *Mol. Biol. Cell.* 8:973-985; and Panda (1996) *J. Biol. Chem.* 271:29807-29812.

Cytostatic agents that may be used include, but are not limited to, hormones and steroids (including synthetic analogs): 17-$\alpha$-ethinylestadiol, diethylstilbestrol, testosterone, prednisone, fluoxymesterone, dromostanolone propionate, testolactone, megestrolacetate, methylprednisolone, methyltestosterone, prednisolone, triamcinolone, hlorotrianisene, hydroxyprogesterone, aminogluthimide, estramustine, medroxyprogesteroneacetate, leuprolide, flutamide, toremifene, and zoladex.

Other cytostatic agents are antiangiogenics, such as matrix metalloproteinase inhibitors, and other VEGF inhibitors, such as anti-VEGF antibodies and small molecules such as ZD6474 and SU668. Anti-Her2 antibodies also may be utilized. An EGFR inhibitor is EKB-569 (an irreversible inhibitor). Also included are antibody C225 immunospecific for the EGFR and Src inhibitors.

Also suitable for use as a cytostatic agent is CASODEX® (bicalutamide, Astra Zeneca) which renders androgen-dependent carcinomas non-proliferative. Yet another example of a cytostatic agent is the antiestrogen TAMOXIFEN® which inhibits the proliferation or growth of estrogen dependent breast cancer. Inhibitors of the transduction of cellular proliferative signals are cytostatic agents. Representative examples include epidermal growth factor inhibitors, Her-2 inhibitors, MEK-1 kinase inhibitors, MAPK kinase inhibitors, PI3 inhibitors, Src kinase inhibitors, and PDGF inhibitors.

Additional second therapeutic agents that can be administered with a Bcl-2/Bcl-xL inhibitor of the present invention are disclosed in U.S. Patent Publication 2007/0027135; U.S. Pat. No. 7,432,304; U.S. Patent Publication No. 2010/0278921; WO 2012/017251, designating the U.S., each incorporated herein by reference.

The compounds of the present invention typically are administered in admixture with a pharmaceutical carrier selected with regard to the intended route of administration and standard pharmaceutical practice. Pharmaceutical compositions for use in accordance with the present invention are formulated in a conventional manner using one or more physiologically acceptable carriers comprising excipients and auxiliaries that facilitate processing of compounds of structural formula (I), (II), and (III).

These pharmaceutical compositions can be manufactured, for example, by conventional mixing, dissolving, granulating, dragee-making, emulsifying, encapsulating, entrapping, or lyophilizing processes. Proper formulation is dependent upon the route of administration chosen. When a therapeutically effective amount of the compound of structural formula (I), (II), or (III) is administered orally, the composition typically is in the form of a tablet, capsule, powder, solution, or elixir. When administered in tablet form, the composition additionally can contain a solid carrier, such as a gelatin or an adjuvant. The tablet, capsule, and powder contain about 0.01% to about 95%, and preferably from about 1% to about 50%, of a compound of structural formula (I), (II), or (III). When administered in liquid form, a liquid carrier, such as water, petroleum, or oils of animal or plant origin, can be added. The liquid form of the composition can further contain physiological saline solution, dextrose or other saccharide solutions, or glycols. When administered in liquid form, the composition contains about 0.1% to about 90%, and preferably about 1% to about 50%, by weight, of a compound of structural formula (I), (II), or (III).

When a therapeutically effective amount of a compound of structural formula (I), (II), or (III) is administered by intravenous, cutaneous, or subcutaneous injection, the composition is in the form of a pyrogen-free, parenterally acceptable aqueous solution. The preparation of such parenterally acceptable solutions, having due regard to pH, isotonicity, stability, and the like, is within the skill in the art. A preferred composition for intravenous, cutaneous, or subcutaneous injection typically contains, an isotonic vehicle.

Compounds of structural formula (I), (II), and (III) can be readily combined with pharmaceutically acceptable carriers well-known in the art. Such carriers enable the active agents to be formulated as tablets, pills, dragees, capsules, liquids, gels, syrups, slurries, suspensions and the like, for oral ingestion by a patient to be treated. Pharmaceutical preparations for oral use can be obtained by adding the compound of structural formula (I), (II), or (III) to a solid excipient, optionally grinding the resulting mixture, and processing the mixture of granules, after adding suitable auxiliaries, if desired, to obtain tablets or dragee cores. Suitable excipients include, for example, fillers and cellulose preparations. If desired, disintegrating agents can be added.

A compound of structural formula (I), (II), and (III) can be formulated for parenteral administration by injection, e.g., by bolus injection or continuous infusion. Formulations for injection can be presented in unit dosage form, e.g., in ampules or in multidose containers, with an added preservative. The compositions can take such forms as suspensions, solutions, or emulsions in oily or aqueous vehicles, and can contain formulatory agents such as suspending, stabilizing, and/or dispersing agents.

Pharmaceutical compositions for parenteral administration include aqueous solutions of the active agent in water-soluble form. Additionally, suspensions of a compound of structural formula (I), (II), or (III) can be prepared as appropriate oily injection suspensions. Suitable lipophilic solvents or vehicles include fatty oils or synthetic fatty acid esters. Aqueous injection suspensions can contain substances which increase the viscosity of the suspension. Optionally, the suspension also can contain suitable stabilizers or agents that increase the solubility of the compounds and allow for the preparation of highly concentrated solutions. Alternatively, a present composition can be in powder form for constitution with a suitable vehicle, e.g., sterile pyrogen-free water, before use.

A compound of structural formula (I), (II), or (III) also can be formulated in rectal compositions, such as suppositories or retention enemas, e.g., containing conventional suppository bases. In addition to the formulations described previously, the compound of structural formula (I), (II), or (III) also can be formulated as a depot preparation. Such long-acting formulations can be administered by implantation (for example, subcutaneously or intramuscularly) or by intramuscular injection. Thus, for example, the compounds of structural formula (I), (II), or (III) can be formulated with suitable polymeric or hydrophobic materials (for example, as an emulsion in an acceptable oil) or ion exchange resins.

In particular, the compounds of structural formula (I), (II), and (III) can be administered orally, buccally, or sublingually in the form of tablets containing excipients, such as starch or lactose, or in capsules or ovules, either alone or in admixture with excipients, or in the form of elixirs or suspensions containing flavoring or coloring agents. Such liquid preparations can be prepared with pharmaceutically acceptable additives, such as suspending agents. The compounds of structural formula (I), (II), and (III) also can be injected parenterally, for example, intravenously, intramuscularly, subcutaneously, or intracoronarily. For parenteral administration, the Bcl-2/Bcl-xL inhibitors are best used in the form of a sterile aqueous solution which can contain other substances, for example, salts or monosaccharides, such as mannitol or glucose, to make the solution isotonic with blood.

As an additional embodiment, the present invention includes kits which comprise one or more compounds or compositions packaged in a manner that facilitates their use to practice methods of the invention. In one simple embodiment, the kit includes a compound or composition described herein as useful for practice of a method (e.g., a composition comprising a compound of structural formula (I), (II), or (III) and an optional second therapeutic agent), packaged in a container, such as a sealed bottle or vessel, with a label affixed to the container or included in the kit that describes use of the compound or composition to practice the method of the invention. Preferably, the compound or composition is packaged in a unit dosage form. The kit further can include a device suitable for administering the composition according to the intended route of administration.

In addition to its use in therapeutic medicine, compounds of structural formula (I), (II), and (III), and pharmaceutically acceptable salts thereof, also are useful as pharmacological tools in the development and standardization of in vitro and in vivo test systems for the evaluation of the effects of inhibitors of Bcl-2 and/or Bcl-$X_L$ in laboratory animals, such as cats, dogs, rabbits, monkeys, rats, and mice, as part of the search for new therapeutic agents.

Prior Bcl-2/Bcl-xL inhibitors possessed properties that hindered their development as therapeutic agents. In accordance with an important feature of the present invention, compounds of structural formula (I), (II), and (III) were synthesized and evaluated as inhibitors for Bcl-2/Bcl-xL. For example, compounds of the present invention typically have a binding affinity ($IC_{50}$) to Bcl-2/Bcl-xL of less than 100 nM.

Synthesis of Compounds

Compounds of the present invention were prepared as follows. The following synthetic schemes are representative of the reactions used to synthesize compounds of structural formula (I), (II), and (III). Modifications and alternate schemes to prepare Bcl-2/Bcl-xL inhibitors of the invention are readily within the capabilities of persons skilled in the art.

Solvents and reagents were obtained commercially and used without further purification. Chemical shifts (δ) of NMR spectra are reported as δ values (ppm) downfield relative to an internal standard, with multiplicities reported in the usual manner.

Unless otherwise stated all temperatures are in degrees Celsius.

Certain key intermediates for the synthesis of the compounds of the present invention can be synthesized by the methods as set forth in WO 2012/103059, designating the U.S., and incorporated herein by reference in its entirety followed by conversion to its phosphate derivative as follows:

Scheme 1. Synthesis of compound 1

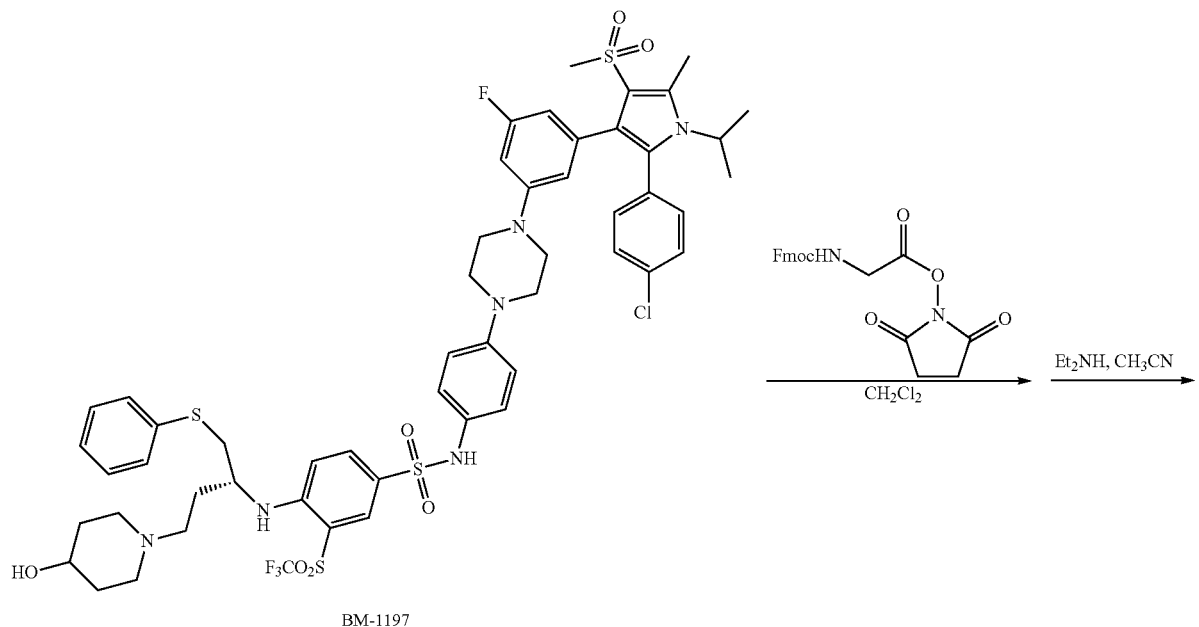

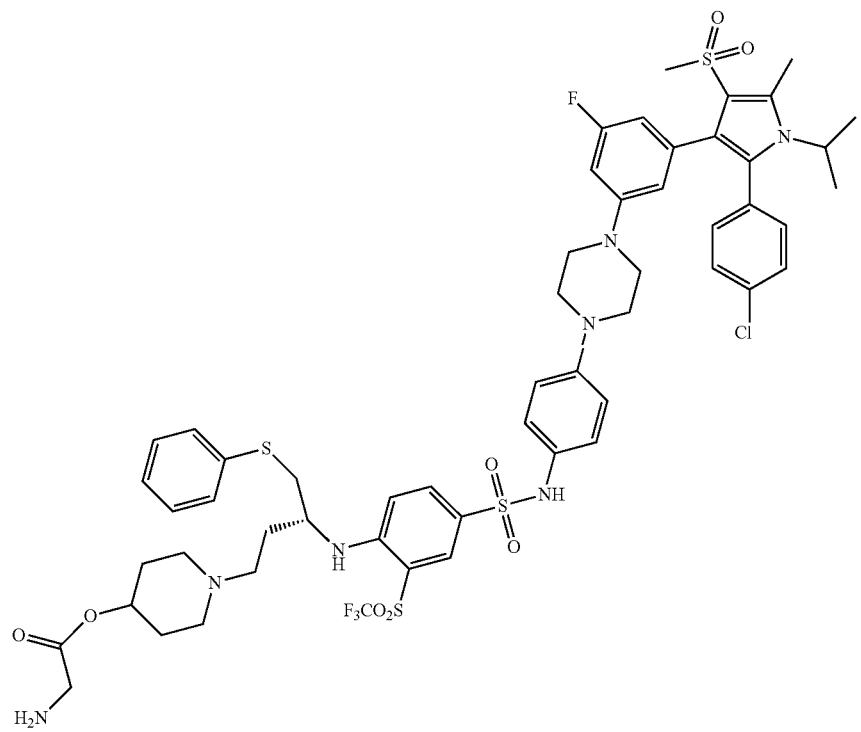

Experimental Section (R)-1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)piperidin-4-yl 2-aminoacetate (1)

A solution of BM-1197 (113 mg, 0.10 mmol) and Fmoc-Gly-OSu (43 mg, 0.11 mmol) in CH$_2$Cl$_2$ (2 mL) was stirred at room temperature for 1 hour until no BM-1197 was observed by TLC. The solution was concentrated in vacuo to provide crude precursor of 1 which was used for next step without purification. The resulting residue was dissolved in Aceonitrile (5 mL) and followed by addition of diethyl amine (0.2 mL, 2 mmol). The mixture was stirred at room temperature for overnight until no starting material was observed by TLC and concentrated in vacuo. The residue was purified by HPLC to give the product 1 (salt with TFA, 83 mg, yield 70% over two steps). The gradient ran from 60% of solvent A and 40% of solvent B to 20% of solvent A and 80% of solvent B in 40 min. MS (ESI) m/z 1189.08 (M+H)$^+$.

Scheme 2. Synthesis of 2

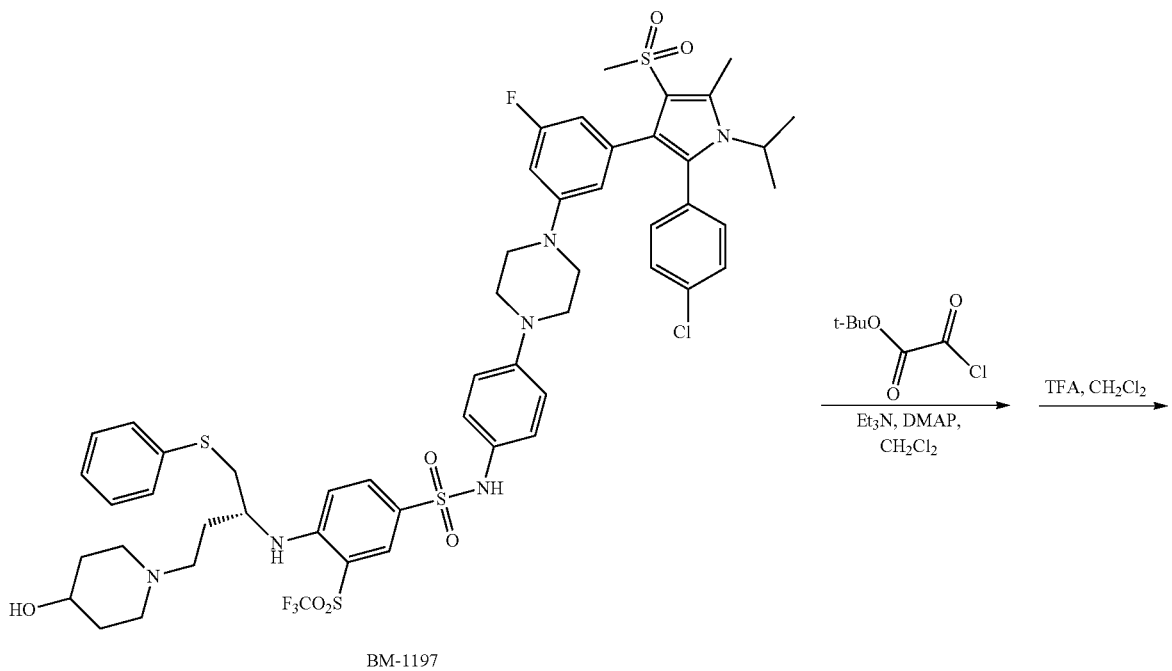

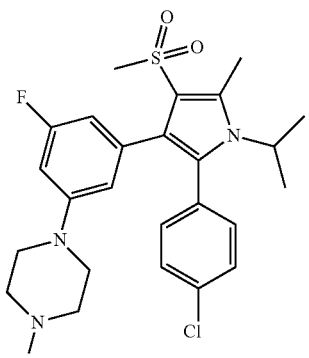

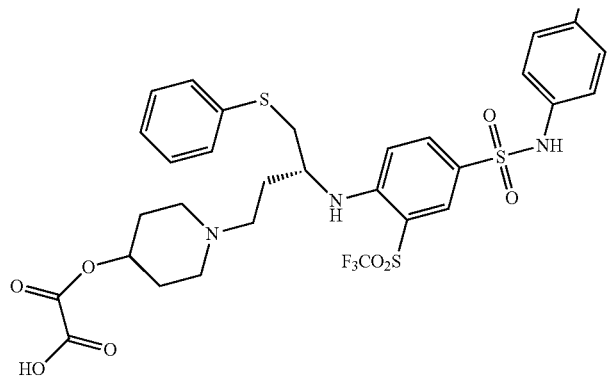

Experimental Section (R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)piperidin-4-yloxy)-2-oxoacetic acid (2)

To a solution of BM-1197 (113 mg, 0.10 mmol), DMAP (2 mg, 0.02 mmol), Et₃N (42 uL, 0.3 mmol) in CH₂Cl₂ (2 mL) was added tert-butyl 2-chloro-2-oxoacetate (33 mg, 0.2 mmol). The solution was stirred at room temperature for 1 hour until no BM-1197 was observed by TLC and concentrated in vacuo. The crude residue was flash chromatographed on silica gel with 5% MeOH/CH₂Cl₂ to provide precursor of 2. The precursor was dissolved in CH₂Cl₂ (3 mL) and followed by addition of TFA (3 mL). The mixture was stirred at room temperature for 1 hour until no starting material was observed by TLC and concentrated in vacuo. The residue was purified by HPLC to give the product 2 (salt with TFA, 66 mg, yield 55% over two steps). The gradient ran from 60% of solvent A and 40% of solvent B to 20% of solvent A and 80% of solvent B in 40 min. MS (ESI) m/z 1189.08 (M+H)⁺.

Scheme 3. Preparation of key intermediate B and D

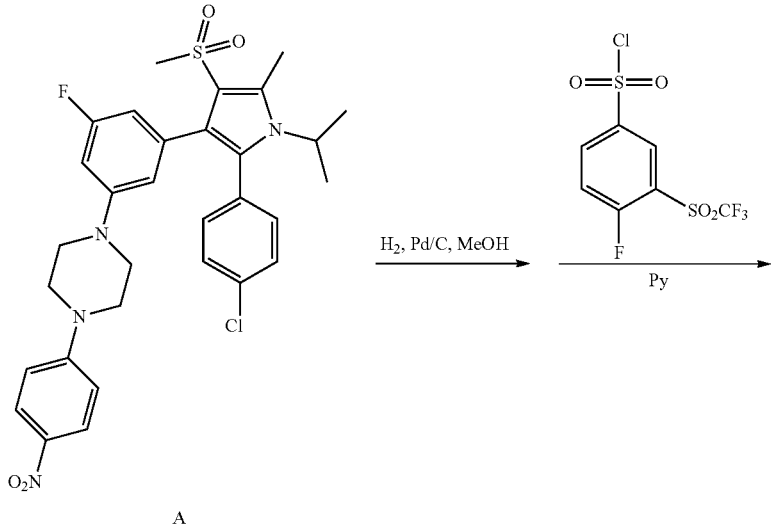

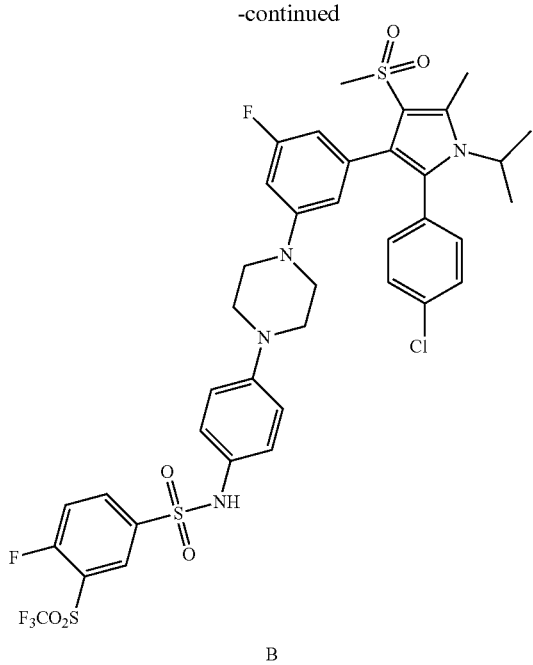

B

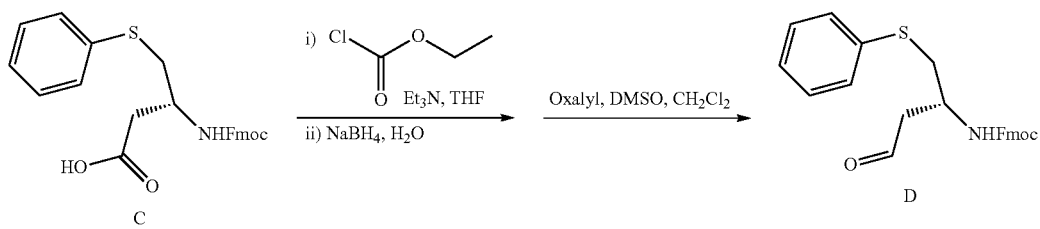

Experimental Section

N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)-4-fluoro-3-(trifluoromethylsulfonyl)benzenesulfonamide (B)

To a solution of A (3.0 g, 4.9 mmol) in 150 mL of methanol was added 10% wt. Pd/C (300 mg, 0.1 eq. m/m). The solution was stirred under hydrogen atmosphere at room temperature for about 20 min until no A was observed by TLC. The reaction mixture was filtered and the filtrate was concentrated in vacuum. The residue was used for next step directly without purification. To the solution of this aniline in pyridine, 4-fluoro-3-(trifluoromethylsulfonyl)benzene-1-sulfonyl chloride (1.8 g, 5.4 mmol) was added at 0° C. The mixture was stirred at 0° C. to room temperature for 1 hour until no aniline was observed by TLC. Water (10 mL) was added and extracted with ethyl acetate (200 mL*2). The combined ethyl acetate solution was washed with brine (150 mL), dried over sodium sulfate and concentrated in vacuo. The concentrate was flash chromatographed on silica gel with 40% EtOA/hexane to provide intermediate B (3.2 g, yield 75% over two steps). MS (ESI) m/z 931.75 (M+K)$^+$.

General Procedure I (R)-(9H-fluoren-9-yl)methyl 4-oxo-1-(phenylthio)butan-2-ylcarbamate (D)

To a solution of C (5.0 g, 11.5 mmol) in THF (100 mL) was added triethylamine (4.8 mL, 34.5 mmol) and ethyl chloroformate (3.3 mL, 34.5 mmol) at −10° C. under argon atmosphere. The mixture was stirred at −10° C. for 1 h and NaBH$_4$ (1.7 g, 46.1 mmol) in water (60 mL) was added dropwise at −10° C. The mixture was stirred at −10° C. for 1 h then at room temperature for 2 h. The reaction was quenched with 1 M aqueous KHSO$_4$ (200 mL) and the mixture was extracted EtOAc (3×200 mL). The extracts were washed with brine (200 mL), dried over anhydrous sodium sulfate, filtered and concentrated in vacuo. The concentrate was flash chromatographed on silica gel with 50% EtOA/hexane to provide corresponding alcohol (4.3 g, yield 90%). To a solution of oxalyl chloride (2.6 mL, 31.1 mmol) in DCM (100 mL) at −78° C., was added dimethyl sulfoxide (3.7 mL, 51.8 mmol). The solution was warmed to −40° C. for 5 min and recooled to −78° C., and then a solution of the resulting alcohol of previous step (4.3 g, 10.4 mmol) in DCM (50 mL) was added dropwise. The solution was stirred for additional 40 min and followed by excess triethylamine (25 mL) and stirred for another 30 min. The reaction mixture was warmed to room temperature followed by adding saturated aqueous ammonium chloride solution (100 mL), and extracted with DCM (2×200 mL). The combined DCM solution was washed with brine (150 mL), dried over sodium sulfate and concentrated in vacuo. The residue was flash chromatographed on silica gel with 20% EtOA/hexane to provide intermediate D (3.7 g, yield 85%). MS (ESI) m/z 418.25 (M+H)⁺.

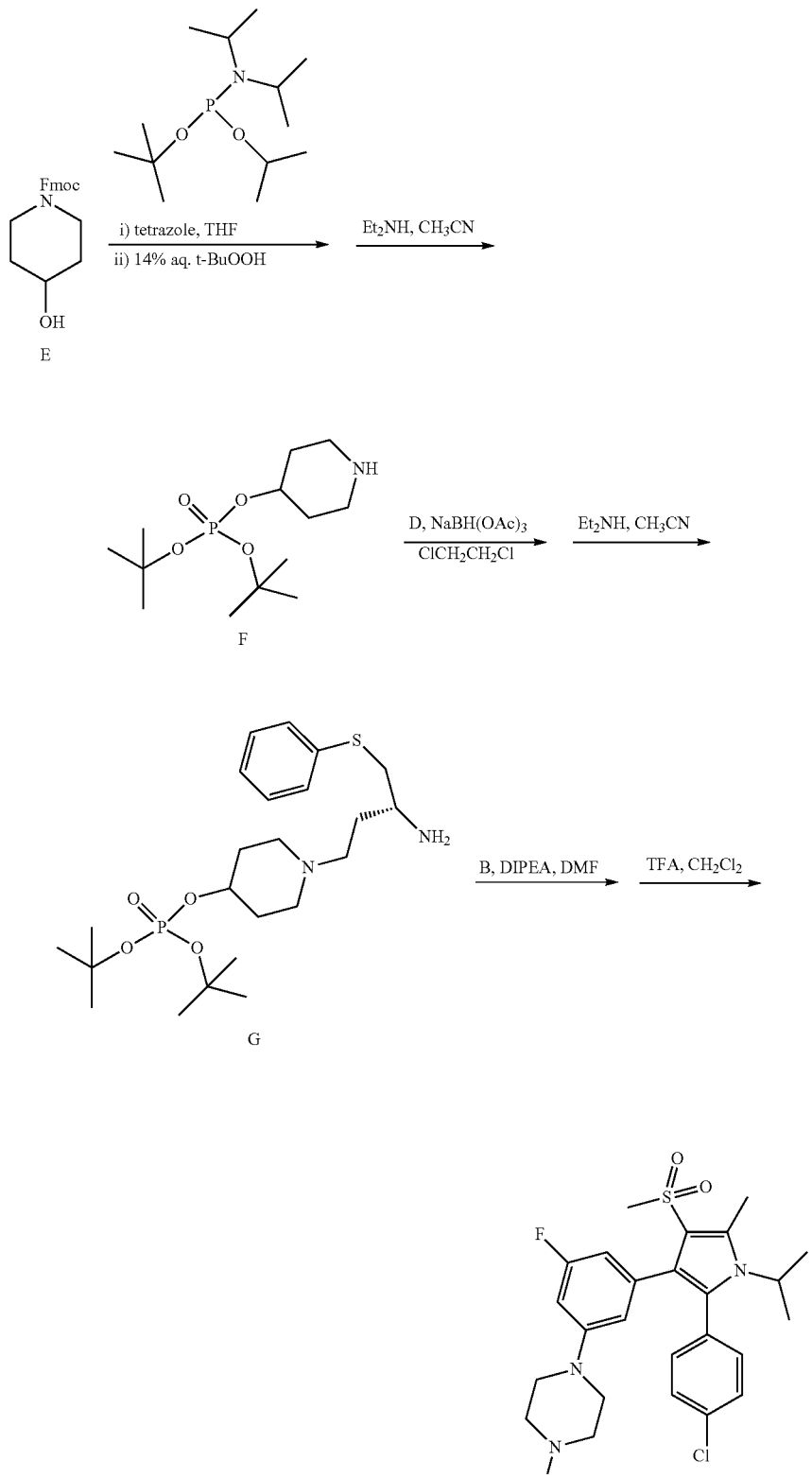

Scheme 4. Synthesis of 3

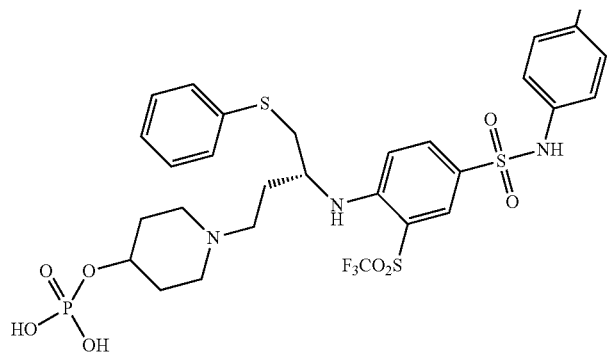

3

Experimental Section

Di-tert-butyl piperidin-4-yl phosphate (F)

The solution of Di-t-butyl di-isopropyl phosphoramidite (832 mg, 3.0 mmol) and tetrazole (6.6 mL, 0.45 M in acetanitril) in THF (15 mL) was stirred under $N_2$ at room temperature for approximately 10 min. Compound E (626 mg, 2.0 mmol) in dry THF (2 mL) was then added to the reaction over 15 minutes and stirred at room temperature under $N_2$ for 2 hours until no E was observed by TLC. The reaction mixture was then cooled to 0° C. and a 14% aqueous solution of t-butyl peroxide (3.0 mL, 4.6 mmol) was added. The temperature was then allowed to rise to room temperature and the mixture was stirred overnight. The reaction was quenched with saturated aqueous $NaHCO_3$ solution (2 mL). Water (50 mL) was added into the reaction mixture, which was then extracted with ethyl acetate (2×50 mL). The combined ethyl acetate solution was washed with brine (50 mL), dried over sodium sulfate and concentrated in vacuo to give crude product which was used for the next step without purification. The resulting residue was dissolved in aceonitrile (20 mL) and followed by addition of diethyl amine (4.1 mL, 40 mmol). The mixture was stirred at room temperature for overnight until no starting material was observed by TLC and concentrated in vacuo. The residue was flash chromatographed on silica gel with 5% MeOH/DCM to provide intermediate F (452 mg, yield 77% over two steps). MS (ESI) m/z 295.17 $(M+H)^+$.

General Procedure II

(R)-1-(3-amino-4-(phenylthio)butyl)piperidin-4-yl di-tert-butyl phosphate (G)

To a solution of F (293 mg, 1.0 mmol) and intermediate D (500 mg, 1.2 mmol) in DCE (10 mL) was added $NaBH(OAc)_3$ (636 mg, 3.0 mmol), and the mixture was stirred at room temperature overnight until no F was observed by TLC. The mixture was diluted with DCM (50 mL), washed with brine (50 mL) and dried over sodium sulfate. The solvent was removed in vacuo to give crude product which was used for the next step without purification. The resulting residue was dissolved in acetonitrile (10 mL) and followed by addition of diethyl amine (2.1 mL, 20 mmol). The mixture was stirred at room temperature for overnight until no starting material was observed by TLC and concentrated in vacuo. The residue was flash chromatographed on silica gel with 10% MeOH/DCM to provide intermediate G (307 mg, yield 65% over two steps). MS (ESI) m/z 474.00 $(M+H)^+$.

General Procedure III

(R)-1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoro methylsulfonyl)phenylamino)-4-(phenylthio)butyl)piperidin-4-yl dihydrogen phosphate (3)

To a solution of B (100 mg, 0.11 mmol) and G (65 mg, 0.14 mmol) in DMF (2 mL) was added DIPEA (1 mL). The solution was stirred for 4 hours at room temperature until no B was observed by TLC. The reaction mixture was concentrated in vacuo to give crude product which was used for next step without purification. The resulting residue was dissolved in DCM (5 mL) and followed by adding TFA (2.5 mL). The solution was stirred at room temperature for 1 h until no material was observed by TLC. The reaction mixture was concentrated in vacuo and the residue was purified by HPLC to give the pure product 3 (salt with TFA, 88 mg, yield 66% over two steps). The gradient ran from 60% of solvent A and 40% of solvent B to 20% of solvent A and 80% of solvent B in 40 min. $^1H$ NMR (300 M Hz, $CD_3OD$): δ 7.96 (s, 1H), 7.73 (d, J=8.9 Hz, 1H), 7.32-7.07 (m, 13H), 6.93-6.41 (m, 4H), 4.61-4.41 (m, 2H), 3.99 (s, 1H), 3.55-3.11 (m, 16H), 2.84 (s, 3H), 2.74 (s, 3H), 2.26-1.80 (m, 6H), 1.43 (d, J=7.0 Hz, 6H). MS (ESI): m/z 1212.67 $(M+H)^+$.

Scheme 5. Synthesis of 4
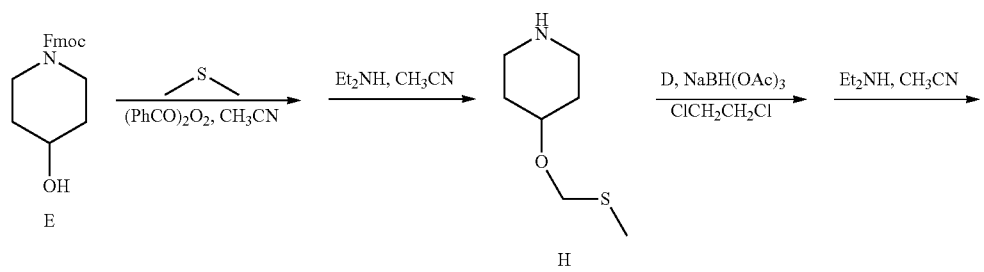
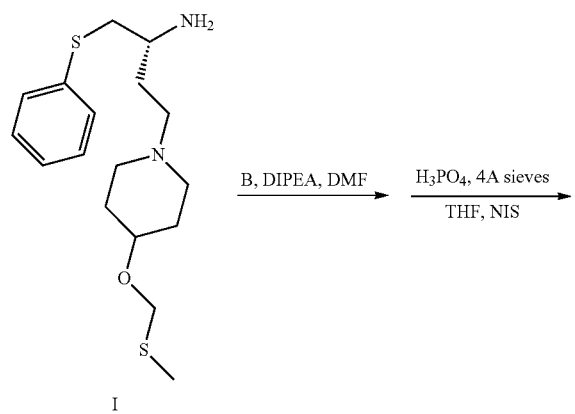
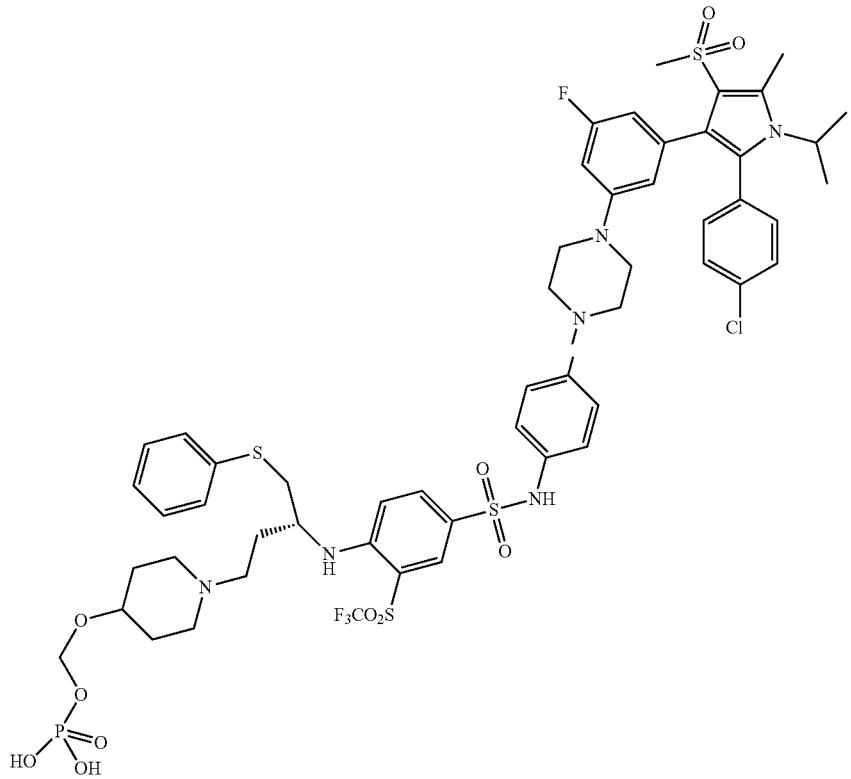
4

Experimental Section

4-(Methylthiomethoxy)piperidine (H)

To a solution of alcohol E (1.0 g, 3.1 mmol) and methyl sulfide (1.8 mL, 24.8 mmol) in acetonitrile (31 mL) at 0° C. was added benzoyl peroxide (3.0 g, 12.4 mmol) in four equal portions over 10 min, and the mixture was stirred at 0° C. for 1 h and then at room temperature for 1 h until no E was observed by TLC. The mixture was diluted with ethyl acetate (100 mL), washed with 10% $Na_2CO_3$ (100 mL) and then brine (100 mL) and dried over sodium sulfate. The solvent was removed in vacuo to give crude product which was used for the next step without purification. The resulting residue was dissolved in acetonitrile (10 mL) and followed by addition of diethyl amine (6.2 mL, 60 mmol). The mixture was stirred at room temperature for overnight until no starting material was observed by TLC and concentrated in vacuo. The residue was flash chromatographed on silica gel with 5% MeOH/DCM to provide intermediate H (270 mg, yield 54% over two steps). MS (ESI) m/z 162.83 (M+H)$^+$.

(R)-4-(4-(methylthiomethoxy)piperidin-1-yl)-1-(phenylthio)butan-2-amine (I)

I was prepared from H and D according general procedure II. MS (ESI) m/z 341.58 (M+H)$^+$.

(R)-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl) sulfamoyl)-2-(trifluoro methylsulfonyl)phenylamino)-4-(phenylthio)butyl)piperidin-4-yloxy)methyl dihydrogen phosphate (4)

To a solution of B (200 mg, 0.23 mmol) and I (86 mg, 0.25 mmol) in DMF (4 mL) was added DIPEA (2 mL). The solution was stirred for 4 hours at room temperature until no B was observed by TLC. The reaction mixture was concentrated in vacuo. The residue was flash chromatographed on silica gel with 5% MeOH/DCM to give corresponding thioether (241 mg, yield 88%). To a solution of the thioether from the first step (200 mg, 0.17 mmol), phosphoric acid (117 mg, 1.2 mmol), and molecular sieves (4 Å, 500 mg) in THF (6 mL) at 0° C. was added N-iodosuccinimide (57 mg, 0.26 mmol), and the mixture was stirred at room temperature for 1 h until no starting material was observed by TLC. The reaction mixture was filtered through Celite, and the solids were washed with methanol. The filtrate was concentrated in vacuo and the residue was purified by HPLC to give the pure product 4 (salt with TFA, 93 mg, yield 44%). The gradient ran from 60% of solvent A and 40% of solvent B to 20% of solvent A and 80% of solvent B in 40 min. MS (ESI): m/z 1242.08 (M+H)$^+$.

Scheme 6. Synthesis of compounds 5, 6, 7

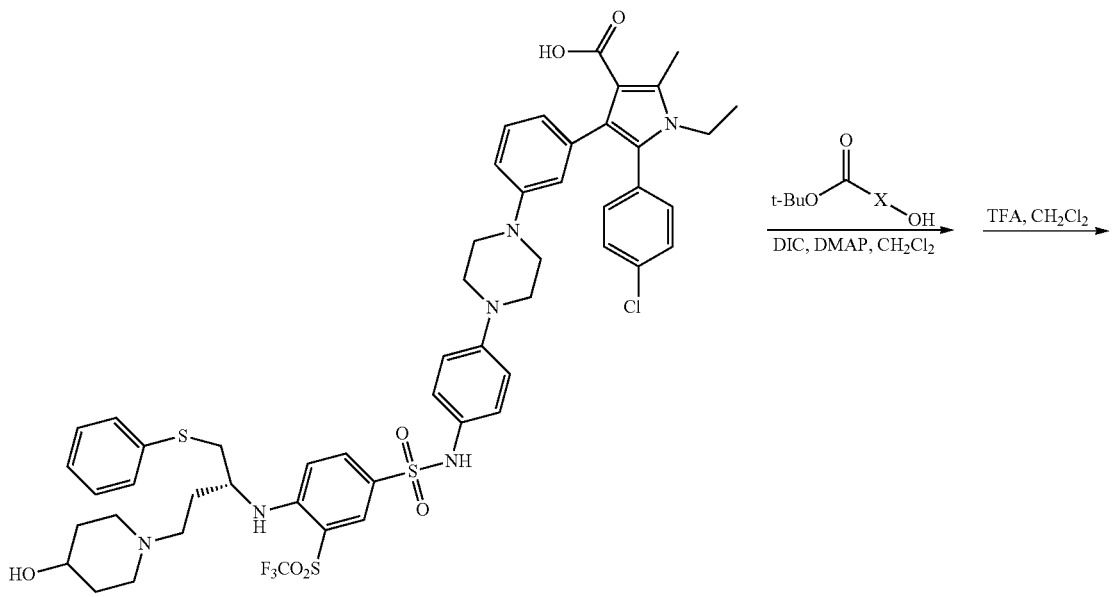

BM-957

-continued

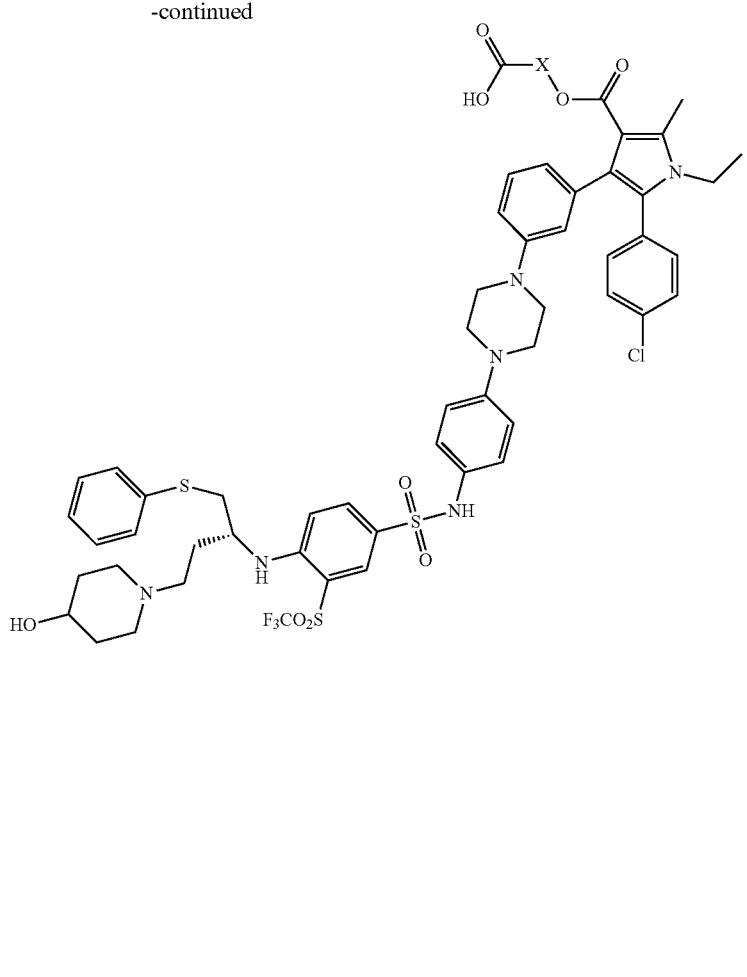

X =

5 [structure: propylene linker]

6 [structure: 1,4-phenylene]

7 [structure: 1,4-cyclohexylene]

Experimental Section

General Procedure IV (R)-3-((5-(4-chlorophenyl)-1-ethyl-4-(3-(4-(4-(4-((4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-2-methyl-1H-pyrrole-3-carbonyl)oxy)propanoic acid (5)

To a solution of 957 (100 mg, 0.09 mmol), DIC (18 mg, 0.14 mmol) and DMAP (20 mg, 0.14 mmol) in DCM (2 mL) was added tert-butyl 3-hydroxypropanoate (41 mg, 0.28 mmol). The solution was stirred for 6 hours at room temperature until no BM-957 was observed by TLC. The reaction mixture was diluted with ethyl acetate (50 mL), washed with saturated NaHCO$_3$ solution (50 mL), brine (50 mL) and dried over sodium sulfate. The solvent was removed in vacuo to give crude product which was used for next step without purification. The resulting residue was dissolved in DCM (5 mL) and followed by adding TFA (2.5 mL). The solution was stirred at room temperature for 3 h until no starting material was observed by TLC. The reaction mixture was concentrated in vacuo and the residue was purified by HPLC to give the pure product 5 (salt with TFA, 75 mg, yield 70% over two steps). The gradient ran from 60% of solvent A and 40% of solvent B to 20% of solvent A and 80% of solvent B in 40 min. MS (ESI): m/z 1238.17 (M+H)$^+$.

(R)-4-((5-(4-chlorophenyl)-1-ethyl-4-(3-(4-(4-(4-((4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-2-methyl-1H-pyrrole-3-carbonyl)oxy)benzoic acid (6)

6 was prepared from BM-957 and tert-butyl 4-hydroxybenzoate according general procedure IV. MS (ESI): m/z 1186.00 (M+H)$^+$.

(R)-4-((5-(4-chlorophenyl)-1-ethyl-4-(3-(4-(4-(4-((4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-2-methyl-1H-pyrrole-3-carbonyl)oxy)cyclohexane carboxylic acid (7)

7 was prepared from BM-957 and tert-butyl 4-hydroxycyclohexanecarboxylate according general procedure IV. MS (ESI): m/z 1192.25 (M+H)$^+$.

Scheme 7. Synthesis of 8, 9

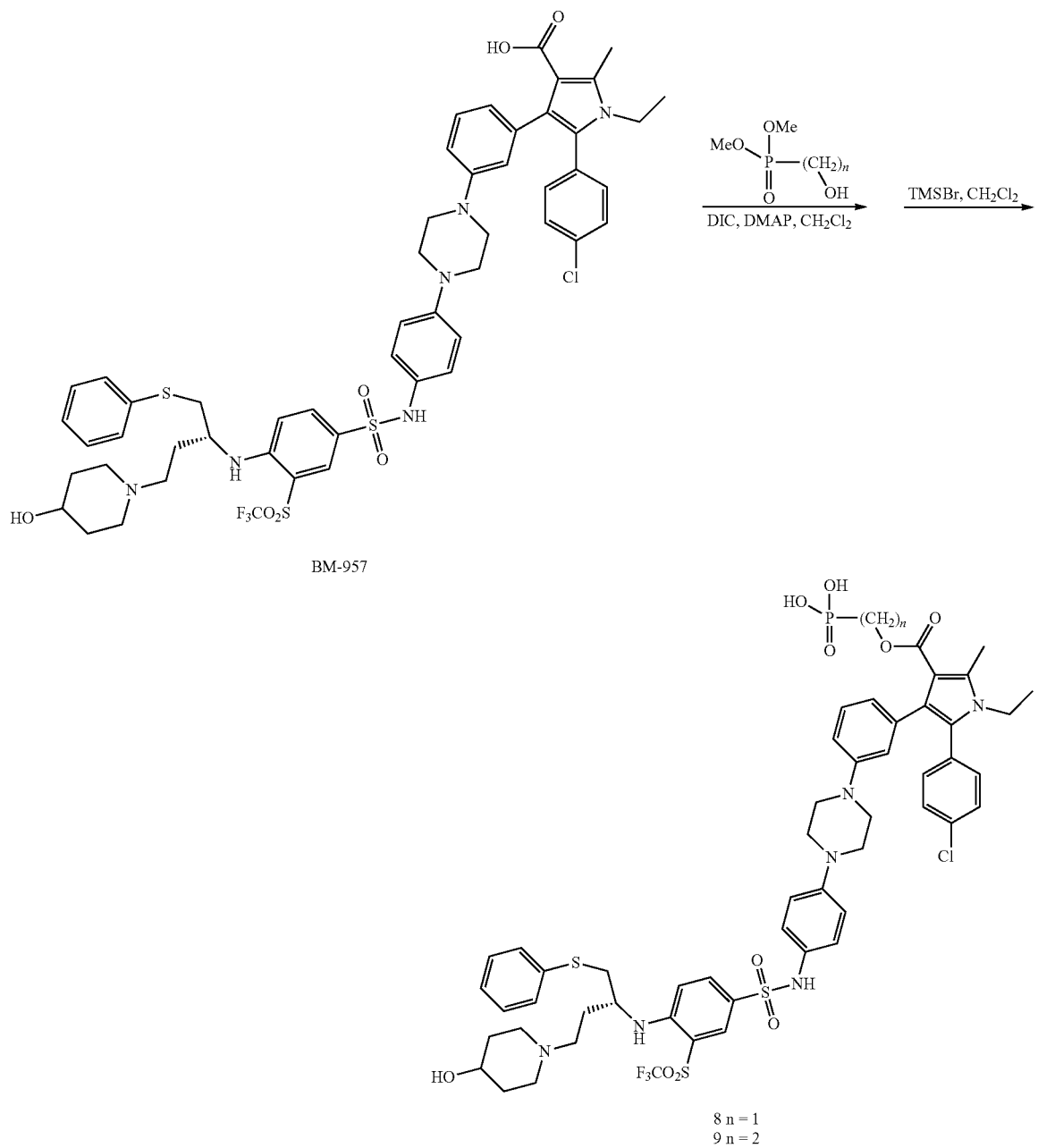

8 n = 1
9 n = 2

Experimental Section

General Procedure V (R)-(((5-(4-chlorophenyl)-1-ethyl-4-(3-(4-(4-(4-((4-(4-hydroxypiperidin-1-yl)-1-(phenylthio)butan-2-yl)amino)-3-((trifluoromethyl) sulfonyl)phenylsulfonamido)phenyl)piperazin-1-yl)phenyl)-2-methyl-1H-pyrrole-3-carbonyl)oxy)methyl)phosphonic acid (8)

To a solution of BM-957 (100 mg, 0.09 mmol), DIC (18 mg, 0.14 mmol) and DMAP (20 mg, 0.14 mmol) in DCM (2 mL) was added dimethyl (hydroxymethyl)phosphonate (40 mg, 0.28 mmol). The solution was stirred for 6 hours at room temperature until no BM-957 was observed by TLC. The reaction mixture was diluted with ethyl acetate (50 mL), washed with saturated NaHCO$_3$ solution (50 mL), brine (50 mL) and dried over sodium sulfate. The solvent was removed in vacuo to give crude product which was used for next step without purification. The resulting residue was dissolved in DCM (5 mL) and followed by adding TMSBr (248 uL, 1.9 mmol). The solution was stirred at room temperature for 20 h until no starting material was observed by MS. The reaction mixture was concentrated in vacuo and the residue was purified by HPLC to give the pure product 8 (salt with TFA, 74 mg, yield 68% over two steps). The gradient ran from 60% of solvent A and 40% of solvent B to 20% of solvent A and 80% of solvent B in 40 min. $^1$H NMR (300 M Hz, CD$_3$OD): δ 7.92 (s, 1H), 7.73-7.70 (m, 2H), 7.34-6.82 (m, 17H), 4.28 (d, J=8.6 Hz, 2H), 4.06-3.35 (m, 14H), 3.20-2.92 (m, 5H), 2.65 (s, 3H), 2.24-1.67 (m, 6H), 1.10 (t, J=7.0 Hz, 3H). MS (ESI): m/z 1259.50 (M+H)$^+$.

(R)-(2-((5-(4-chlorophenyl)-1-ethyl-4-(3-(4-(4-(4-((4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-2-methyl-1H-pyrrole-3-carbonyl)oxy)ethyl)phosphonic acid (9)
9 was prepared from BM-957 and dimethyl (2-hydroxyethyl)phosphonate according general procedure V. MS (ESI): m/z 1173.42 (M+H)$^+$.
Scheme 8. Synthesis of 10
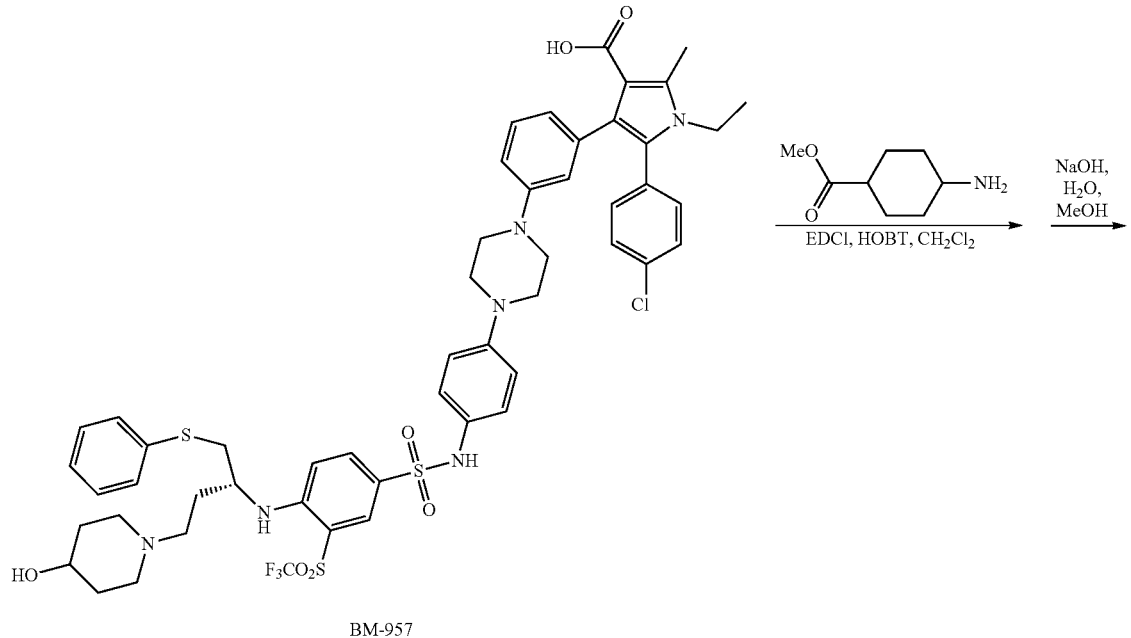
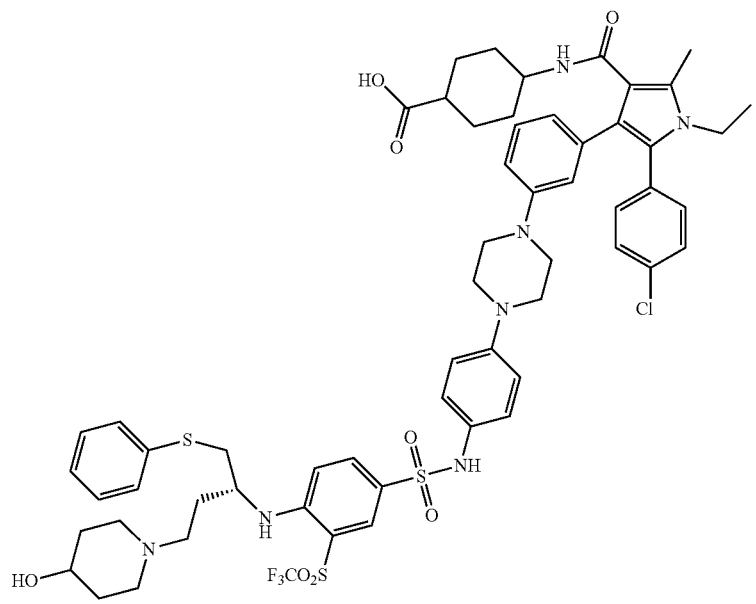

((R)-4-(5-(4-chlorophenyl)-1-ethyl-4-(3-(4-(4-(4-(4-(4-hydroxypiperidin-1-yl)-1-(phenylthio)butan-2-ylamino)-3-(trifluoromethylsulfonyl)phenylsulfonamido)phenyl)piperazin-1-yl)phenyl)-2-methyl-1H-pyrrole-3-carboxamido)cyclohexanecarboxylic acid (10)

To a solution of BM-957 (100 mg, 0.09 mmol), EDCI (27 mg, 0.14 mmol) and HOBT (19 mg, 0.14 mmol) in DCM (2 mL) was added methyl 4-aminocyclohexanecarboxylate (44 mg, 0.28 mmol). The solution was stirred for 2 hours at room temperature until no BM-957 was observed by TLC. The reaction mixture was diluted with ethyl acetate (50 mL), washed with saturated NaHCO$_3$ solution (50 mL), brine (50 mL) and dried over sodium sulfate. The solvent was removed in vacuo to give crude product which was used for next step without purification. The resulting residue was dissolved in H$_2$O and MeOH (5 mL and 5 mL respectively) and followed by adding NaOH (76 mg, 1.9 mmol). The solution was stirred at room temperature for 20 h until no starting material was observed by TLC. The reaction mixture was concentrated in vacuo and the residue was purified by HPLC to give the pure product 10 (salt with TFA, 61 mg, yield 55% over two steps). The gradient ran from 60% of solvent A and 40% of solvent B to 20% of solvent A and 80% of solvent B in 40 min. MS (ESI): m/z 1191.17 (M+H)$^+$.

Scheme 9. Synthesis of 11

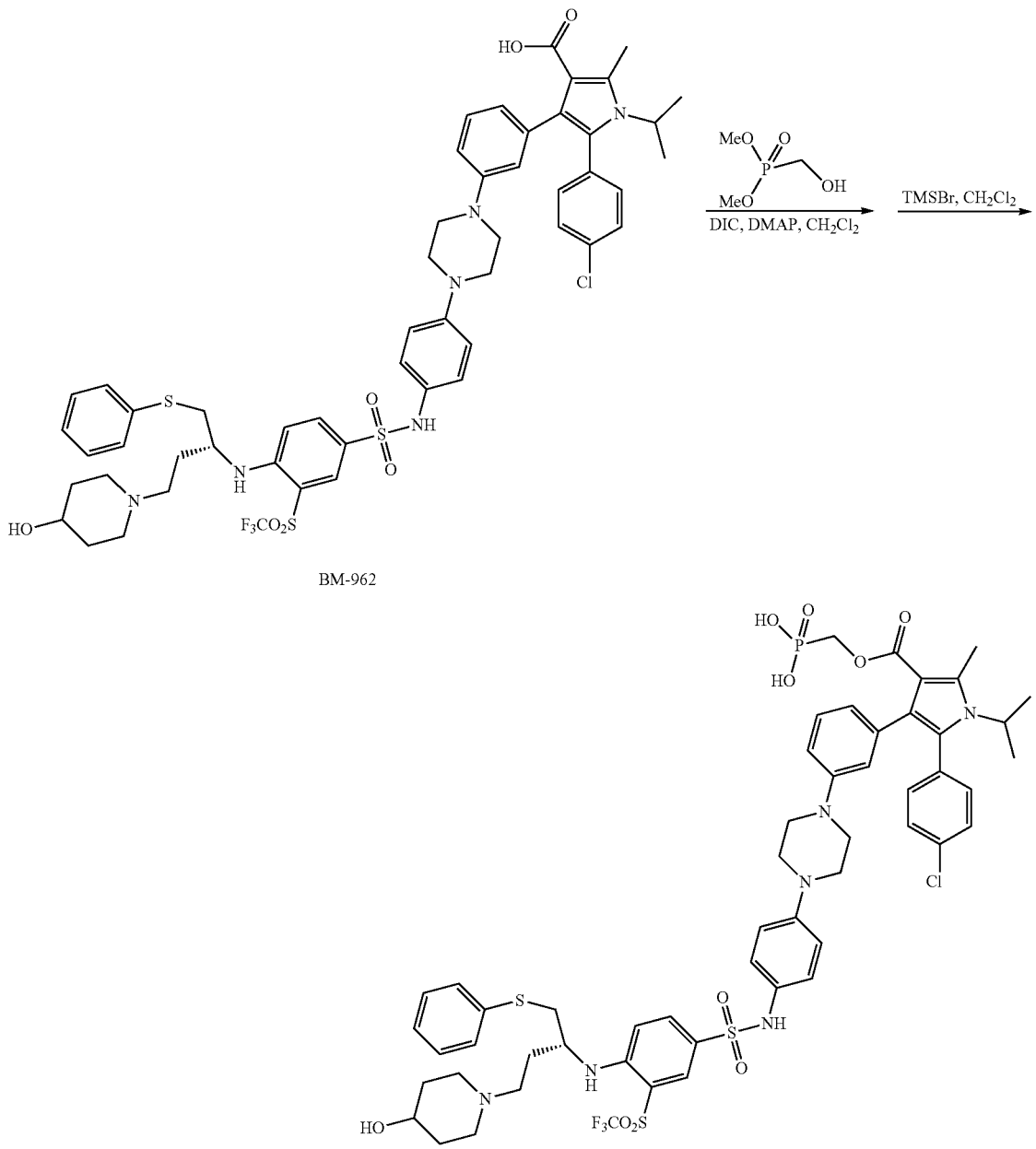

Experimental Section (R)-(((5-(4-chlorophenyl)-4-(3-(4-(4-(4-((4-(4-hydroxypiperidin-1-yl)-1-(phenylthio)butan-2-yl)amino)-3-((trifluoromethyl)sulfonyl)phenylsulfonamido)phenyl)piperazin-1-yl)phenyl)-1-isopropyl-2-methyl-1H-pyrrole-3-carbonyl)oxy)ethyl)phosphonic acid (11)

11 was prepared from BM-962 and dimethyl (hydroxymethyl)phosphonate according general procedure V. $^1$H NMR (300 M Hz, CD$_3$OD): δ 8.00 (s, 1H), 7.80-7.71 (m, 2H), 7.38-6.83 (m, 17H), 4.50-4.41 (m, 1H), 4.29 (d, J=8.7 Hz, 2H), 4.11-3.59 (m, 12H), 3.25-3.01 (m, 6H), 2.77 (s, 3H), 2.28-1.70 (m, 6H), 1.47 (d, J=7.1 Hz, 6H). MS (ESI): m/z 1174.25 (M+H)$^+$.

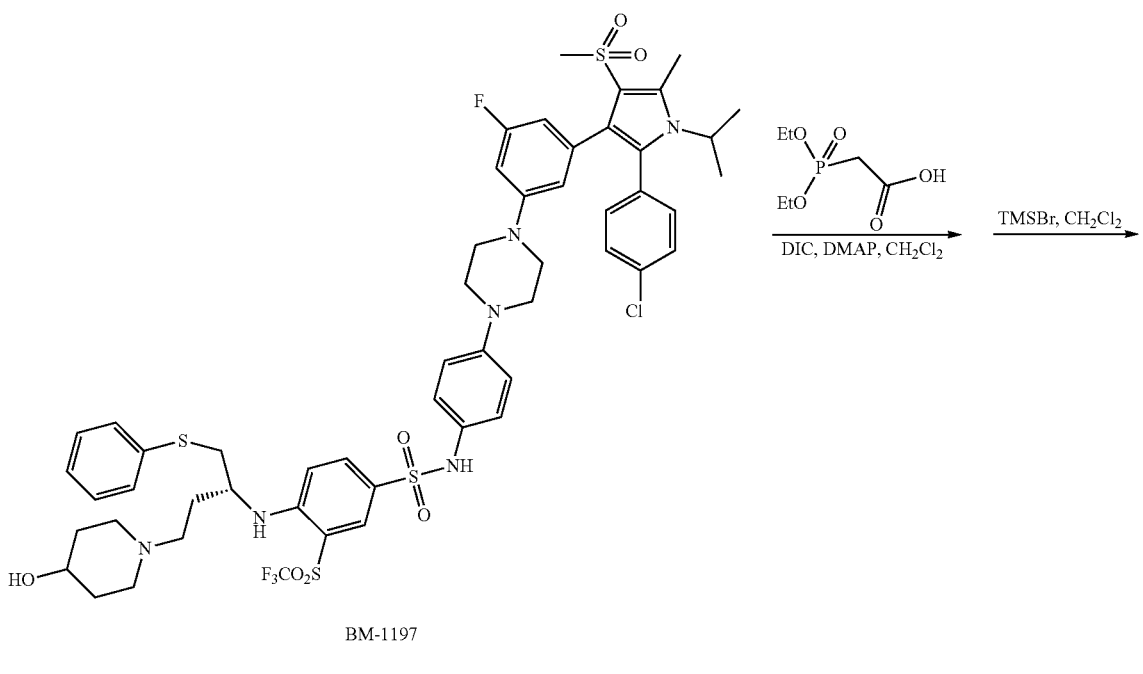

Scheme 8. Synthesis of 12

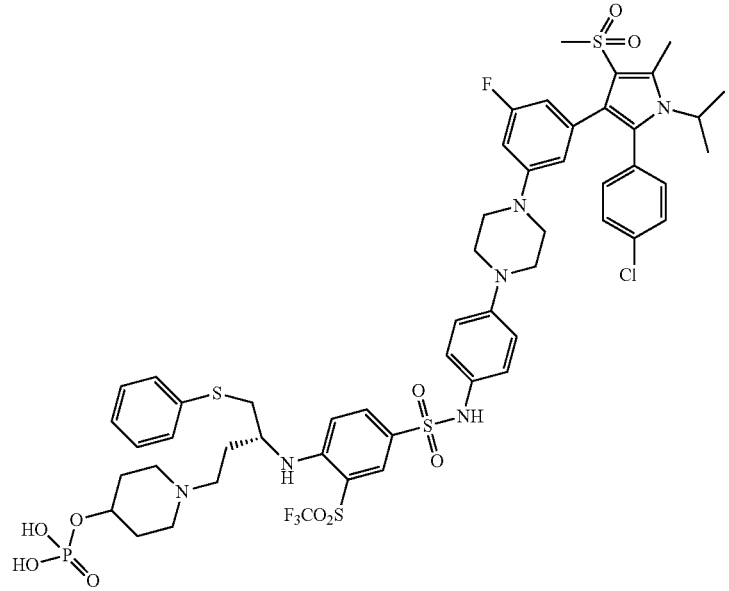

12

Experimental Section (R)-(2-((1-(3-((4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-((trifluoromethyl)sulfonyl)phenyl)amino)-4-(phenylthio)butyl)piperidin-4-yl)oxy)-2-oxoethyl) phosphonic acid (12)

12 was prepared from BM-1197 and 2-(diethoxyphosphoryl)acetic acid according to general procedure V. $^1$H NMR (300 M Hz, CD$_3$OD): δ 7.99 (s, 1H), 7.75 (d, J=8.6 Hz, 1H), 7.36-7.13 (m, 12H), 6.92-6.43 (m, 5H), 5.10 (s, 1H), 4.51-4.44 (m, 1H), 4.10 (s, 1H), 3.56-2.93 (m, 18H), 2.87 (s, 3H), 2.76 (s, 3H), 2.29-1.90 (m, 6H), 1.46 (d, J=7.3 Hz, 6H). MS (ESI): m/z 1253.36 (M+H)$^+$.

Experimental Section (R)-tert-butyl 1-(3-amino-4-(phenylthio)butyl)piperidine-4-carboxylate (K)

K was prepared from tert-butyl piperidine-4-carboxylate and D according to general procedure II. MS (ESI): m/z 365.50 (M+H)$^+$.

(R)-1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)piperidine-4-carboxylic acid (13)

13 was prepared from K and B according general procedure III. MS (ESI): m/z 365.50 (M+H)$^+$.

Scheme 10. Synthesis of 13

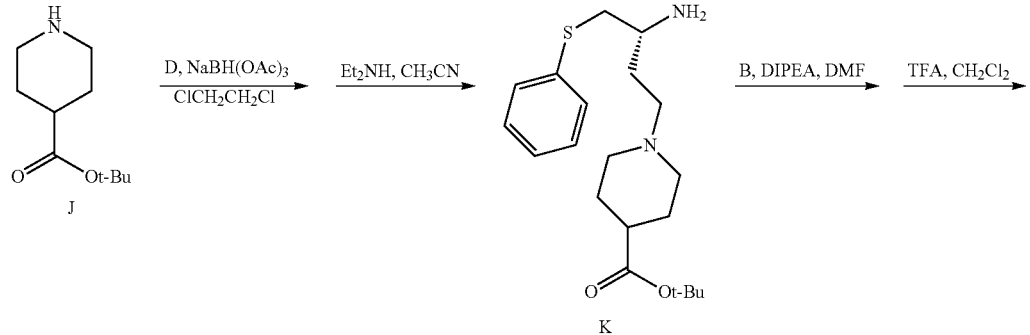

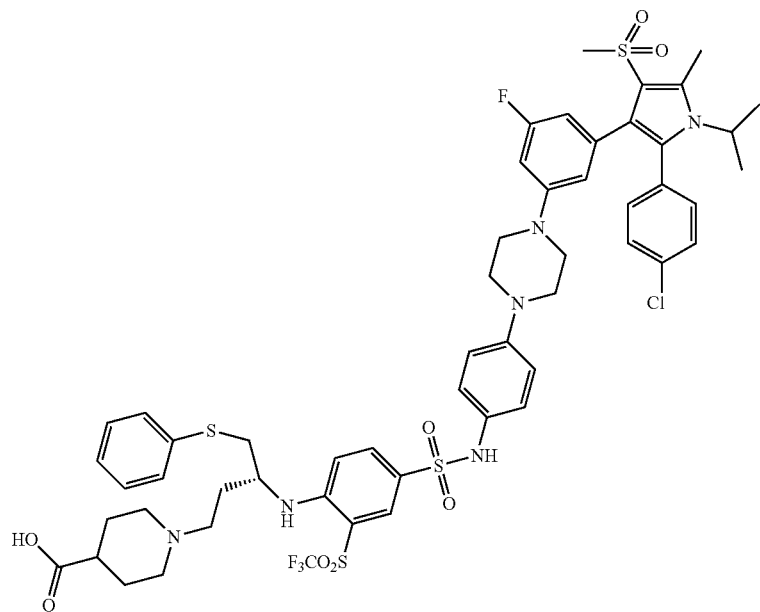

13

Scheme 11. Synthesis of 14, 15, 16, 17
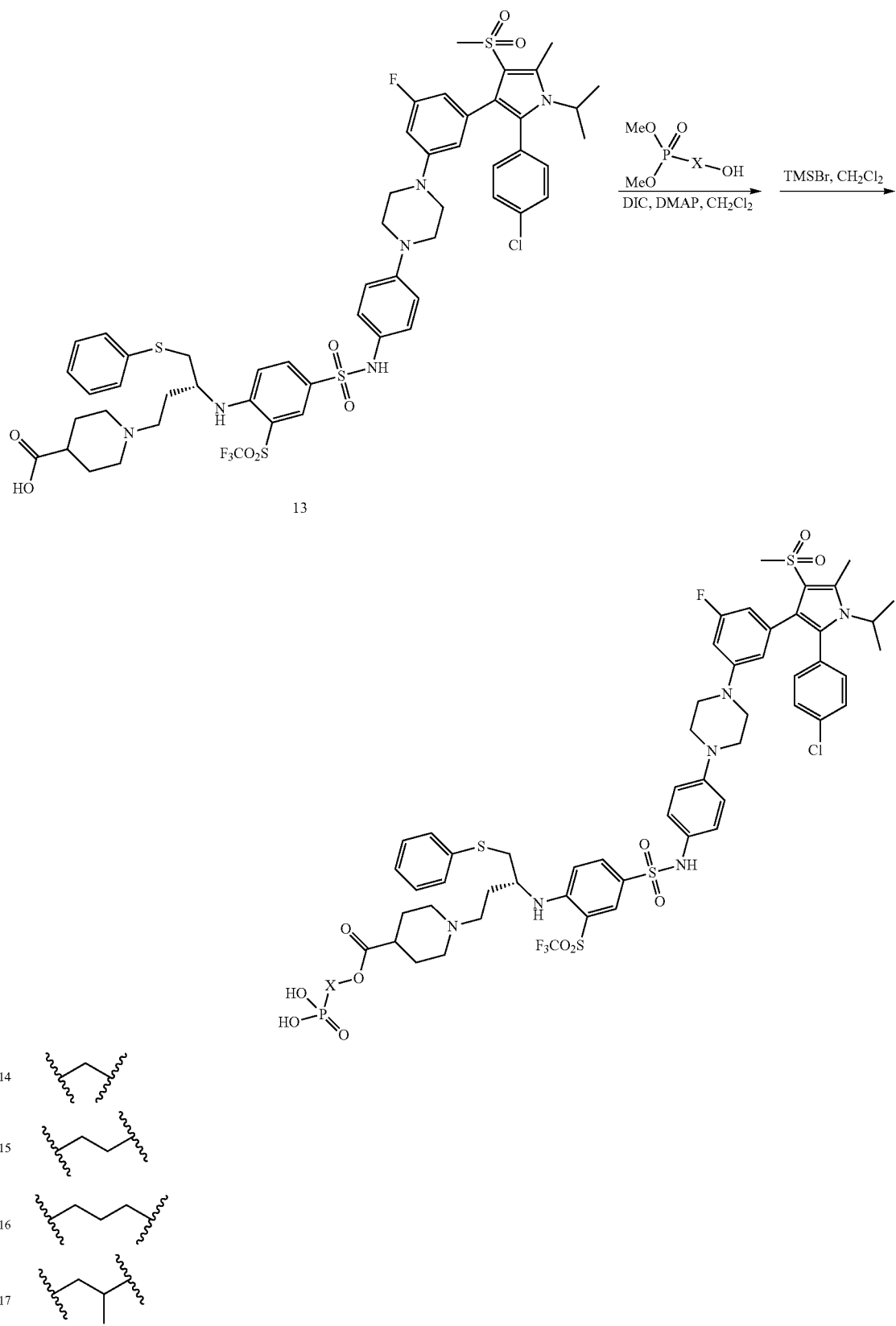

Experimental Section

(R)-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)piperidine-4-carbonyloxy) methylphosphonic acid (14)

14 was prepared from 13 and dimethyl (2-hydroxymethyl) phosphonate according to general procedure V. $^1$H NMR (300 M Hz, CD$_3$OD): δ 7.94 (s, 1H), 7.72 (d, J=9.1 Hz, 1H), 7.30-7.09 (m, 13H), 6.91-6.42 (m, 4H), 4.49-4.40 (m, 1H), 3.99 (s, 1H), 3.55-2.90 (m, 16H), 2.84 (s, 3H), 2.72 (s, 3H), 2.63-2.55 (m, 1H), 2.23-1.81 (m, 6H), 1.41 (d, J=4.3 Hz, 6H). MS (ESI): m/z 1160.34 (M+H)$^+$.

(R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)piperidine-4-carbonyloxy) ethylphosphonic acid (15)

15 was prepared from 13 and dimethyl (2-hydroxyethyl) phosphonate according to general procedure V. $^1$H NMR (300 M Hz, CD$_3$OD): δ 7.93 (d, J=1.9 Hz, 1H), 7.72 (dd, J=9.2, 1.8 Hz, 1H), 7.30-7.12 (m, 12H), 6.83-6.42 (m, 5H), 4.46-4.33 (m, 3H), 3.96 (s, 1H), 3.54-2.93 (m, 16H), 2.82 (s, 3H), 2.72 (s, 3H), 2.71-2.55 (m, 1H), 2.24-1.65 (m, 8H), 1.41 (d, J=7.1 Hz, 6H). MS (ESI): m/z 1268.58 (M+H)$^+$.

(R)-3-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)piperidine-4-carbonyloxy) propylphosphonic acid (16)

16 was prepared from 13 and dimethyl 3-hydroxypropylphosphonate according to general procedure V. $^1$H NMR (300 M Hz, CD$_3$OD): δ 7.95 (d, J=2.0 Hz, 1H), 7.73 (dd, J=9.2, 2.1 Hz, 1H), 7.33-7.12 (m, 12H), 6.92-6.43 (m, 5H), 4.51-4.41 (m, 1H), 4.18-3.98 (m, 3H), 3.56-2.92 (m, 16H), 2.85 (s, 3H), 2.73 (s, 3H), 2.67-2.50 (m, 1H), 2.25-1.70 (m, 10H), 1.43 (d, J=7.1 Hz, 6H). MS (ESI): m/z 1282.34 (M+H)$^+$.

2-(1-((R)-3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)piperidine-4-carbonyloxy) propylphosphonic acid (17)

17 was prepared from 13 and dimethyl 2-hydroxypropylphosphonate according to general procedure V. $^1$H NMR (300 M Hz, CD$_3$OD): δ 7.97 (d, J=2.1 Hz, 1H), 7.73 (d, J=9.2 Hz, 1H), 7.36-7.08 (m, 13H), 6.85-6.43 (m, 4H), 5.26 (s, 1H), 4.54-4.44 (m, 1H), 4.01 (s, 1H), 3.58-2.92 (m, 16H), 2.87 (s, 3H), 2.76 (s, 3H), 2.70-2.55 (m, 1H), 2.26-1.85 (m, 8H), 1.46 (d, J=7.1 Hz, 6H), 1.38 (d, J=5.9 Hz, 3H). MS (ESI): m/z 1281.34 (M+H)$^+$.

Scheme 12. Synthesis of 18

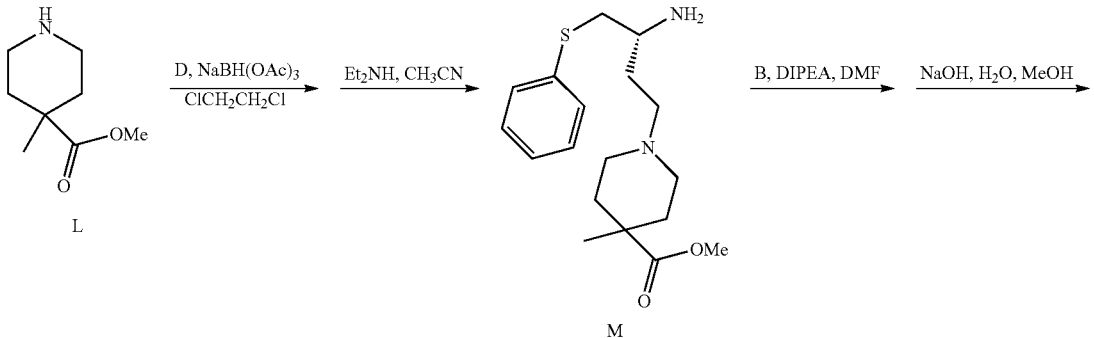

-continued

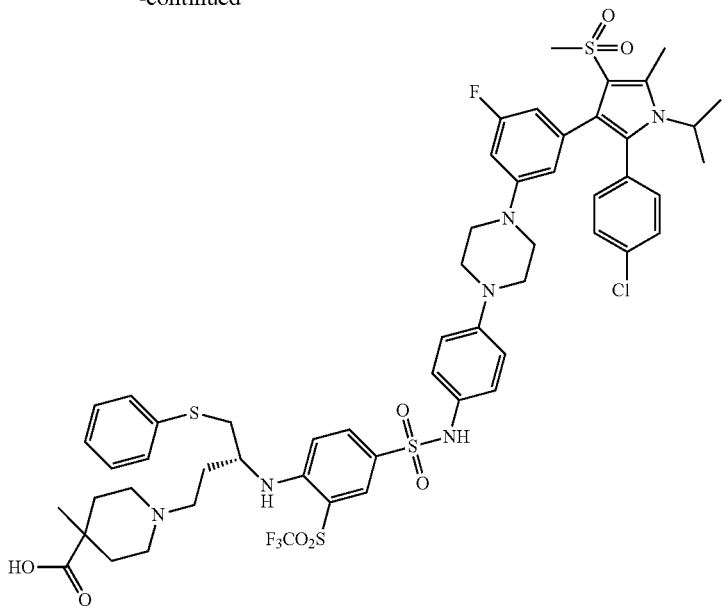

18

Experimental Section

(R)-methyl 1-(3-amino-4-(phenylthio)butyl)-4-methylpiperidine-4-carboxylate (M)

M was prepared from methyl 4-methylpiperidine-4-carboxylate and D according general procedure II. MS (ESI): m/z 337.55 (M+H)$^+$.

(R)-1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)-4-methylpiperidine-4-carboxylic acid (18)

To a solution of B (100 mg, 0.11 mmol) and M (47 mg, 0.14 mmol) in DMF (2 mL) was added DIPEA (1 mL). The solution was stirred for 4 hours at room temperature until no B was observed by TLC. The reaction mixture was concentrated in vacuo to give crude product which was used for next step without purification. The resulting residue was dissolved in H$_2$O and MeOH (5 mL and 5 mL respectively) and followed by adding NaOH (88 mg, 2.2 mmol). The solution was stirred at room temperature for 20 h until no starting material was observed by TLC. The reaction mixture was concentrated in vacuo and the residue was purified by HPLC to give the pure product 18 (salt with TFA, 75 mg, yield 58% over two steps). The gradient ran from 60% of solvent A and 40% of solvent B to 20% of solvent A and 80% of solvent B in 40 min. $^1$H NMR (300 M Hz, CD$_3$OD): δ 7.99 (d, J=1.6 Hz, 1H), 7.76 (dd, J=9.1, 1.9 Hz, 1H), 7.37-6.84 (m, 14H), 6.68-6.45 (m, 3H), 4.55-4.45 (m, 1H), 4.02 (s, 1H), 3.58-2.92 (m, 17H), 2.88 (s, 3H), 2.77 (s, 3H), 2.41-1.86 (m, 5H), 1.47 (d, J=7.1 Hz, 6H), 1.31 (s, 3H). MS (ESI): m/z 1173.73 (M+H)$^+$.

Scheme 13. Synthesis of 19
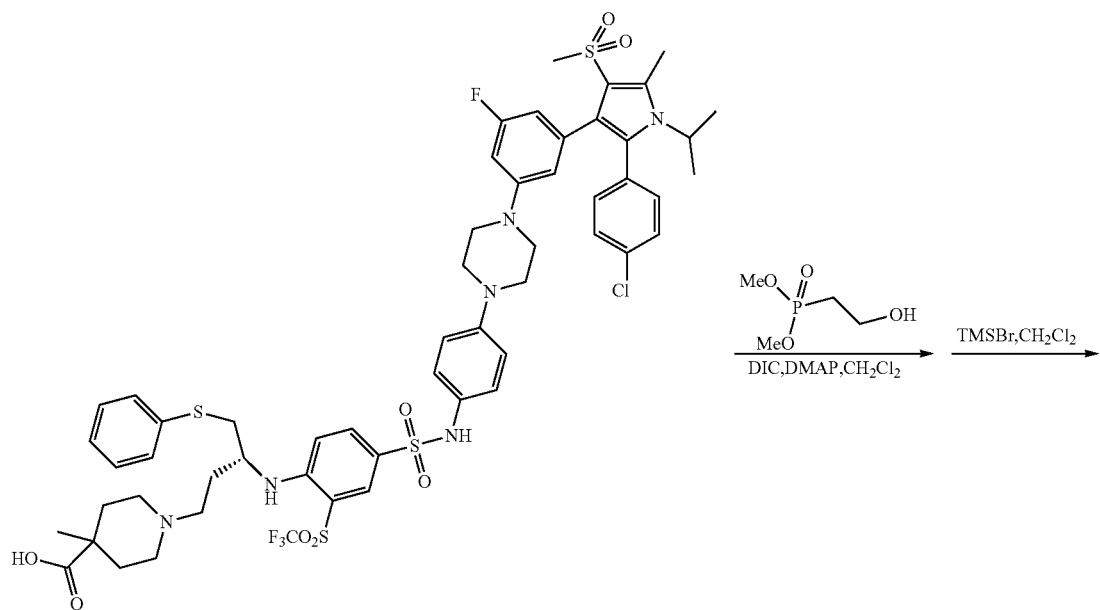
18
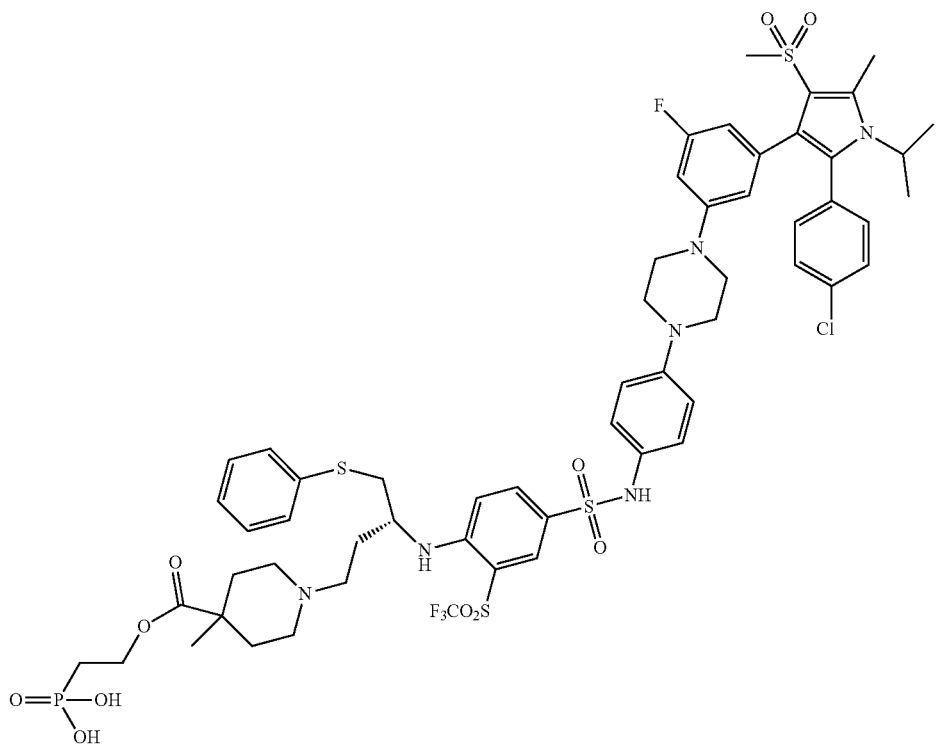
19

Experimental Section (R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)-4-methylpiperidine-4-carbonyloxy)ethylphosphonic acid (19)

19 was prepared from 18 and dimethyl (2-hydroxyethyl) phosphonate according to general procedure V. $^{1}$H NMR (300 M Hz, CD$_3$OD): δ 7.98 (d, J=1.6 Hz, 1H), 7.73 (dd, J=9.2, 2.0 Hz, 1H), 7.35-6.83 (m, 14H), 6.65-6.44 (m, 3H), 4.52-4.38 (m, 3H), 4.01 (s, 1H), 3.44-2.92 (m, 17H), 2.87 (s, 3H), 2.77 (s, 3H), 2.45-2.11 (m, 5H), 1.71 (t, J=14.4 Hz, 2H), 1.46 (d, J=7.1 Hz, 6H), 1.30 (s, 3H). MS (ESI): m/z 1281.92 (M+H)$^+$.

Experimental Section (R)-3-(((9H-fluoren-9-yl)methoxy)carbonylamino)-4-(2-fluorophenylthio)butanoic acid (O)

A solution of Bu$_3$P (0.8 mL, 3.3 mmol) and ADDP (833 mg, 3.3 mmol) in THF (30 mL) was treated with N (1.2 g, 3.0 mmol) and thiophenol (320 uL, 3.0 mmol), stirred for 4 h until no N was observed by TLC. The mixture was diluted with ethyl acetate (100 mL), washed with 1M HCl aqueous (100 mL), brine (100 mL) and dried over sodium sulfate. The solvent was removed in vacuo to give crude product which was used for next step without purification. The resulting residue was dissolved in DCM (10 mL) and followed by

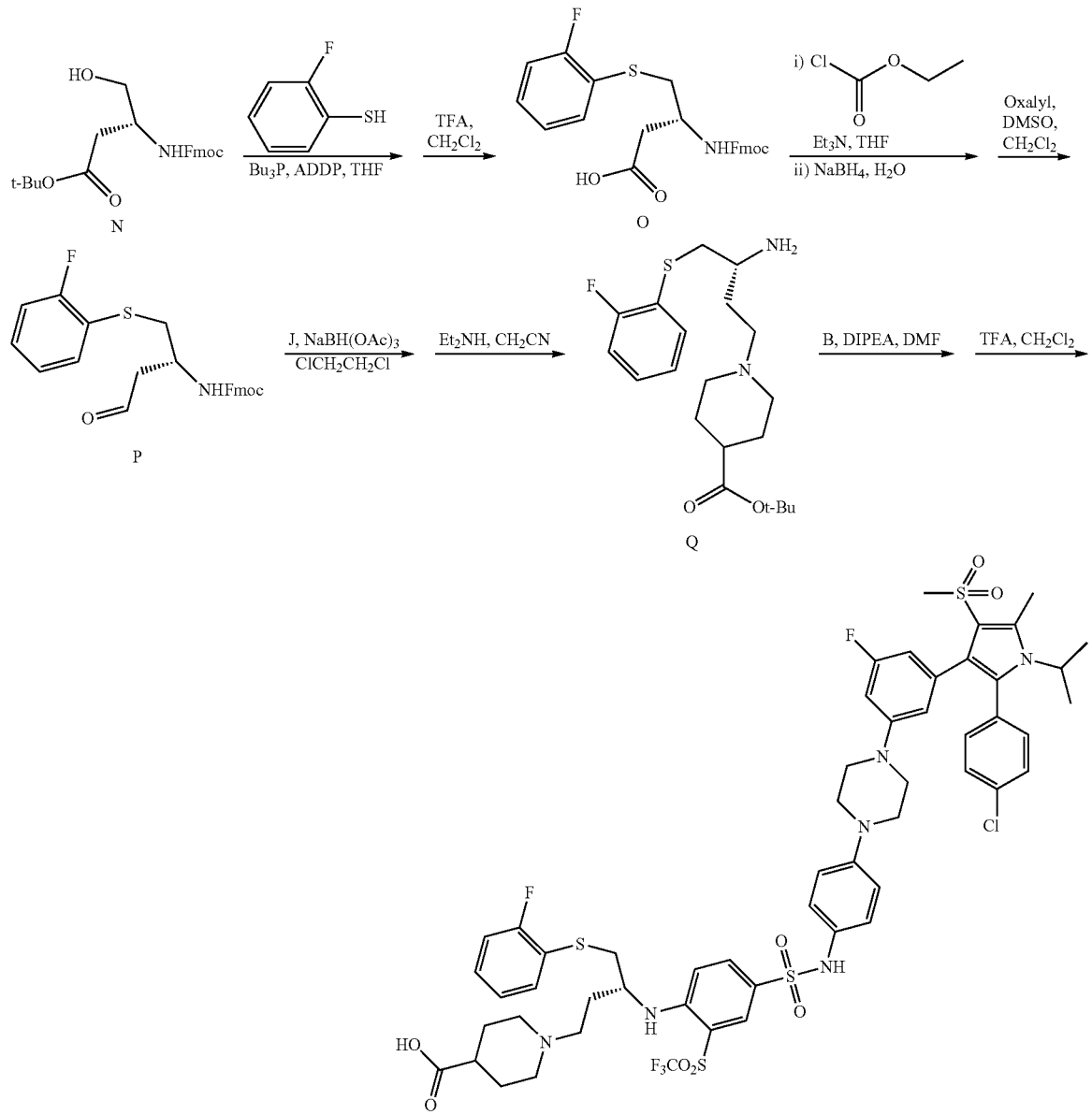

Scheme 14. Synthesis of compound 20 adding TFA (5 mL). The solution was stirred at room temperature for 1 h until no starting material was observed by TLC. The reaction mixture was concentrated in vacuo and the residue was flash chromatographed on silica gel with 5% MeOH/DCM to provide intermediate O (840 mg, yield 62% over two steps). MS (ESI) m/z 452.86 (M+H)$^+$.

(R)-(9H-fluoren-9-yl)methyl 1-(2-fluorophenylthio)-4-oxobutan-2-ylcarbamate (P)

P was prepared from O according to general procedure I. MS (ESI) m/z 437.00 (M+H)$^+$.

(R)-tert-butyl 1-(3-amino-4-(2-fluorophenylthio) butyl)piperidine-4-carboxylate (Q)

Q was prepared from P and J according to general procedure II. MS (ESI) m/z 383.38 (M+H)$^+$.

(R)-1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(2-fluorophenylthio)butyl)piperidine-4-carboxylic acid (20)

20 was prepared from Q and B according to general procedure III. $^1$H NMR (300 M Hz, CD$_3$OD): δ 7.97 (d, J=1.9 Hz, 1H), 7.76 (dd, J=9.2, 2.0 Hz, 1H), 7.39-6.87 (m, 13H), 6.65-6.43 (m, 3H), 4.54-4.45 (m, 1H), 4.01 (s, 1H), 3.67-2.93 (m, 17H), 2.87 (s, 3H), 2.77 (s, 3H), 2.29-1.86 (m, 6H), 1.46 (d, J=7.1 Hz, 6H). MS (ESI): m/z 1177.92 (M+H)$^+$.

Scheme 15. Synthesis of 21

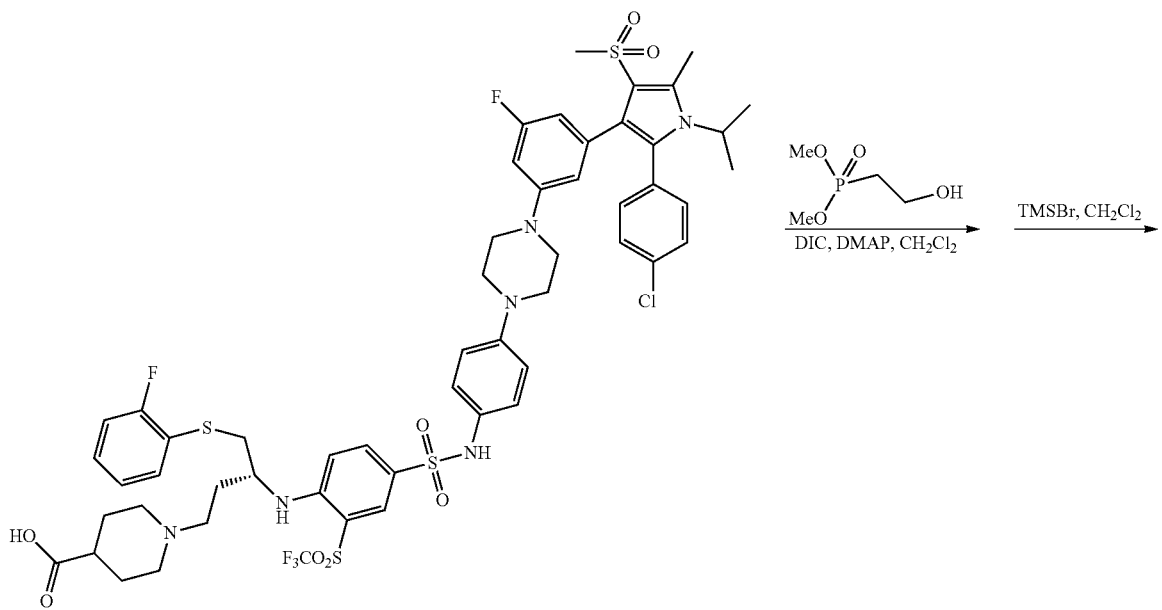

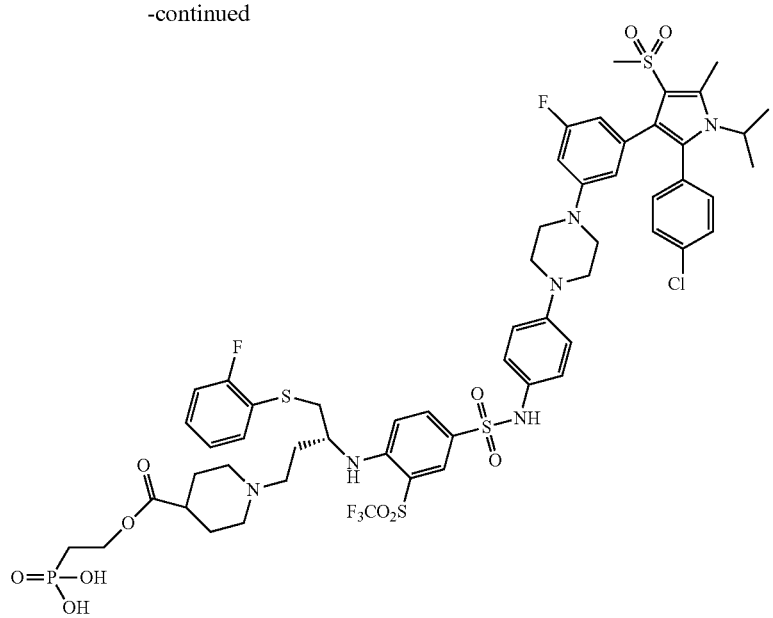

21

Experimental Section (R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(2-fluorophenylthio)butyl)piperidine-4-carbonyloxy)ethylphosphonic acid (21)

21 was prepared from 20 and dimethyl (2-hydroxyethyl) phosphonate according to general procedure V. $^1$H NMR (300 MHz, CD$_3$OD): δ 7.95 (d, J=1.7 Hz, 1H), 7.77 (dd, J=9.0, 2.0 Hz, 1H), 7.36-6.86 (m, 13H), 6.66-6.44 (m, 3H), 4.51-4.33 (m, 3H), 4.01 (s, 1H), 3.58-2.93 (m, 16H), 2.85 (s, 3H), 2.74 (s, 3H), 2.70-2.58 (m, 1H), 2.27-1.84 (m, 8H), 1.43 (d, J=7.1 Hz, 6H). MS (ESI): m/z 1286.58 (M+H)$^+$.

Scheme 16. Synthesis of 22

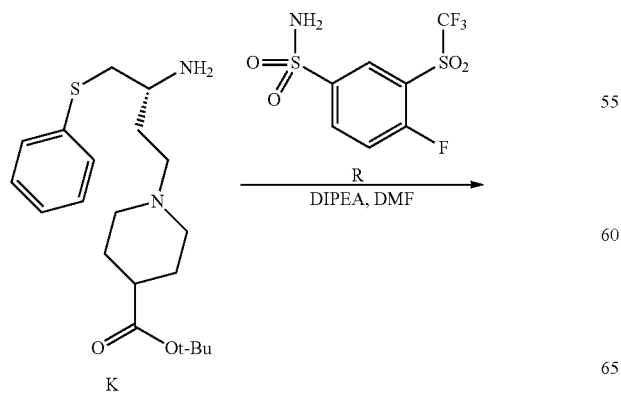

K

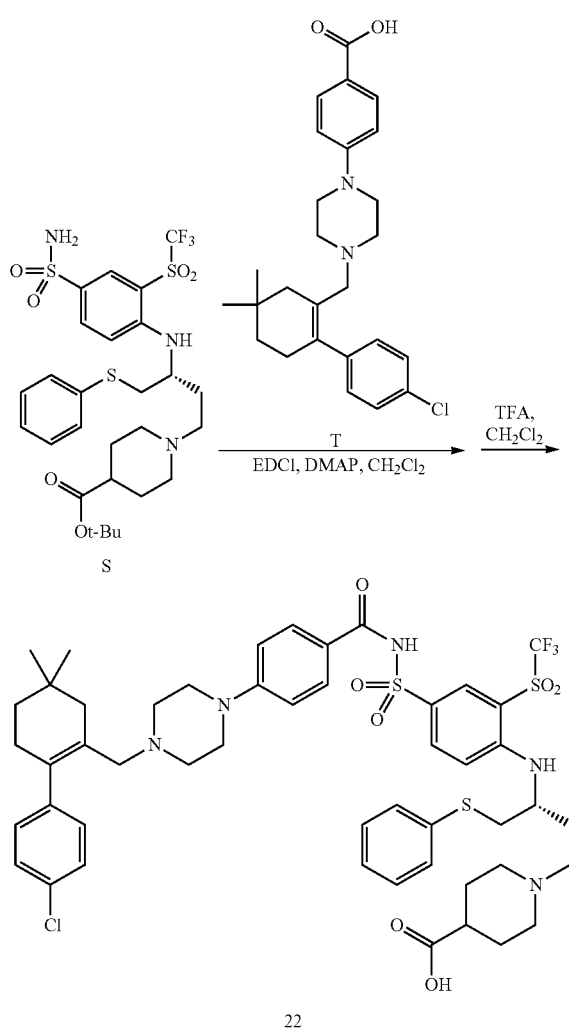

Experimental Section

(R)-tert-butyl 1-(4-(phenylthio)-3-(4-sulfamoyl-2-(trifluoromethylsulfonyl)phenyl amino)butyl)piperidine-4-carboxylate (S)

To a solution of K (1.1 g, 3.0 mmol) and R (922 mg, 3.0 mmol) in DMF (15 mL) was added DIPEA (3 mL). The solution was stirred for 4 hours at room temperature until no K was observed by TLC. The reaction mixture was concentrated in vacuo and the residue was flash chromatographed on silica gel with 5% MeOH/DCM to provide intermediate S (1.7 g, yield 88% over two steps). MS (ESI) m/z 653.21 (M+H)$^+$.

(R)-1-(3-(4-(N-(4-(4-((2-(4-chlorophenyl)-5,5-dimethylcyclohex-1-enyl)methyl) piperazin-1-yl)benzoyl)sulfamoyl)-2-(trifluoromethylsulfonyl)phenylamino)-4-(phenylthio)butyl)piperidine-4-carboxylic acid (22)

To a solution of T (438 mg, 1.0 mmol), EDCI (386 mg, 2.0 mmol) and DMAP (121 mg, 1.0 mmol) in DCM (10 mL) was added S (718 mg, 1.1 mmol). The solution was stirred for 2 hours at room temperature until no T was observed by TLC. The reaction mixture was diluted with ethyl acetate (50 mL), washed with saturated NaHCO$_3$ solution (50 mL), brine (50 mL) and dried over sodium sulfate. The solvent was removed in vacuo to give crude product which was used for next step without purification. The resulting residue was dissolved in DCM (10 mL) and followed by adding TFA (5 mL). The solution was stirred at room temperature for 1 h until no starting material was observed by TLC. The reaction mixture was concentrated in vacuo and the residue was purified by HPLC to give the pure product 22 (salt with TFA, 742 mg, yield 73% over two steps). The gradient ran from 60% of solvent A and 40% of solvent B to 20% of solvent A and 80% of solvent B in 40 min. $^1$H NMR (300 M Hz, CD$_3$OD): δ 8.30 (d, J=2.1 Hz, 1H), 8.02 (dd, J=9.2, 2.5 Hz, 1H), 7.70 (d, J=8.9 Hz, 2H), 7.40-6.88 (m, 12H), 4.04 (s, 1H), 3.67-2.82 (m, 19H), 2.58 (t, J=14.4 Hz, 1H), 2.37-1.81 (m, 10H), 1.53 (t, J=6.2 Hz, 2H), 1.03 (s, 6H). MS (ESI): m/z 1017.50 (M+H)$^+$.

Scheme 17. Synthesis of 23, 24, 25

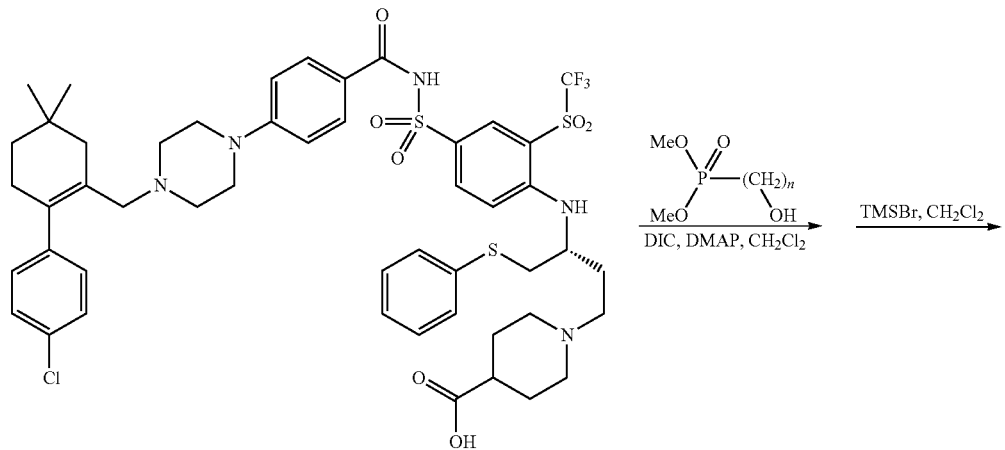

22

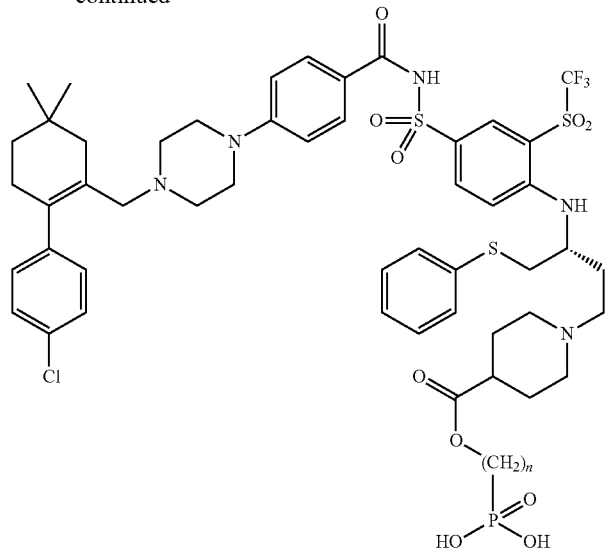

23 n = 1
24 n = 2
25 n = 3

Experimental Section (R)-(1-(3-(4-(N-(4-(4-((2-(4-chlorophenyl)-5,5-dimethylcyclohex-1-enyl)methyl)piperazin-1-yl)benzoyl)sulfamoyl)-2-(trifluoromethylsulfonyl)phenylamino)-4-(phenylthio)butyl)piperidine-4-carbonyloxy)methylphosphonic acid (23)

23 was prepared from 22 and dimethyl (2-hydroxymethyl) phosphonate according general procedure V. $^1$H NMR (300 MHz, CD$_3$OD): δ 8.35 (s, 1H), 8.09 (d, J=6.7 Hz, 1H), 7.79 (d, J=7.7 Hz, 2H), 7.44-6.82 (m, 12H), 4.30-4.10 (m, 3H), 3.74-2.73 (m, 19H), 2.43-1.44 (m, 12H), 1.10 (s, 6H). MS (ESI): m/z 1110.58 (M+H)$^+$.

(R)-2-(1-(3-(4-(N-(4-(4-((2-(4-chlorophenyl)-5,5-dimethylcyclohex-1-enyl)methyl) piperazin-1-yl) benzoyl)sulfamoyl)-2-(trifluoromethylsulfonyl)phenylamino)-4-(phenylthio)butyl)piperidine-4-carbonyloxy)ethylphosphonic acid (24)

24 was prepared from 22 and dimethyl (2-hydroxyethyl) phosphonate according general procedure V. $^1$H NMR (300 MHz, CD$_3$OD): δ 8.29 (d, J=2.0 Hz, 1H), 8.02 (dd, J=9.2, 2.0 Hz, 1H), 7.71 (d, J=8.8 Hz, 2H), 7.37-6.84 (m, 12H), 4.34-4.30 (m, 2H), 4.03 (s, 1H), 3.66-2.88 (m, 18H), 2.62 (t, J=14.4 Hz, 1H), 2.36-1.82 (m, 12H), 1.53 (t, J=6.1 Hz, 2H), 1.03 (s, 6H). MS (ESI): m/z 1025.64 (M+H)$^+$.

(R)-3-(1-(3-(4-(N-(4-(4-((2-(4-chlorophenyl)-5,5-dimethylcyclohex-1-enyl)methyl) piperazin-1-yl) benzoyl)sulfamoyl)-2-(trifluoromethylsulfonyl)phenylamino)-4-(phenylthio)butyl)piperidine-4-carbonyloxy)propylphosphonic acid (25)

25 was prepared from 22 and dimethyl 3-hydroxypropylphosphonate according general procedure V. $^1$H NMR (300 MHz, CD$_3$OD): δ 7.95 (d, J=2.0 Hz, 1H), 7.73 (dd, J=9.2, 2.1 Hz, 1H), 7.33-7.12 (m, 12H), 6.92-6.43 (m, 5H), 4.51-4.41 (m, 1H), 4.18-3.98 (m, 3H), 3.56-2.92 (m, 16H), 2.85 (s, 3H), 2.73 (s, 3H), 2.67-2.50 (m, 1H), 2.25-1.70 (m, 10H), 1.43 (d, J=7.1 Hz, 6H). MS (ESI): m/z 1282.34 (M+H)$^+$.

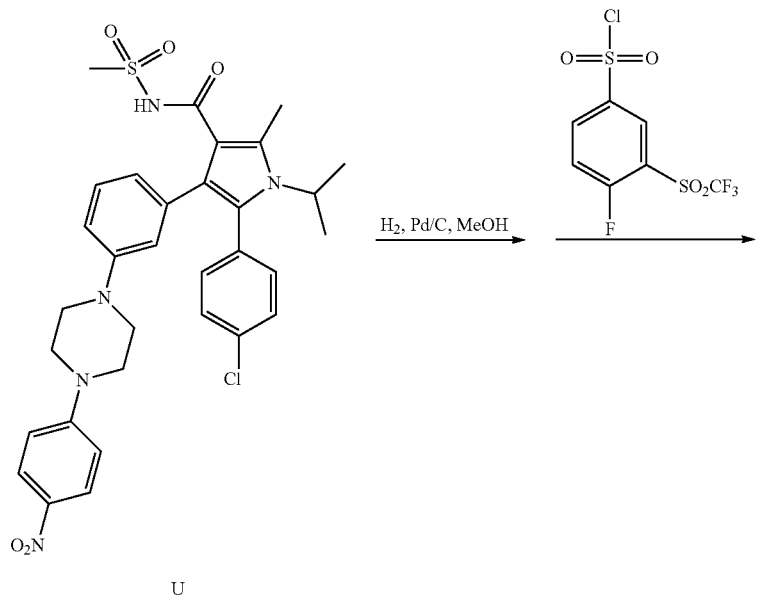
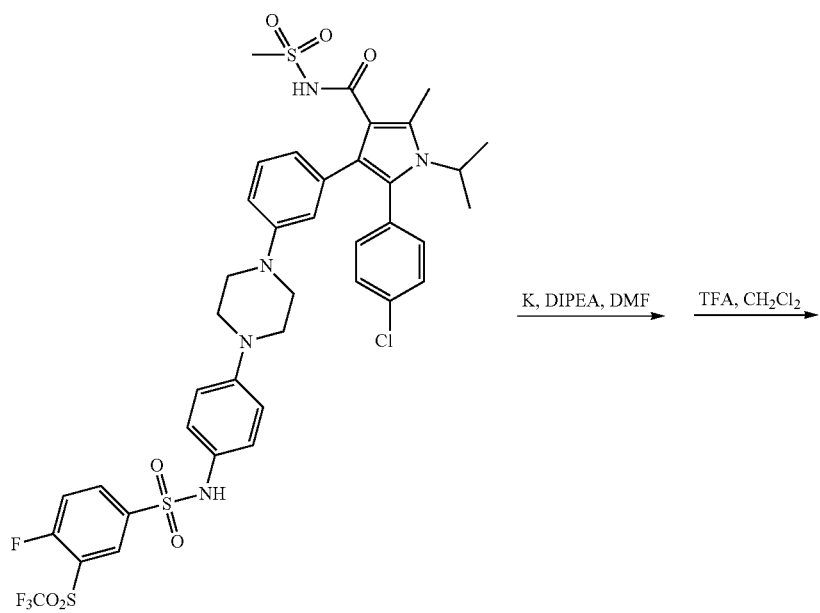

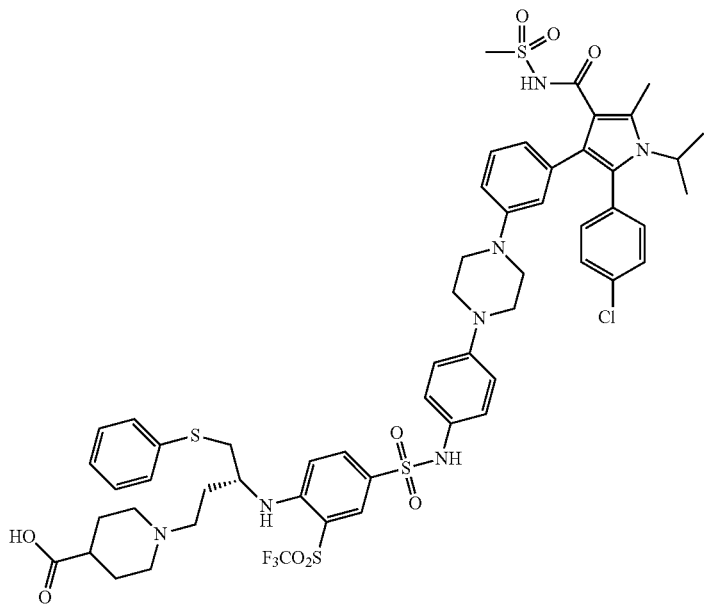

26

5-(4-chlorophenyl)-4-(3-(4-(4-(4-fluoro-3-(trifluoromethylsulfonyl)phenylsulfonamido)phenyl)piperazin-1-yl)phenyl)-1-isopropyl-2-methyl-N-(methylsulfonyl)-1H-pyrrole-3-carboxamide (V)

V was prepared from U according to the procedure described for the preparation of compound B.

(R)-1-(3-(4-(N-(4-(4-(3-(2-(4-chlorophenyl)-1-isopropyl-5-methyl-4-(methylsulfonylcarbamoyl)-1H-pyrrol-3-yl)phenyl)piperazin-1-yl)phenyl)sulfamoyl)-2-(trifluoromethylsulfonyl)phenylamino)-4-(phenylthio)butyl)piperidine-4-carboxylic acid (26) (BM-1077)

26 was prepared from K and V according to general procedure III. $^1$H NMR (300 M Hz, CD$_3$OD): δ 7.94 (d, J=1.7 Hz, 1H), 7.71 (dd, J=2.0, 9.2 Hz, 1H), 7.39-7.28 (m, 4H), 7.26-7.14 (m, 6H), 7.09-6.96 (m, 5H), 6.93-6.85 (m, 2H), 6.81 (d, J=9.3 Hz, 1H), 6.75 (d, J=7.6 Hz, 1H), 4.41 (quintet, J=7.0 Hz, 1H), 4.06-3.88 (m, 1H), 3.66-3.33 (m, 8H), 3.25-2.79 (m, 10H), 2.63 (s, 3H), 2.36-1.71 (m, 8H), 1.43 (d, J=7.1 Hz, 6H). MS (ESI): m/z 1184.42 (M+H)$^+$.

(R)-2-(1-(3-(4-(N-(4-(4-(3-(2-(4-chlorophenyl)-1-isopropyl-5-methyl-4-(methylsulfonylcarbamoyl)-1H-pyrrol-3-yl)phenyl)piperazin-1-yl)phenyl)sulfamoyl)-2-(trifluoromethylsulfonyl)phenylamino)-4-(phenylthio)butyl)piperidine-4-carbonyloxy)ethylphosphonic acid (27) (BM-1080)

27 was prepared from 26 and dimethyl (2-hydroxyethyl) phosphonate according general procedure V. $^1$H NMR (300 M Hz, CD$_3$OD): δ7.95 (d, J=1.9 Hz, 1H), 7.69 (dd, J=1.8, 9.3 Hz, 1H), 7.39-7.28 (m, 4H), 7.27-7.12 (m, 6H), 7.08-6.76 (m, 8H), 6.70 (d, J=7.5 Hz, 1H), 4.49-4.27 (m, 3H), 4.04-3.89 (m, 1H), 3.65-3.48 (m, 2H), 3.29-2.84 (m, 15H), 2.63 (s, 3H), 2.37-1.74 (m, 11H), 1.43 (d, J=7.1 Hz, 6H). MS (ESI): m/z 1292.00 (M+H)$^+$.

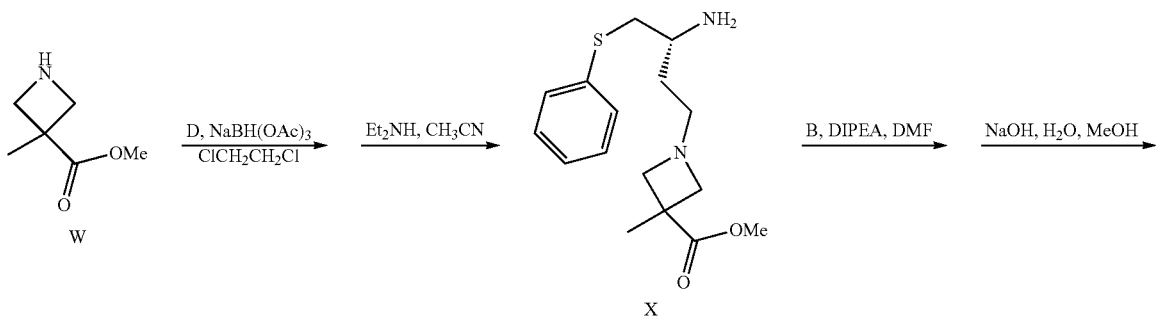

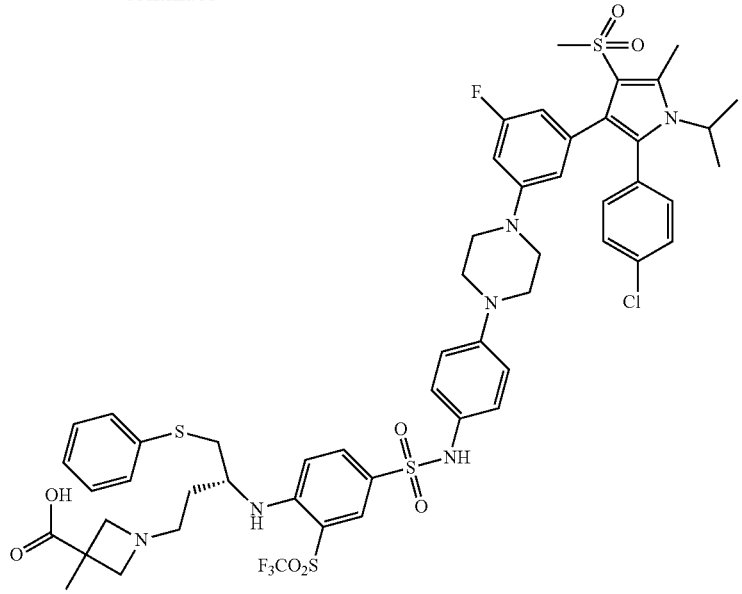

28

(R)-methyl 1-(3-amino-4-(phenylthio)butyl)-3-methylazetidine-3-carboxylate (X)

X was prepared from methyl 3-methylazetidine-3-carboxylate (W), and D according to general procedure II.

(R)-1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)-3-methylazetidine-3-carboxylic acid (28) (BM-1082)

28 was prepared from X and B according to the procedure described for the preparation of compound 18. $^1$H NMR (300 M Hz, CD$_3$OD): δ 7.94 (d, J=1.9 Hz, 1H), 7.70 (dd, J=2.1, 9.1 Hz, 1H), 7.35-7.24 (m, 4H), 7.23-7.12 (m, 5H), 7.07-6.91 (m, 4H), 6.87 (d, J=9.0 Hz, 1H), 6.81 (d, J=9.3 Hz, 1H), 6.63-6.47 (m, 2H), 6.41 (d, J=9.0 Hz, 1H), 4.55-4.38 (m, 2H), 3.97 (br. s., 3H), 3.29-3.08 (m, 13H), 2.84 (s, 3H), 2.74 (s, 3H), 2.12-1.81 (m, 2H), 1.56 (br. s., 3H), 1.43 (d, J=7.1 Hz, 6H). MS (ESI): m/z 1144.75 (M+H)$^+$.

(R)-2-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)-3-methylazetidine-3-carbonyloxy)ethylphosphonic acid (29) (BM-1083)

29 was prepared from 28 and dimethyl (2-hydroxyethyl)phosphonate according general procedure V. $^1$H NMR (300 M Hz, CD$_3$OD): δ 7.94 (d, J=1.8 Hz, 1H), 7.72 (dd, J=2.0, 9.1 Hz, 1H), 7.36-7.26 (m, 4H), 7.25-7.15 (m, 5H), 7.10-7.00 (m, 4H), 6.92-6.83 (m, 1H), 6.63 (s, 1H), 6.57 (d, J=12.0 Hz, 1H), 6.42 (d, J=9.2 Hz, 1H) 4.58-4.35 (m, 5H), 4.12-3.82 (m, 3H), 3.29-3.05 (m, 11H), 2.84 (s, 3H), 2.74 (s, 3H), 2.25-1.83 (m, 5H), 1.50 (br. s., 3H), 1.43 (d, J=7.1 Hz, 6H). MS (ESI): m/z 1252.83 (M+H)$^+$.

(R)-3-(1-(3-(4-(N-(4-(4-(3-(2-(4-chlorophenyl)-1-isopropyl-5-methyl-4-(methylsulfonyl)-1H-pyrrol-3-yl)-5-fluorophenyl)piperazin-1-yl)phenyl)sulfamoyl)-2-(trifluoromethylsulfonyl)phenylamino)-4-(phenylthio)butyl)-3-methylazetidine-3-carbonyloxy)propylphosphonic acid (30) (BM-1084)

30 was prepared from 28 and dimethyl (3-hydroxypropyl)phosphonate according general procedure V. $^1$H NMR (300 M Hz, CD$_3$OD): δ 7.94 (s, 1H), 7.71 (dd, 1.5, 9.0 Hz, 1H), 7.36-7.26 (m, 4H), 7.24-7.15 (m, 5H), 7.08-6.97 (m, 4H), 6.90-6.79 (m, 2H), 6.62 (s, 1H), 6.56 (d, J=11.8 Hz, 1H), 6.41 (d, J=8.8 Hz, 1H), 4.54-4.37 (m, 3H), 4.33-4.21 (m, 2H), 3.99 (br. s., 3H), 3.28-3.05 (m, 11H), 2.84 (s, 3H), 2.74 (s, 3H), 2.15-1.71 (m, 7H), 1.57 (s, 3H), 1.43 (d, J=7.0 Hz, 6H). MS (ESI): 1266.92 (M+H)$^+$.

Fluorescence Polarization Based Binding Assays for Bcl-2/Bcl-xL/Mcl-1 Proteins

Sensitive and quantitative fluorescence polarization (FP)-based assays were developed and optimized to determine the binding affinities of Bcl-2 family protein inhibitors to the recombinant Bcl-2, Bcl-xL, and Mcl-1 proteins.

Determine $K_d$ Values of Fluorescent Probes to Proteins

Homemade fluorescein labeled BIM (81-106), Bak (72-87) and BID (79-99) peptides, named as Flu-BIM, Flu-BAK, and Flu-BID were used as the fluorescent probes in FP assays for Bcl-2, Bcl-xL, and Mcl-1 respectively. By monitoring the total fluorescence polarization of mixtures composed with fluorescent probes at fixed concentrations and proteins with increasing concentrations up to the full saturation, the $K_d$ values of Flu-BIM to Bcl-2, Flu-BAK to Bcl-xL, and Flu-BID to Mcl-1 were determined to be 0.55±0.15 nM, 4.4±0.8, and 6.8±1.5 nM, respectively. Fluorescence polarization values were measured using the Infinite M-1000 multi-mode plate reader (Tecan U.S., Research Triangle Park, N.C.) in Microfluor 2 96-well, black, round-bottom plates (Thermo Scientific). To each well, 1 nM of Flu-BIM or 2 nM of Flu-BAK or 2 nM of Flu-BID and increasing concentrations of Bcl-2 or Bcl-xL or Mcl-1 were added to a final volume of 125 μl in the assay buffer (100 mM potassium phosphate, pH 7.5, 100 µg/ml bovine γ-globulin, 0.02% sodium azide, Invitrogen, with 0.01% Triton X-100 and 4% DMSO). Plates were incubated at room temperature for 2 hours with gentle shaking to assure equilibrium. The polarization values in millipolarization units (mP) were measured at an excitation wavelength of 485 nm and an emission wavelength of 530 nm. Equilibrium dissociation constants ($K_d$) were then calculated by fitting the sigmoidal dose-dependent FP increases as a function of protein concentrations using Graphpad Prism 5.0 software (Graphpad Software, San Diego, Calif.).

Determine $K_i$ Values of Bcl-2 Family Protein Inhibitors $K_i$ values of Bcl-2 family protein inhibitors to Bcl-2/Bcl-xL/Mcl-1 proteins were determined through an inhibitor dose-dependent competitive binding experiment in which serial dilutions of inhibitors competed against the fluorescent probe with fixed concentration for binding to a fixed concentration of the protein. Mixtures of 5 µl of the tested inhibitor in DMSO and 120 µl of pre-incubated protein/probe complex in the assay buffer were added into assay plates and incubated at room temperature for 2 hours with gentle shaking. Final concentrations of the protein and probe are 1.5 nM and 1 nM for the Bcl-2 assay, 10 nM and 2 nM for the Bcl-xL assay, and 20 nM and 2 nM for the Mcl-1 assay, respectively. Negative controls containing protein/probe complex only (equivalent to 0% inhibition), and positive controls containing free probe only (equivalent to 100% inhibition), were included in each assay plate. FP values were measured as described above. IC50 values were determined by nonlinear regression fitting of the competition curves. $K_i$ values of inhibitors were calculated using the home derived equation described before (Z. Nikolovska-Coleska et al., *Analytical Biochemistry*, 2004, 332, 261-273.), based upon the IC50 values obtained, the $K_d$ values of the probes to the proteins, and the concentrations of the proteins and probes in the competitive assays. $K_i$ values were also calculated by using another very commonly used equation present in the literatures (X. Y. Huang, *Journal of Biomolecular Screening*, 2003, 8, 34-38.), results from which consisted with our results extremely well.

Cell Growth Assay

RS4; 11 and H146 cells were seeded in 96-well cell culture plates at a density of 10,000 cells/well with serially diluted compounds and incubated at 37° C. in an atmosphere of 95% air and 5% $CO_2$ for 4 days. Cell viability was determined using the WST-8 (2-(2-methoxy-4-nitrophenyl)-3-(4-nitrophenyl)-5-(2,4-disulfophenyl)-2H-tetrazolium, monosodium salt) based Cell Counting-8 Kit (Dojindo Molecular Technologies, Inc., Rockville, Md.) according to the manufacture's instruction. Briefly, WST-8 was added to each well at a final concentration of 10% (v/v), and then the plates were incubated at 37° C. for 1-2 hours for color development. The absorbance was measured at 450 nm using a SPECTRAmax PLUS plate reader (Molecular Devices, Sunnyvale, Calif.).

The half maximal inhibitory concentration ($IC_{50}$) was calculated using the GraphPad Prism 5 software (GraphPad Software, La Jolla, Calif.).

Cell Death Assay

Cell death assay was performed using a Trypan blue exclusion test of cell viability. One million cells were seeded in 6-well plates and incubated at 37° C. in an atmosphere of 95% air and 5% $CO_2$ with or without compounds for the indicated time points. At the end of treatment, cells were collected and centrifuged at 1000 rpm for 5 minutes. The cell pellets were re-suspended in PBS and mixed with 0.4% Trypan blue (Invitrogen) at 1:1 dilution to determine cell viability using Olympus CKX41 microscope (Olympus, Center Valley, Pa.).

Apoptosis Assay

Apoptosis assay was performed using the Annexin-V-FLUOS Staining kit (Roche Diagnostics, Indianapolis, Ind.) according to the manufacturer's instruction. Briefly, cells were treated with compounds for the indicated time points, harvested and washed with PBS. Cells were stained with Annexin V-FITC and Propidium iodide for 15 minutes at room temperature in the dark before analyzed with a BD Biosciences FACSCaliburs (Becton Dickinson).

Western Blot Analysis

Cells were lysed with lysis buffer (PBS containing 1% NP40, 0.5% Na-deoxycholate, and 0.1% SDS) supplemented with protease inhibitors (α-complete, Roche). The protein extracts were quantified using a calorimetric assay (Bradford Reagent) (BioRad, Hercules, Calif.). Proteins were electrophoresed onto 4-20% SDS-PAGE gels (Invitrogen) and transferred onto polyvinylidene difluoride membranes (Bio-Rad). Following blocking in 5% milk, membranes were incubated with a specific primary antibody, washed, and incubated with horseradish peroxidase-linked secondary antibody (Pierce). The signals were visualized with the chemiluminescent horseradish peroxidase antibody detection reagent (Denville Scientific).

Cytochrome c and Smac Release Assay

Four million of H146 or RS4; 11 cells were treated with compounds at 37° C. in an atmosphere of 95% air and 5% $CO_2$ for the indicated time points, washed with PBS and re-suspended in 100 µl of digitonin buffer (75 mM NaCl, 8 mM Na2HPO4, 1 mM NaH2PO4, 1 mM EDTA, 350 digitonin, and 250 mM sucrose). Cytosolic fractions were separated from organelle membrane fraction by centrifugation at 13,000 rpm for 1 min. The cytosolic fractions were resolved on a 12% SDS-PAGE and probed using anti-cytochrome c antibody (BD Biosciences) and anti-Smac (Cell Signaling Technology, Danvers, Mass.) antibody.

In particular, a compound of the invention was assayed for affinity to Bcl-2, Bcl-xL, and Mcl-1. The assay results compared to assay results for ABT-737, a known, patent Bcl-2/Bcl-xL inhibitor, and to these peptides. The results are summarized in Table 1.

TABLE 1

Binding affinities to Bcl-2, Bcl-xL, and Mcl-1 proteins, as determined using established FP-based assays. 3-5 independent experiments were performed for each compound for each protein. ABT-737, BIM, BAD, and NOXA peptides were tested as controls.

| | Binding Affinities | | | | |
|---|---|---|---|---|---|
| | Bcl-2 | | Bcl-xL | | Mcl-1 |
| Compound | $IC_{50} \pm SD$ | $K_i \pm SD$ | $IC_{50} \pm SD$ | $K_i \pm SD$ | $IC_{50} \pm SD$ |
| ABT-737 | 2 ± 0.2 (nM) | <1 (nM) | 6 ± 2 (nM) | 1.6 ± 0.5 (nM) | >1 (µM) |
| BIM | <1 (nM) | <1 (nM) | <1 (nM) | <1 (nM) | 5 ± 1 (nM) |

TABLE 1-continued

Binding affinities to Bcl-2, Bcl-xL, and Mcl-1 proteins, as determined using established FP-based assays. 3-5 independent experiments were performed for each compound for each protein. ABT-737, BIM, BAD, and NOXA peptides were tested as controls.

| | Binding Affinities | | | | |
|---|---|---|---|---|---|
| | Bcl-2 | | Bcl-xL | | Mcl-1 |
| Compound | IC$_{50}$ ± SD | K$_i$ ± SD | IC$_{50}$ ± SD | K$_i$ ± SD | IC$_{50}$ ± SD |
| BAD | 40 ± 8 (nM) | 10 ± 2 (nM) | 5 ± 0.3 (nM) | 1.5 ± 0.1 (nM) | 32 ± 2 (µM) |
| NOXA | 17 ± 1 (µM) | 3.6 (µM) | 11 ± 2 (µM) | 3.4 (µM) | 37 ± 3 (µM) |

REFERENCES

1. D. Hanahan, et al., *Cell* 2000; 100:57-70.
2. S. W. Lowe, et al., *Carcinogenesis* 2000, 21, 485-495.
3. C. B. Thompson, *Science* 1995, 267, 1456-1462.
4. J. C. Reed, *Nat Rev Drug Discov* 2002; 1:111-121.
5. D. W. Nicholson, *Nature* 2000, 407, 810-816.
6. D. T. Chao, et al., *Annu Rev Immunol* 1998; 16:395-419.
7. J. C. Reed, *Advances in Pharmacology* 1997; 41:501-553.
8. J. C. Reed, et al. *J Cell Biochem* 1996; 60:23-32.
9. A. J. Minn, et al., *Advances in Immunology* 1998; 70:245-279.
10. J. M. Adams, et al., *Science* 1998; 281:1322-1326.
11. A. Ziegler, et al., *J Natl Cancer Inst* 1997; 89:1027-1036.
12. U. Zangemeister-Wittke, et al., *Br. J. Cancer* 1998; 78:1035-1042.
13. B. Jansen, et al., *Nature Medicine* 1998; 4:232-234.
14. U. Zangemeister-Wittke, et al., *Br J Cancer* 1998; 78:1035-1042.
15. O. Gautschi, et al., *J Natl Cancer Inst* 2001; 93:463-471.
16. M. Strasberg Rieber M, et al., *Clin Cancer Res* 2001; 7; 1446-1451.
17. S. Hopkins-Donaldson, et al., *Int J Cancer* 2003; 106: 160-166.
18. G. Wang, et al., *Proc Natl Acad Sci USA* 2000; 97:7124-7129.
19. A. Degterev, et al., *Nat Cell Biol* 2001; 3:173-182.
20. S. P. Tzung, et al., *Nat Cell Biol* 2001; 3:183-191.
21. I. J. Enyedy, et al., *J Med Chem* 2001; 44:4313-4324.
22. O. Kutzki, et al., *J Am Chem Soc* 2002; 124:11838-11839.
23. G. Wang, et al., *J Med Chem.* 2006; 49:6139-6142.
24. G. Tang, et al., *J Med Chem.* 2007 Apr. 19; 50(8):1723-6.
25. G. Tang, et al., *J Med Chem.* 2007; 50(14): 3163-6.
26. T. Oltersdorf, et al., *Nature.* 2005, 435(7042):677-81.
27. M. D. Wendt, et al., *J Med Chem.* 2006, 49(3):1165-81.
28. A. M. Petros, et al., *J Med Chem.* 2006, 49(2):656-63.
29. C. M. Park, et al., *J Am Chem Soc.* 2006 Dec. 20; 128(50): 16206-12.
30. A. R. Shoemaker, et al., *Cancer Res.* 2006, 66(17):8731-9.
31. M. Bruncko, et al., *J Med Chem.* 2007, 50(4):641-62.
32. C. M. Park, et al., *J Med Chem.* 2008, 51(21):6902-15.
33. A. R. Shoemaker, et al., *Clin Cancer Res.* 2008 Jun. 1; 14(11):3268-77.
34. C. Tse, et al., *Cancer Res.* 2008 May 1; 68(9):3421-8.
35. M. Vogler, et al., *Cell Death Differ.* 2009 March; 16(3): 360-7.
36. T. N. Chonghaile, et al., *Oncogene.* 2008; 27 Suppl 1:S149-57.
37. M. H. Kang, et al. *Clin Cancer Res.* 2009 Feb. 15; 15(4): 1126-32.
38. S. W. Muchmore, et al., *Nature* 1996; 381:335-341.
39. M. Aritomi, et al., *J Biol Chem* 1997; 272:27886-27892.
40. M. Sattler, et al., *Science* 1997; 275:983-986.
41. A. M. Petros, et al. *Protein Sci* 2000; 9:2528-2534.
42. A. M. Petros, et al. *Proc Natl Acad Sci USA* 2001; 98:3012-3017.
43. X Liu, et al. *Immunity.* 2003 September; 19(3):341-52.
44. E. F. Lee, et al., *Cell Death Differ.* 2007 September; 14(9):1711-3. (PDB ID: 2YXJ).
45. http://www.clinicaltrials.gov/
46. S. K. Tahir S K, et al. *Cancer Res.* 2007; 67(3):1176-83.
47. V. D. G. Moore, et al., *J Clin Invest.* 2007; 117:112-121.
48. M. Vogler, et al., *Cell Death Differ.* 2008; 15: 820-830.
49. M. Vogler, et al., *Blood.* 2009; 113:1710-1722.

What is claimed is:

1. A compound having a structural formula:

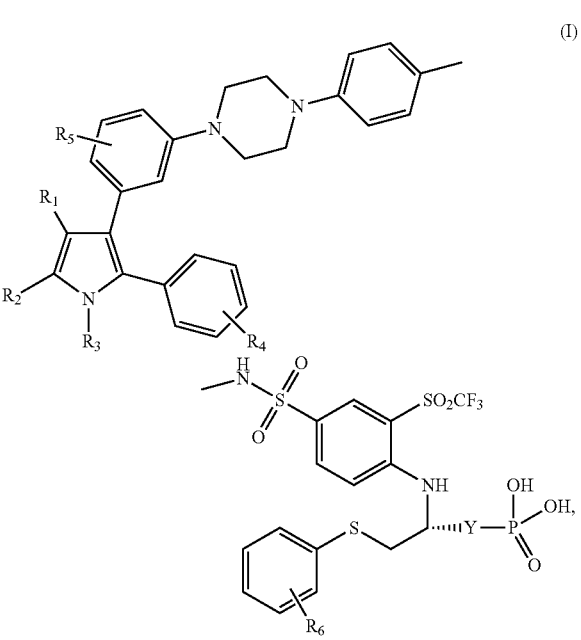

(I)

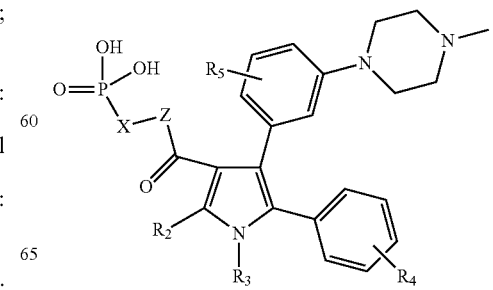

(II)

-continued (III)

wherein the A ring is

X is selected from the group consisting of alkylene, alkenylene, cycloalkylene, cycloalkenylene, and heterocycloalkylene;

Y is selected from the group consisting of $(CH_2)_n$—$N(R^a)$ and

Q is selected from the group consisting of O, $O(CH_2)_{1-3}$, $NR^c$, $NR^c(C_{1-3}alkylene)$, $OC(=O)(C_{1-3}alkylene)$, $C(=O)O$, $C(=O)O(C_{1-3}\ alkylene)$, $NHC(=O)(C_{1-3}\ alkylene)$, $C(=O)NH$, and $C(=O)NH(C_{1-3}\ alkylene)$;

Z is O or $NR^c$;

$R_1$ and $R_2$, independently, are selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", COR', $CO_2R'$, OCOR', CONR'R", $CONR'SO_2R"$, NR'COR", NR'CONR"R'", NR'C=SNR"R'", $NR'SO_2R"$, $SO_2R'$, and $SO_2NR'R"$;

$R_3$ is selected from a group consisting of H, alkyl, cycloalkyl, alkenyl, cycloalkenyl, alkynyl, aryl, heteroaryl, heterocycloalkyl, OR', NR'R", OCOR', $CO_2R'$, COR', CONR'R", $CONR'SO_2R"$, $C_{1-3}$ alkyleneCH(OH)$CH_2OH$, $SO_2R'$, and $SO_2NR'R"$;

R', R", and R'", independently, are H, alkyl, cycloalkyl, alkenyl, cycloalkenyl, alkynyl, aryl, heteroaryl, $C_{1-3}$ alkyleneheterocycloalkyl, or heterocycloalkyl;

$R_4$ is hydrogen, halo, $C_{1-3}$alkyl, $CF_3$, or CN;

$R_5$ is hydrogen, halo, $C_{1-3}$alkyl, hydroxyalkyl, or alkoxy;

$R_6$ is selected from the group consisting of H, CN, $NO_2$, halo, alkyl, cycloalkyl, alkenyl, cycloalkenyl, alkynyl, aryl, heteroaryl, heterocycloalkyl, OR', SR', NR'R", $CO_2R'$, OCOR', CONR'R", $CONR'SO_2R"$, NR'COR", NR'CONR"R'", NR'C=SNR"R'", $NR'SO_2R"$, $SO_2R'$, and $SO_2NR'R"$;

$R_7$ is selected form the group consisting of hydrogen, alkyl, alkenyl, $(CH_2)_{0-3}$cycloalkyl, optionally substituted with —OH$(CH_2)_{0-3}$cycloalkenyl, $(CH_2)_{0-3}$heterocycloalkyl, optionally substituted with —OH$(CH_2)_{0-3}$aryl, and $(CH_2)_{0-3}$heteroaryl;

$R_8$ is selected form the group consisting of hydrogen, halo, $NO_2$, CN, $CF_3SO_2$, and $CF_3$;

$R_a$ is selected from the group consisting of hydrogen, alkyl, heteroalkyl, alkenyl, hydroxyalkyl, alkoxy, cycloalkyl, cycloalkenyl, and heterocycloalkyl;

$R_b$ is hydrogen or alkyl;

$R_c$ is selected from the group consisting of hydrogen, alkyl, hydroxyalkyl, and alkoxy; and n, r, and s, independently, are 1, 2, 3, 4, 5, or 6;

or a pharmaceutically acceptable salt of (I), (II), or (III).

2. The compound of claim 1 wherein X is alkylene.

3. The compound of claim 1 wherein Y is

4. The compound of claim 3 wherein n is 1-3.

5. The compound of claim 3 wherein $R_b$ is hydrogen or $C_{1-3}$alkyl.

6. The compound of claim 1 wherein Q is O, $O(CH_2)_{1-3}$, $C(=O)O(CH_2)_{1-3}$, $OC(=O)(CH_2)_{1-3}$, or $C(=O)O(CH(CH_3)CH_2)$.

7. The compound of claim 1 wherein Z is O, NH, or $N(C_{1-3}alkyl)$.

8. The compound of claim 1 wherein $R_1$ is $SO_2R'$, $SO_2NR'R"$, NR'SOR", H, or alkyl.

9. The compound of claim 1 wherein $R_2$ is H, $C_{1-3}$alkyl, cycloalkyl, or halo.

10. The compound of claim 1 wherein $R_3$ is H, $C_{1-3}$alkyl, or cycloalkyl.

11. The compound of claim 1 wherein $R_4$ is H or halo.

12. The compound of claim 1 wherein $R_5$ is H, halo, or $C_{1-3}$alkyl.

13. The compound of claim 1 wherein $R_6$ is H, halo, $C_{1-3}$alkyl, or cycloalkyl.

14. The compound of claim 1 wherein $R_7$ is $(CH_2)_{0-3}$cycloalkyl optionally substituted with —OH or $(CH_2)_{0-3}$heterocycloalkyl optionally substituted with —OH.

15. The compound of claim 1 wherein $R_8$ is $CF_3SO_2$ or $CF_3$.

16. The compound of claim 1 wherein $R_b$ and $R_c$, independently, are H or $C_{1-3}$alkyl.

17. A compound having a structure
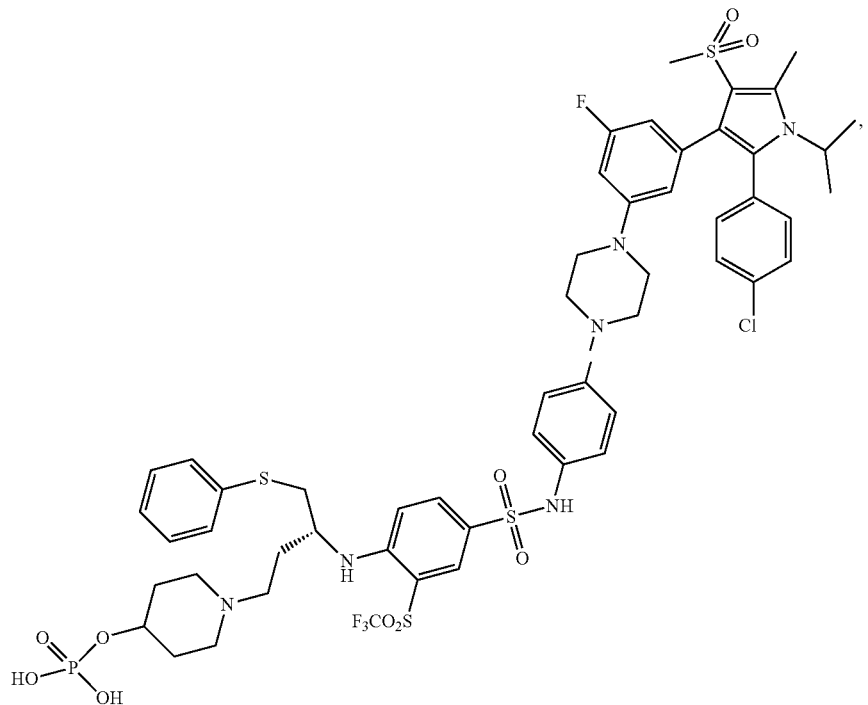
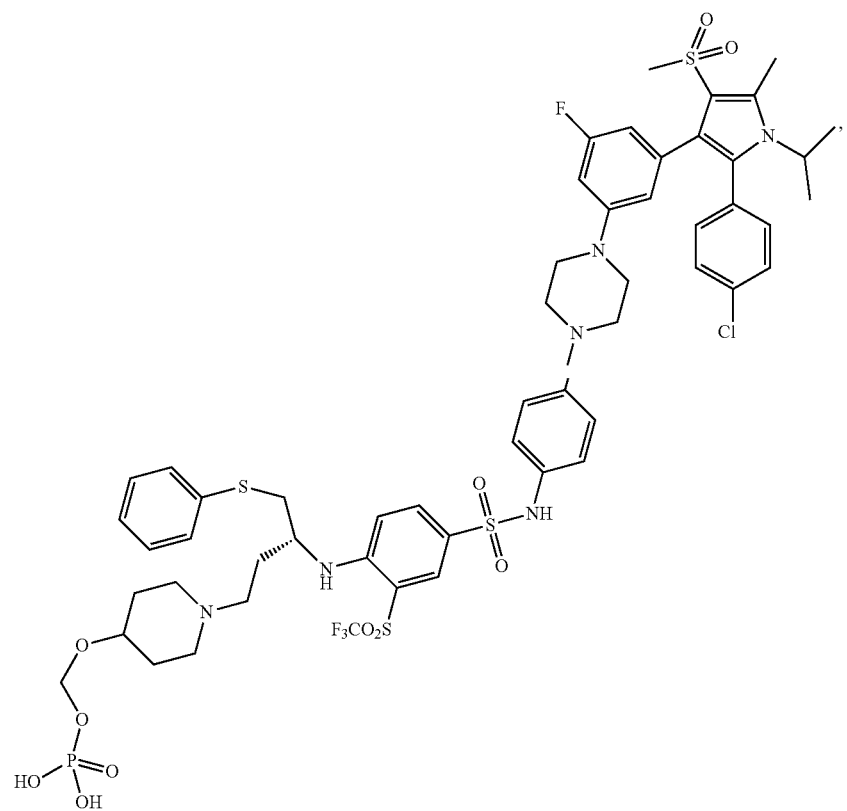

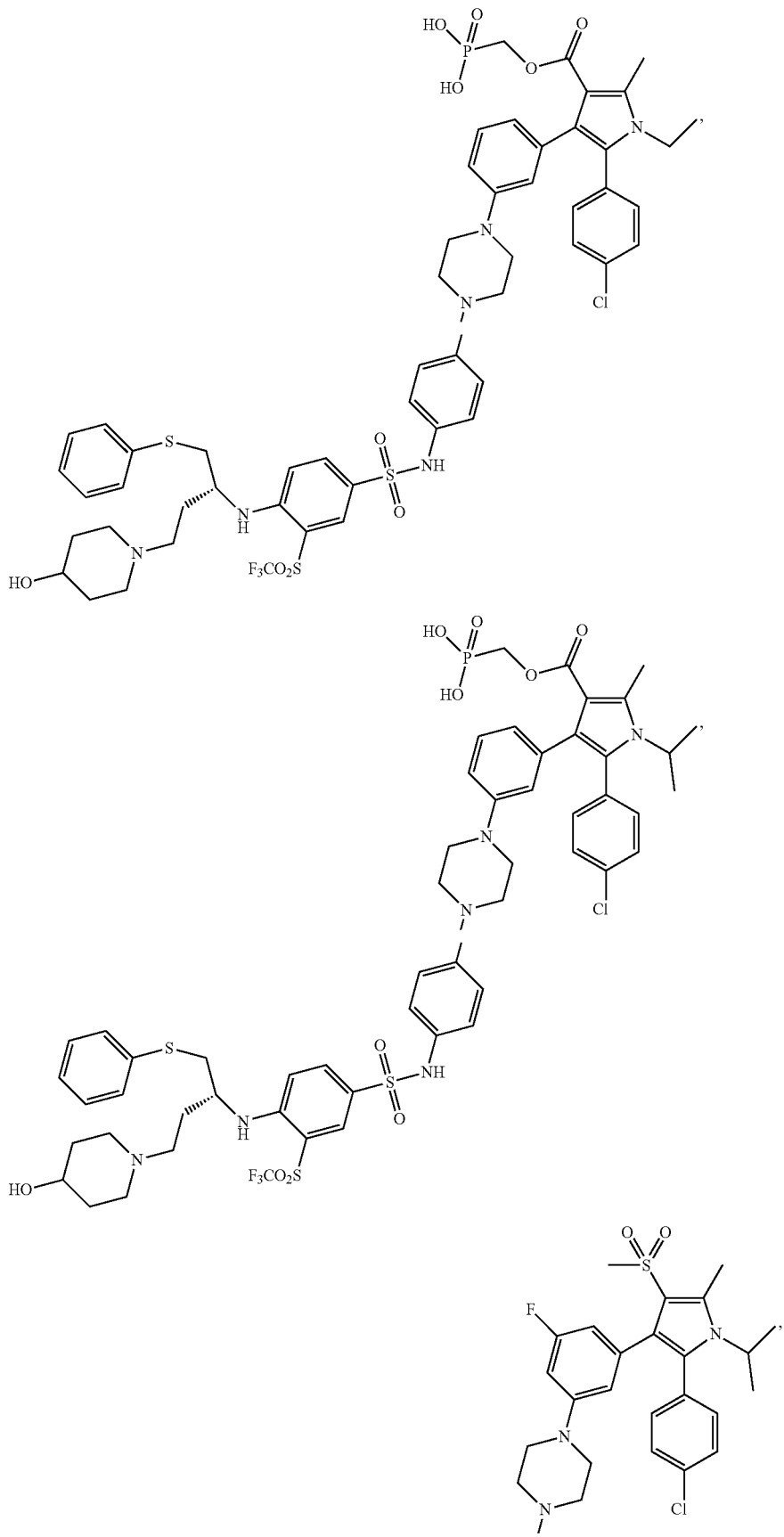

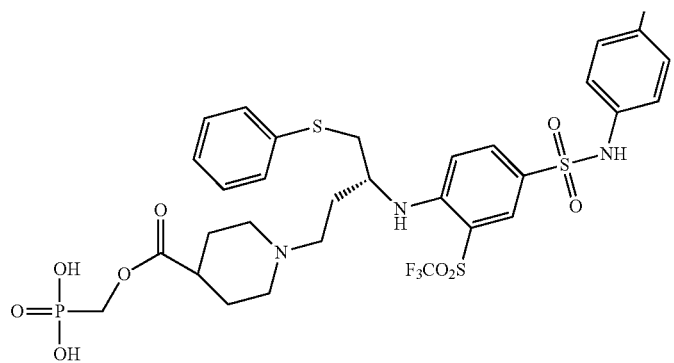
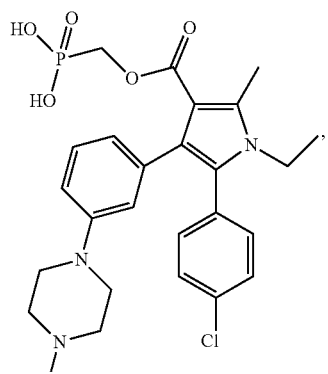
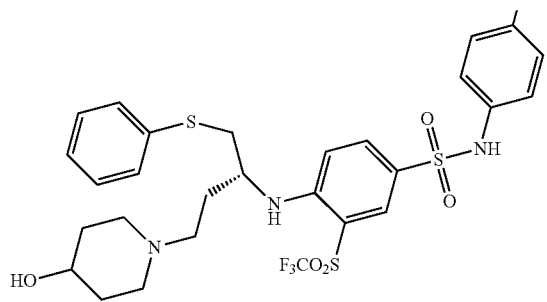
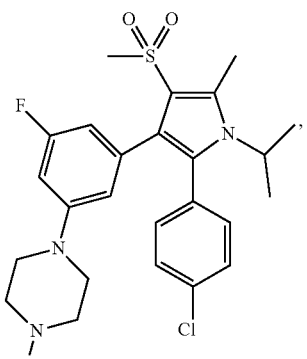

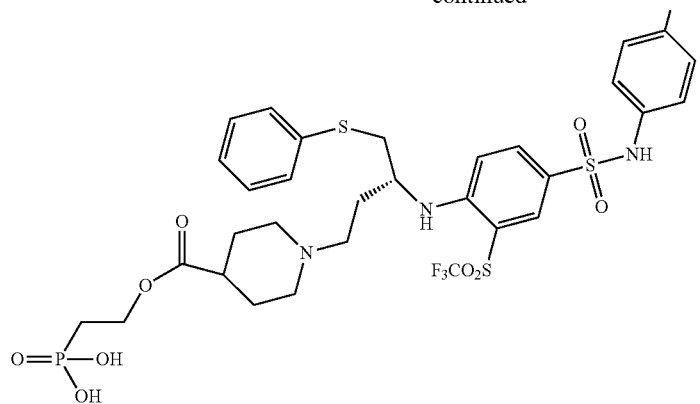
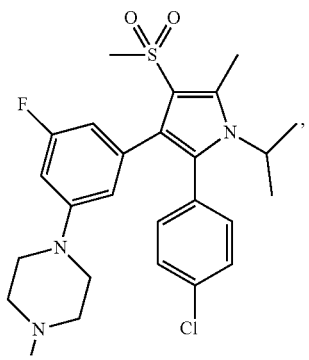
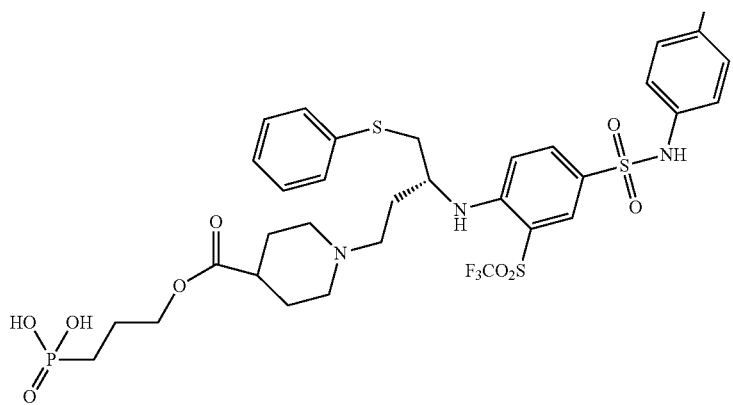
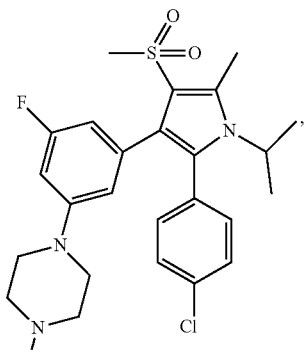

-continued
121
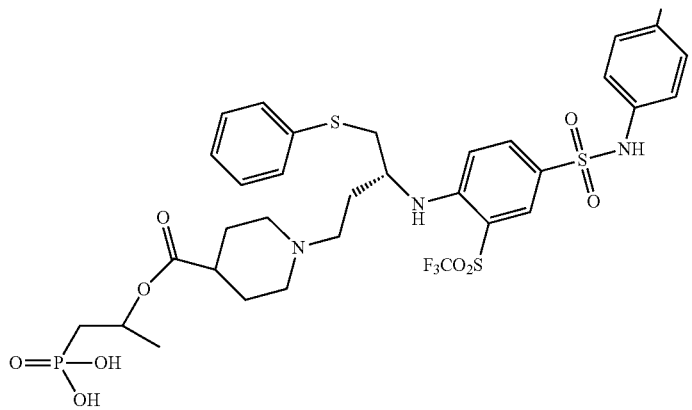
122
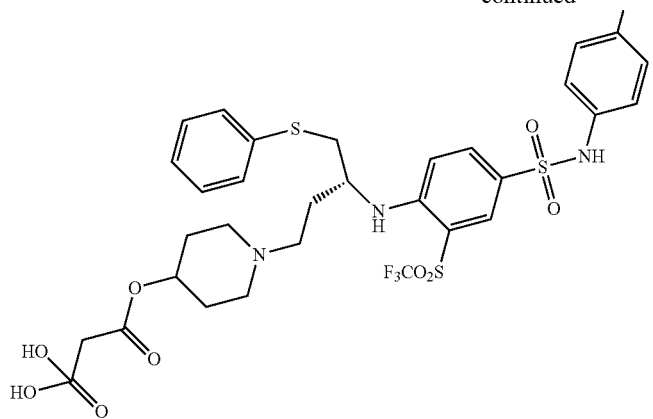
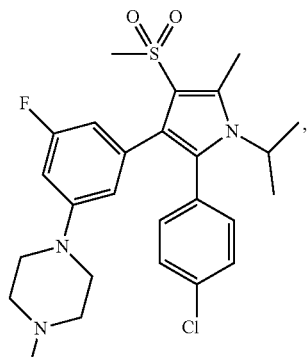
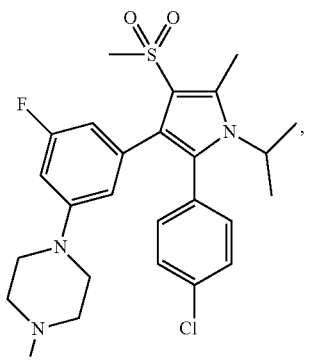

-continued
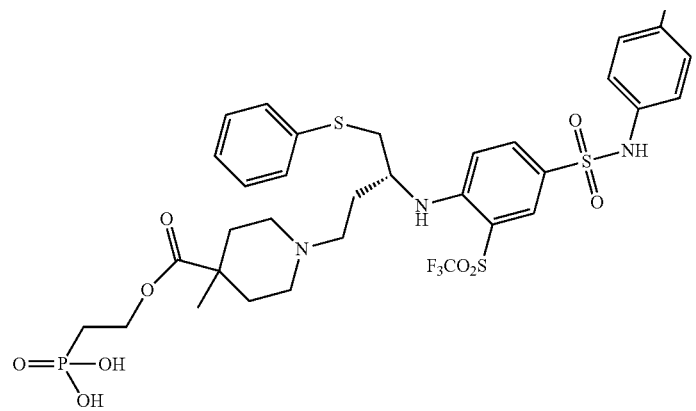
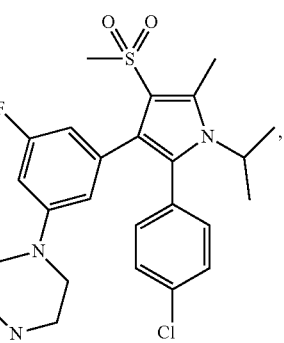
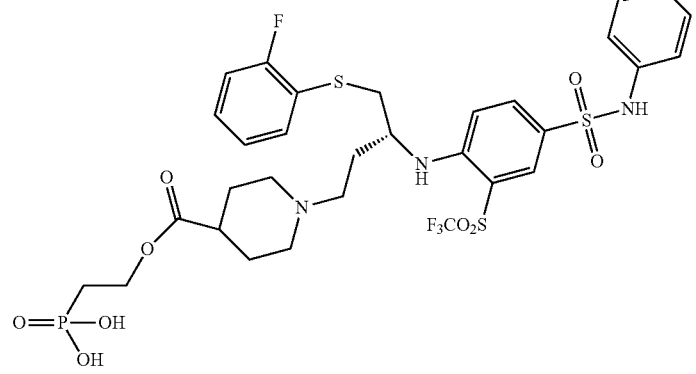
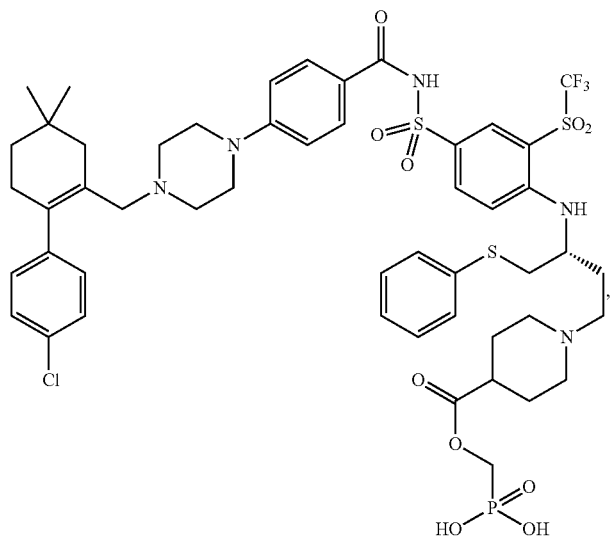

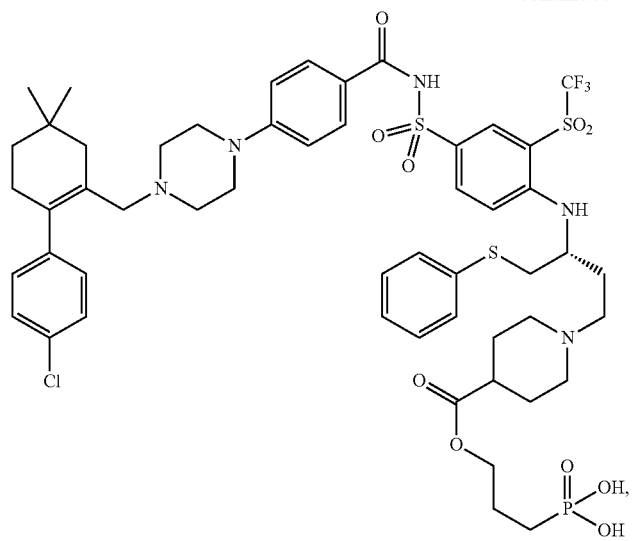
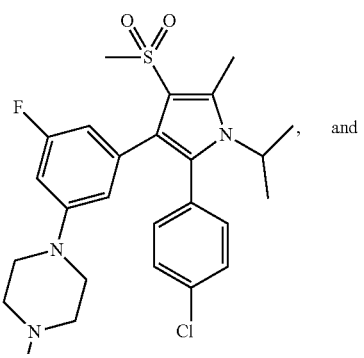
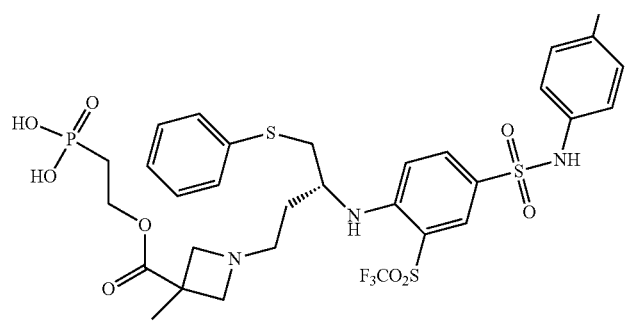
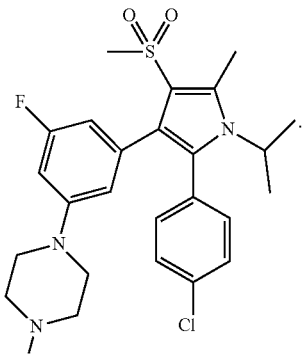

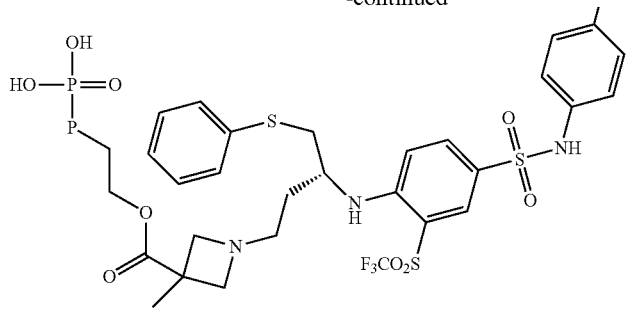
18. A pharmaceutical composition comprising a compound of claim 1 and a pharmaceutically acceptable carrier or vehicle.
* * * * *

UNITED STATES PATENT AND TRADEMARK OFFICE
CERTIFICATE OF CORRECTION

PATENT NO.        : 9,096,625 B2                                        Page 1 of 11
APPLICATION NO.   : 14/155809
DATED             : August 4, 2015
INVENTOR(S)       : Shaomeng Wang et al.

It is certified that error appears in the above-identified patent and that said Letters Patent is hereby corrected as shown below:

In the Claims:

At Column 112, line 18, "R₇ is selected form" should be -- R₇, is selected from --.

At Column 112, line 23, "form" should be -- from --.

At Columns 113 & 114, lines 1-30,

"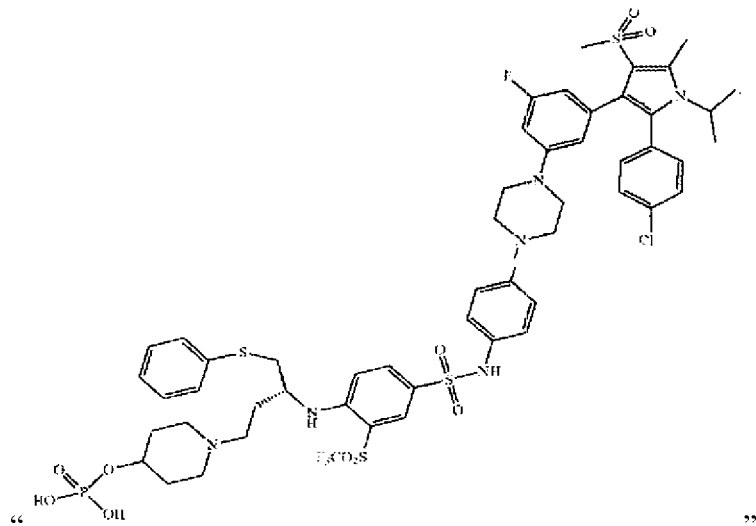"

Signed and Sealed this
Ninth Day of August, 2016

Michelle K. Lee
*Director of the United States Patent and Trademark Office*

CERTIFICATE OF CORRECTION (continued)
U.S. Pat. No. 9,096,625 B2 should be --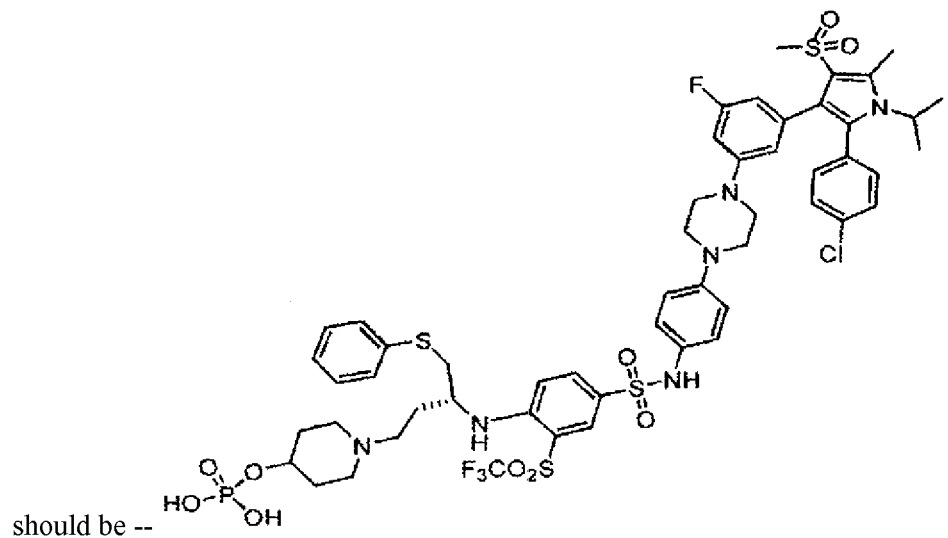--.

At Columns 113 & 114, lines 38-67,

"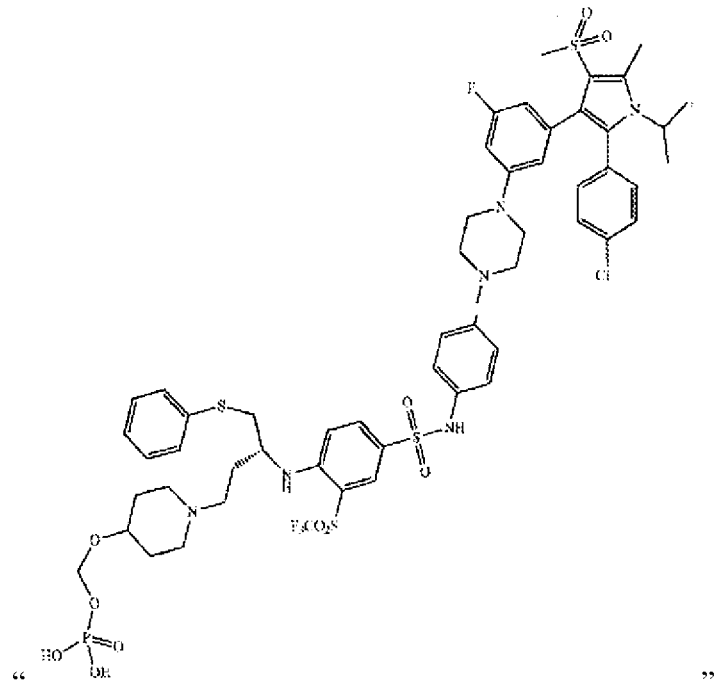"

CERTIFICATE OF CORRECTION (continued)
U.S. Pat. No. 9,096,625 B2

Page 3 of 11 should be -- 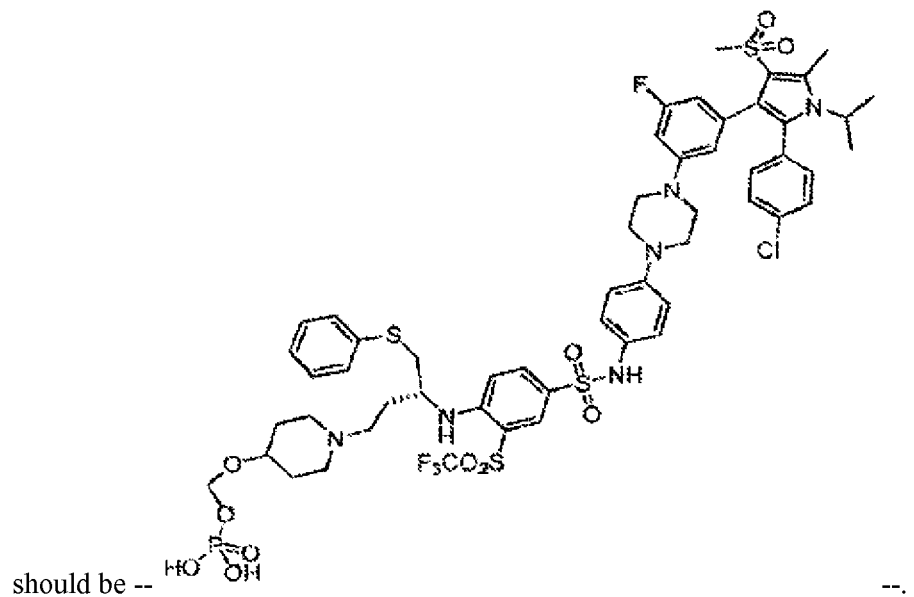 --.

At Columns 115 & 116, lines 1-26,

" 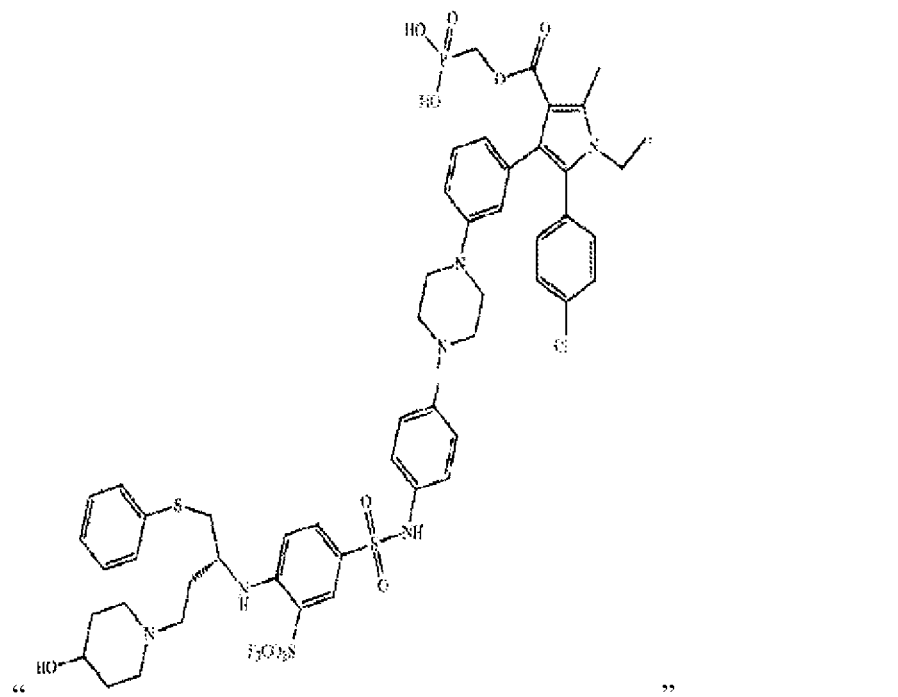 ".

CERTIFICATE OF CORRECTION (continued)
U.S. Pat. No. 9,096,625 B2 should be -- 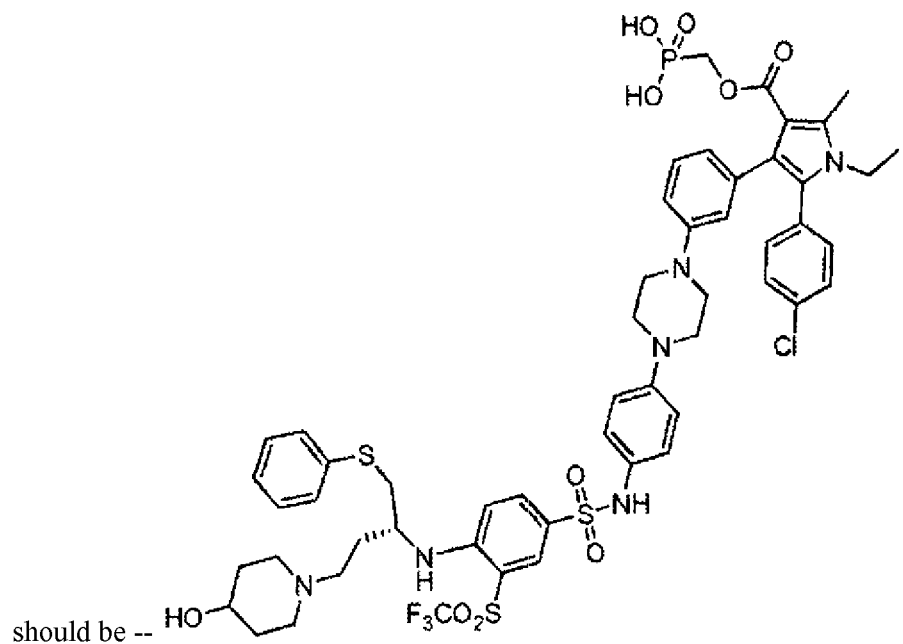 --.

At Columns 115 & 116, lines 28-52,

" 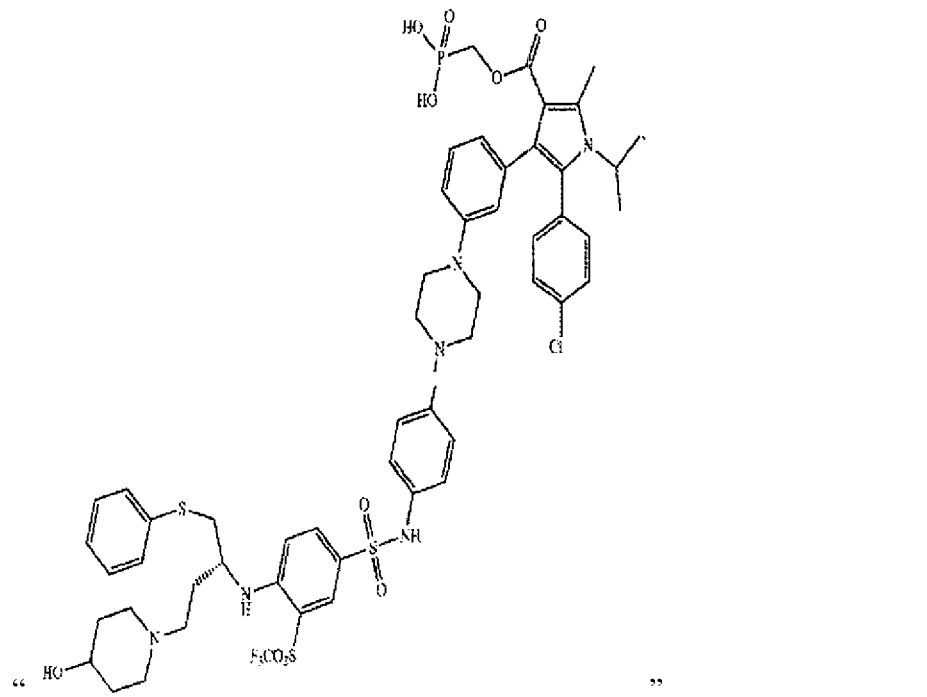 "

CERTIFICATE OF CORRECTION (continued)
U.S. Pat. No. 9,096,625 B2 should be -- 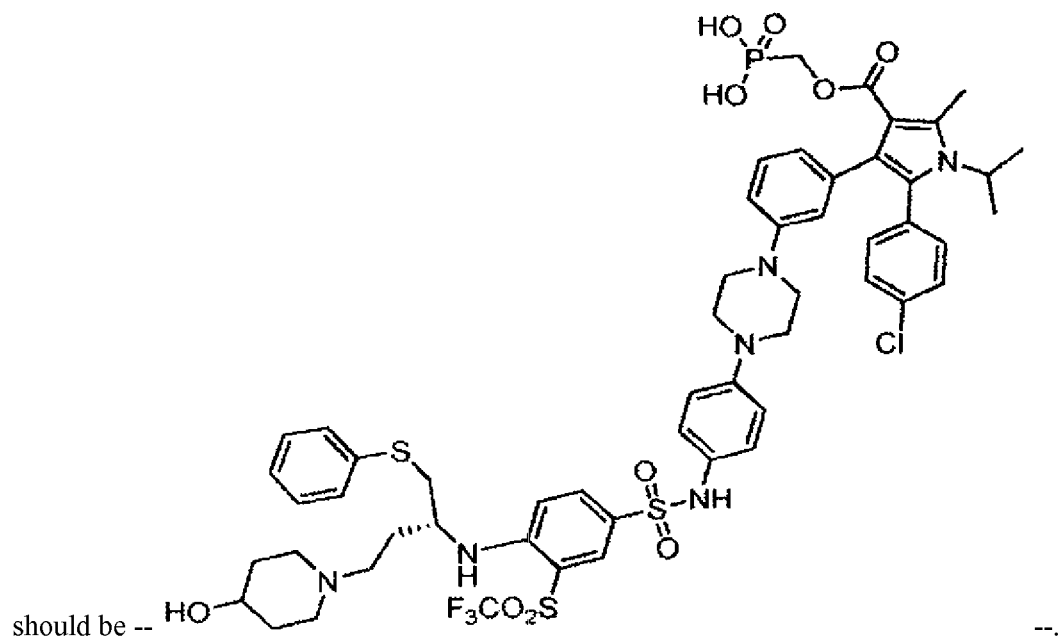 --.

At Columns 117 & 118, lines 21-50,

" 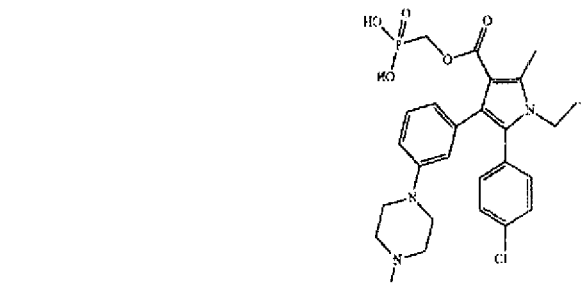

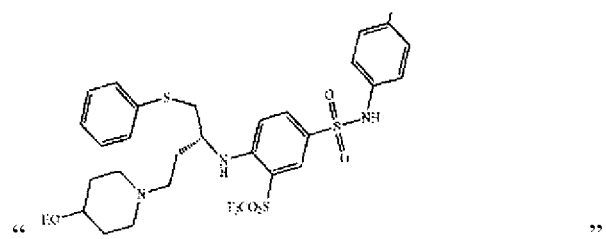 "

CERTIFICATE OF CORRECTION (continued)
U.S. Pat. No. 9,096,625 B2 should be -- 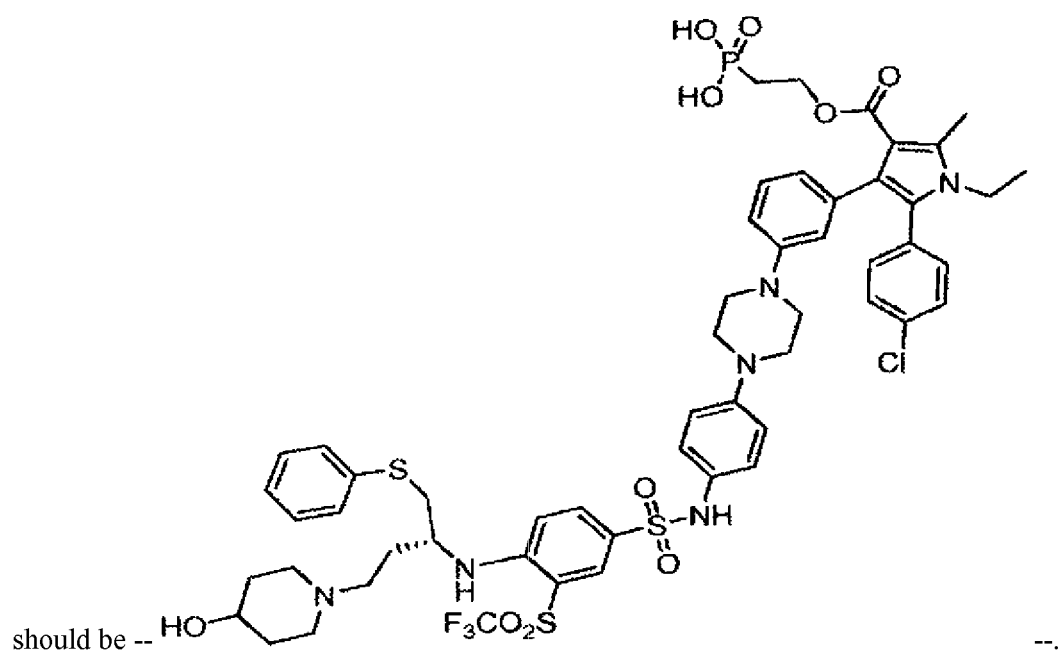 --.

At Columns 119 & 120, lines 19-51,

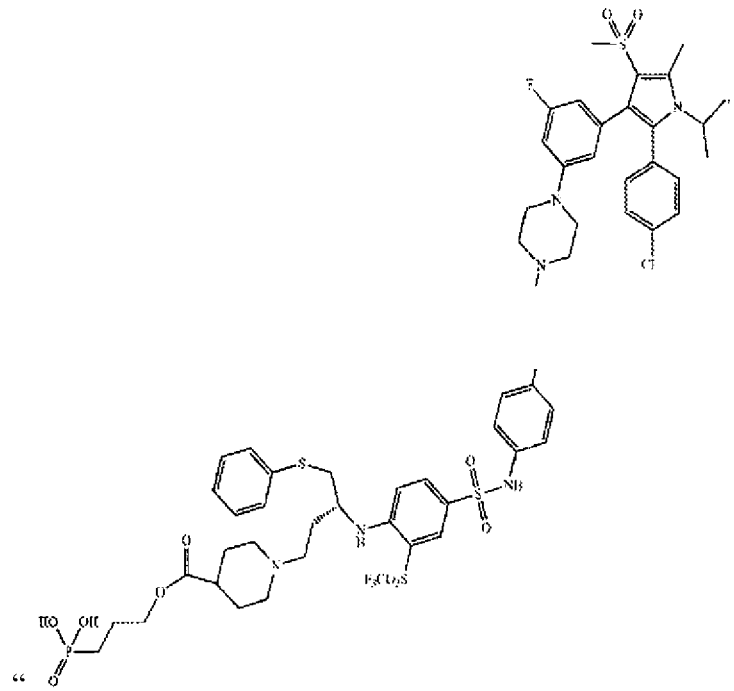

" "

should be --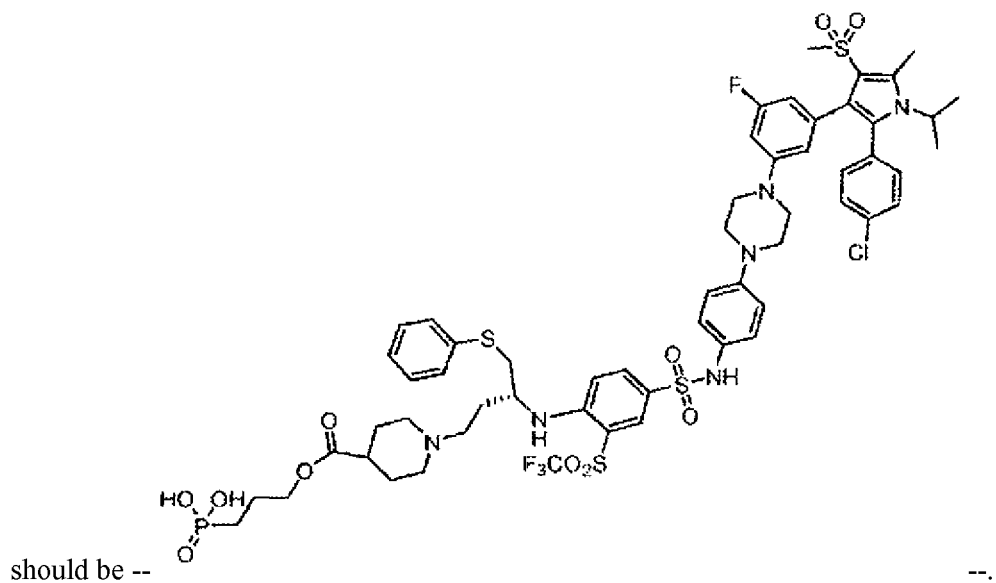--.
At Columns 121 & 122, lines 19-51,
"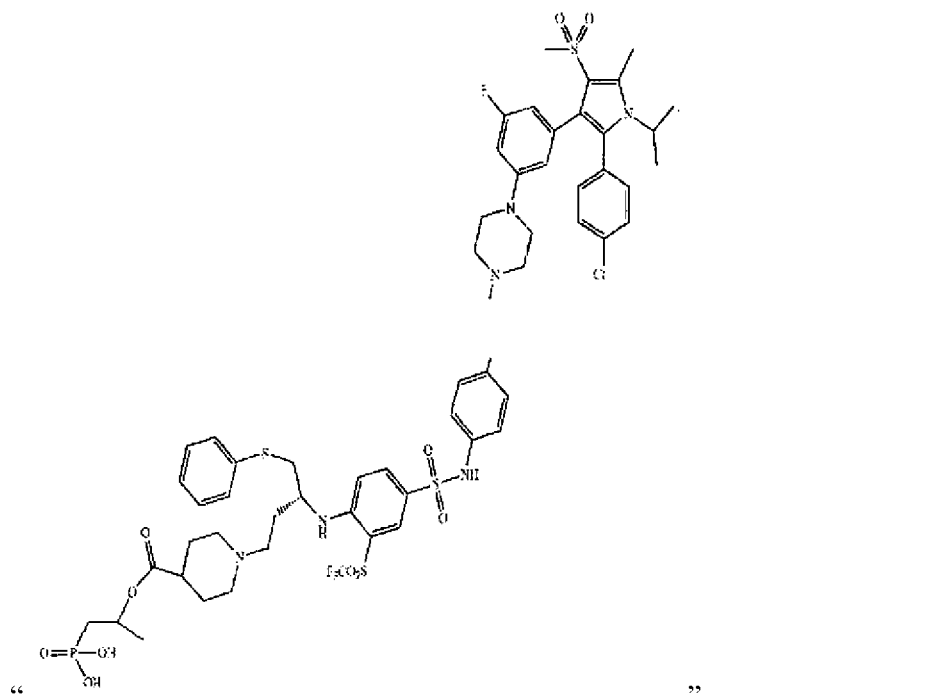"

CERTIFICATE OF CORRECTION (continued)
U.S. Pat. No. 9,096,625 B2

Page 8 of 11 should be -- 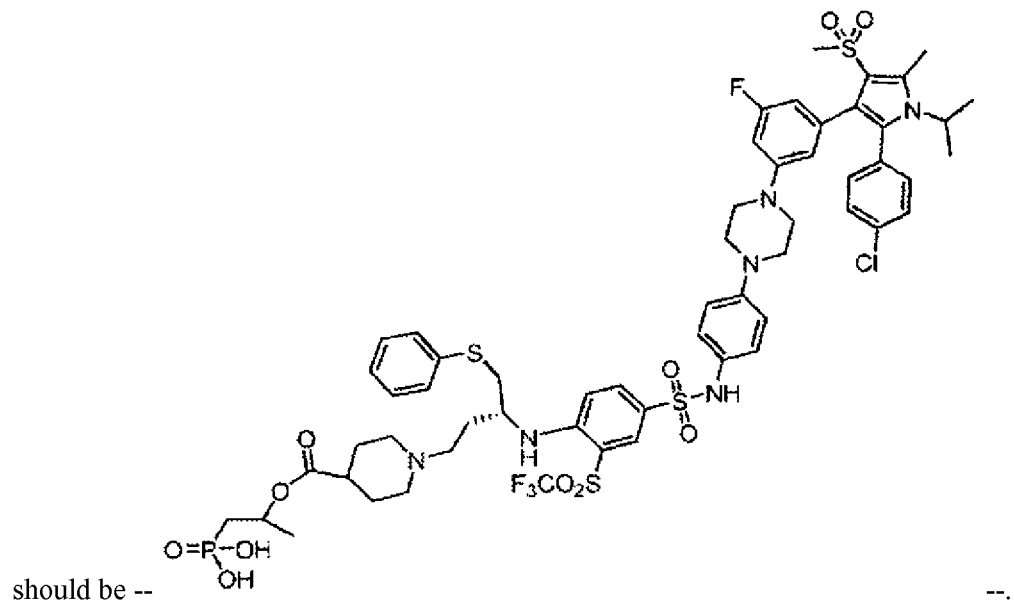 --.

At Columns 123 & 124, lines 18-46,

" 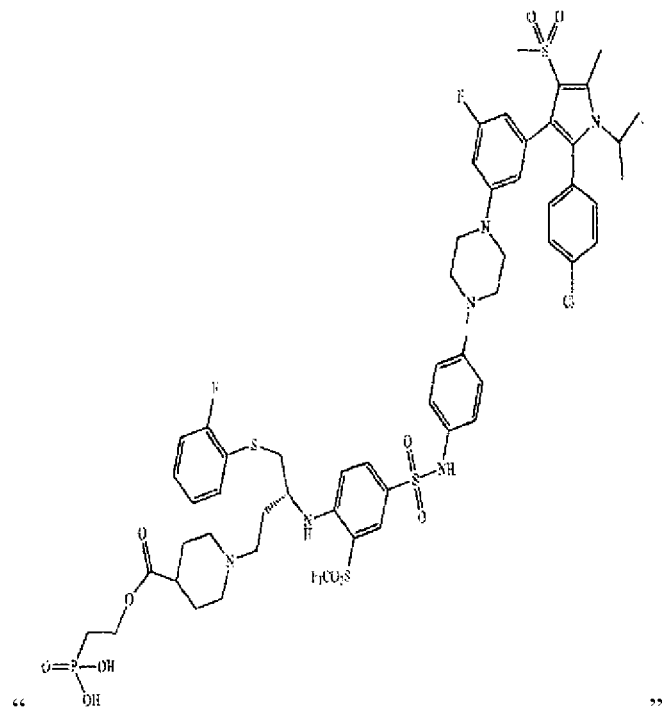 "

CERTIFICATE OF CORRECTION (continued)
U.S. Pat. No. 9,096,625 B2

Page 9 of 11 should be --  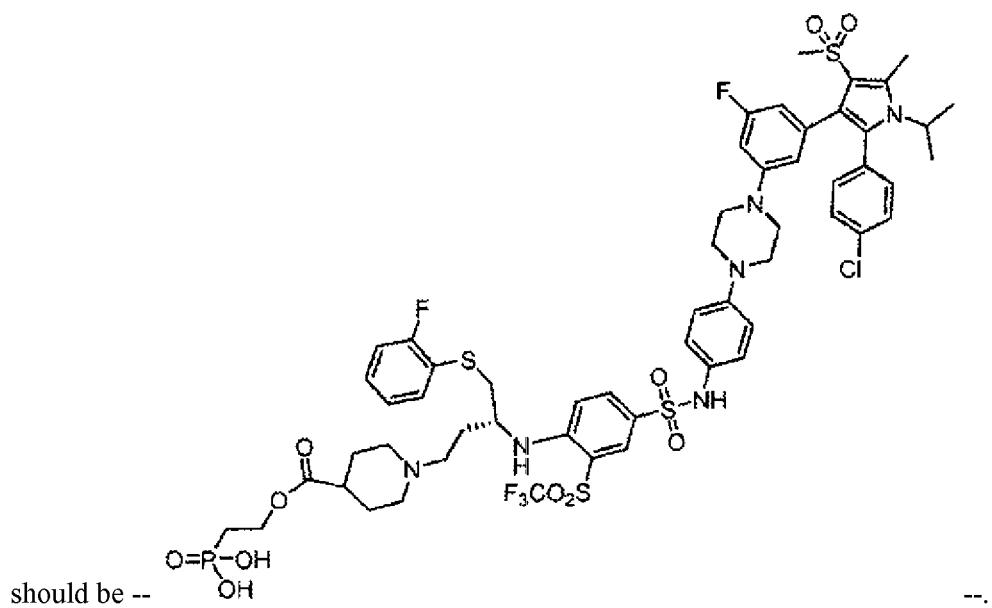 --.

At Columns 125 & 126, lines 28-52,

" 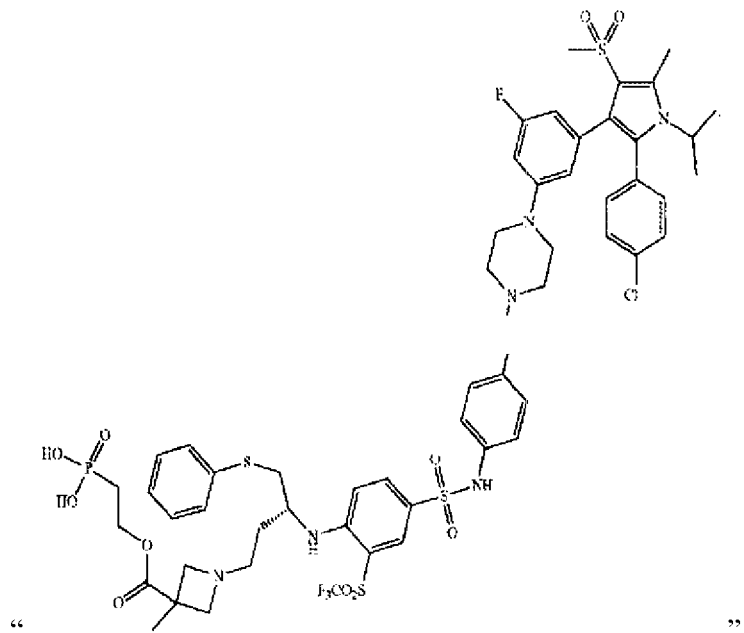 "

CERTIFICATE OF CORRECTION (continued)
U.S. Pat. No. 9,096,625 B2 should be -- 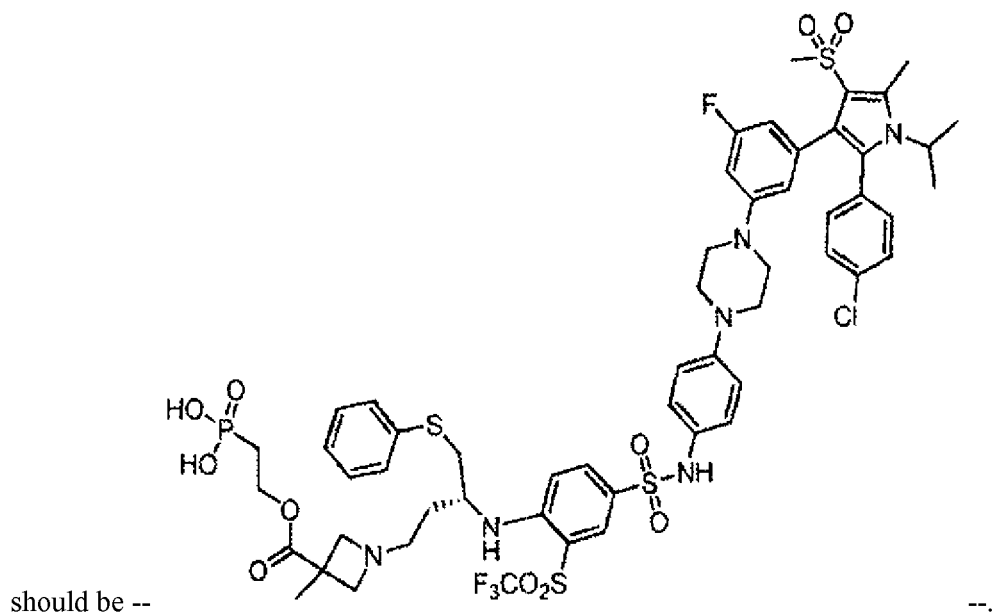 --.

At Columns 127 & 128, lines 1-11,

" 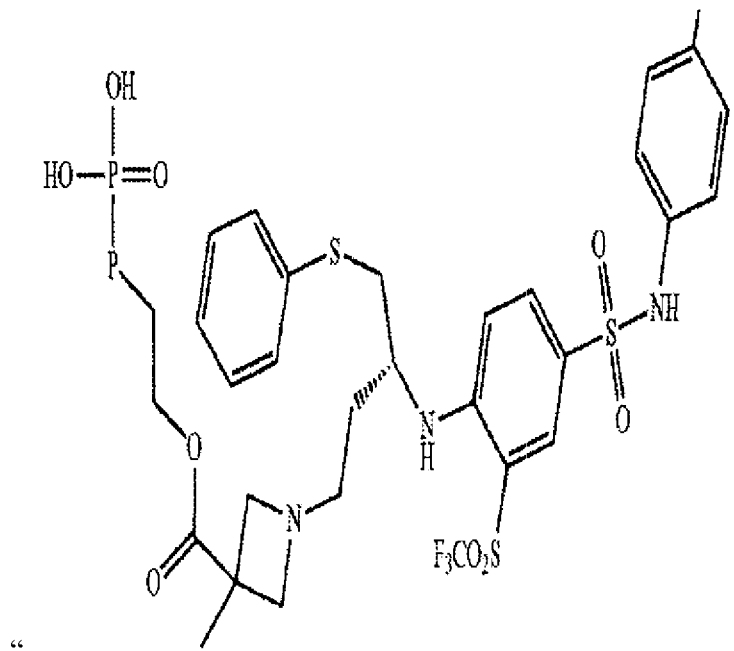 "

CERTIFICATE OF CORRECTION (continued)

U.S. Pat. No. 9,096,625 B2 should be -- 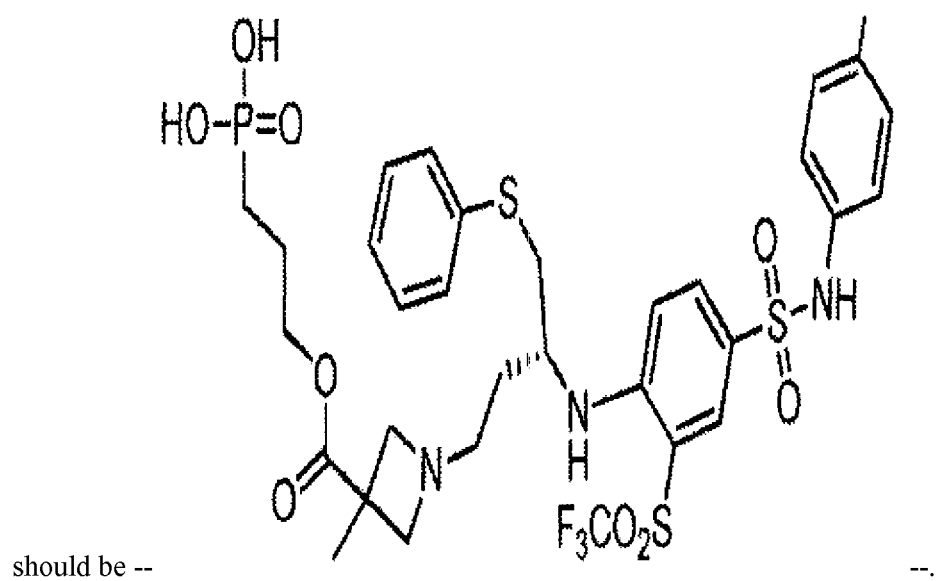 --.